United States Patent
Gray

(10) Patent No.: US 11,230,720 B2
(45) Date of Patent: Jan. 25, 2022

(54) NUCLEIC ACID MOLECULES CONTAINING SPACERS AND METHODS OF USE THEREOF

(71) Applicant: Audentes Therapeutics, Inc., San Francisco, CA (US)

(72) Inventor: John T. Gray, San Francisco, CA (US)

(73) Assignee: Audentes Therapeutics, Inc., San Francisco, CA (US)

( * ) Notice: Subject to any disclaimer, the term of this patent is extended or adjusted under 35 U.S.C. 154(b) by 598 days.

(21) Appl. No.: 15/768,071

(22) PCT Filed: Oct. 14, 2016

(86) PCT No.: PCT/US2016/057055
§ 371 (c)(1),
(2) Date: Apr. 13, 2018

(87) PCT Pub. No.: WO2017/066579
PCT Pub. Date: Apr. 20, 2017

(65) Prior Publication Data
US 2018/0305715 A1   Oct. 25, 2018

Related U.S. Application Data

(66) Substitute for application No. 62/241,483, filed on Oct. 14, 2015.

(51) Int. Cl.
| | | |
|---|---|---|
| *C12N 15/86* | (2006.01) | |
| *C12N 15/113* | (2010.01) | |
| *C12N 15/864* | (2006.01) | |
| *A61K 48/00* | (2006.01) | |
| *C12N 5/10* | (2006.01) | |

(52) U.S. Cl.
CPC ............ *C12N 15/86* (2013.01); *C12N 15/113* (2013.01); *A61K 48/00* (2013.01); *C12N 2310/141* (2013.01); *C12N 2750/14143* (2013.01); *C12N 2800/70* (2013.01); *C12N 2800/90* (2013.01); *C12N 2830/008* (2013.01); *C12N 2830/38* (2013.01); *C12N 2830/42* (2013.01)

(58) Field of Classification Search
None
See application file for complete search history.

(56) References Cited

U.S. PATENT DOCUMENTS

| | | |
|---|---|---|
| 6,274,354 B1 | 8/2001 | Wilson et al. |
| 6,346,415 B1 | 2/2002 | Feldhaus |
| 6,566,128 B1 | 5/2003 | Graham et al. |
| 9,169,494 B2 | 10/2015 | Hewitt et al. |
| 2002/0182595 A1 | 12/2002 | Weitzman et al. |
| 2004/0110266 A1 | 6/2004 | Chiorini et al. |
| 2004/0137626 A1 | 7/2004 | Wagner et al. |
| 2008/0153156 A1 | 6/2008 | Gray |
| 2011/0269735 A1 | 11/2011 | Shiffman et al. |
| 2012/0117674 A1 | 5/2012 | Kaplitt et al. |
| 2013/0109742 A1 | 5/2013 | Hewitt et al. |
| 2016/0032319 A1 | 2/2016 | Wright et al. |
| 2016/0102297 A1 | 4/2016 | Hewitt et al. |
| 2017/0233456 A1 | 8/2017 | Sabatino et al. |
| 2018/0126006 A1 | 5/2018 | Gray |

FOREIGN PATENT DOCUMENTS

| | | |
|---|---|---|
| WO | WO-01/36623 A2 | 5/2001 |
| WO | WO-02/097056 A2 | 12/2002 |
| WO | WO-2004/029278 A2 | 4/2004 |
| WO | WO-2011/088081 A1 | 7/2011 |
| WO | WO 2012/158757 | * 11/2012 |
| WO | WO-2012/158757 A1 | 11/2012 |
| WO | WO-2013/173129 A2 | 11/2013 |
| WO | WO-2014/064277 A1 | 5/2014 |
| WO | WO-2014/144486 A2 | 9/2014 |
| WO | WO-2014/167253 A1 | 10/2014 |
| WO | WO-2015/066034 A1 | 5/2015 |
| WO | WO-2016/183422 A1 | 11/2016 |

OTHER PUBLICATIONS

Barzel et al, Promoterless gene targeting without nucleases ameliorates haemophilia B in mice, Nature. Jan. 15, 2015; 517(7534): 360-364.*
Faust et al, CpG-depleted adeno-associated virus vectors evade immune detection.*
Doe Joint Genome Institute et al., "*Homo sapiens* chromosome 19 clone CTD-2587H24, complete sequence," GenBank: AC010327.8 (2002) (61 pages).
Hillgenberg et al., "Chromosomal integration pattern of a helper-dependent minimal adenovirus vector with a selectable marker inserted into a 27.4-kilobase genomic staffer," J Virol. 75(20):9896-908 (2001).
Muzny et al., "*Homo sapiens* 12 BAC RP11-592O2 (Roswell Park Cancer Institute Human BAC Library) complete sequence," GenBank: AC126309.8 (2003) (74 pages).
Voigtlander et al., "A Novel Adenoviral Hybrid-vector System Carrying a Plasmid Replicon for Safe and Efficient Cell and Gene Therapeutic Applications," Mol Ther Nucleic Acids 2:e83 (2013) (14 pages).
Gray et al., Chapter 2: Design and Construction of Functional AAV Vectors. *Adeno-Associated Virus: Methods and Protocols* vol. 807. Richard O. Snyder and Philippe Moullier (eds.), pp. 25-46 (2011).
Brimble et al., "Abstract 547: AAV Preparations Contain Contamination from DNA Sequences in Production Plasmids Directly Outside of the ITRs," Molecular Therapy. 24(Supplpement 1):S218-S219 (2016) (Abstract only).

(Continued)

*Primary Examiner* — Maria Marvich
(74) *Attorney, Agent, or Firm* — Clark & Elbing LLP

(57) ABSTRACT

The present invention relates nucleic acid molecules and concatemers containing spacer sequences useful for the efficient packaging of viral particles so as to minimize the incorporation of contaminant nucleic acids into these vectors, as well as methods of producing such viral particles.

56 Claims, 1 Drawing Sheet
Specification includes a Sequence Listing.

(56) References Cited

OTHER PUBLICATIONS

Ruffing, M. et al., "Mutations in the Carboxy Terminus of Adena-Associated Virus 2 Capsid Proteins Affect Viral Infectivity: Lack of an RGD Integrin-Binding Motif," J Gen Virol. 75(12):3385-92. (1994).
GenBank Accession No. AH009962, Hamster parvovirus, retrieved on Feb. 26, 2018 from www.ncbui.nlm.nih.gov/nuccore/AH009962, modified Aug. 25, 2016. (1 page).
Shi, S. et al., "Production of Recombinant AAV Vectors Encoding Insulin-Like Growth Factor I is Enhanced by Interaction Among AAV rep Regulatory Sequences," Virol J. 6(3). (2009). (11 pages).
GenBank Accession No. NC001540, Bovine parvovirus, complete genome, retrieved on Feb. 26, 2018 from www.ncbi.nlm.nih.gov/nuccore/NC_001540, modified Nov. 30, 2009 (4 pages).
Rutledge, E. A. et al., "Infectious Clones and Vectors Derived from Adena-Associated Virus (AAV) Serotypes Other Whan AAV Type 2," J Virol. 72(1):309-19. (1998).
Xiao, W. et al., "Gene Therapy Vectors Based on Adena-Associated Virus Type 1," J Virol. 73(5):3994-4003. (1999).
GenBank Accession No. AF028705, Adena-associated virus 3B, complete genome, retrieved on Feb. 26, 2018 from www.ncbi.nlm.nih.gov/nuccore/AF028705, modified Jan. 12, 1998 (3 pages).
GenBank Accession No. U89790, Adeno-associated virus 4, complete genome, retrieved on Feb. 26, 2018 from www.ncbi.nlm.nih.gov/nuccore/U89790, modified Aug. 21, 1997 (3 pages).
GenBank Accession No. AF288061, Hamster parvovirus 5' terminal hairpin gene sequence, retrieved on Feb. 26, 2018 from www.ncbi.nlm.nih.gov/nuccore/AF288061.1?report=genbank, modified Apr. 13, 2001 (1 page).
Chen, J. et al., "Expression of Rat Bone Sialoprotein Promoter in Transgenic Mice," J Bone Miner Res. 11(5): 654-64. (1996). (12 pages).
Bantel-Schaal, U. et al., "Human Adena-Associated Virus Type 5 Is Only Distantly Related to Other Known primate Helper-Dependent Parvoviruses," J Virol. 73(2): 939-47. (1999).
GenBank Accession No. AY631966, Adeno-associated virus 11 nonstructural protein and capsid protein genes, complete eds, retrieved on Feb. 26, 2018 from www.ncbi.nlm.nih.gov/nuccore/AY631966, modified Nov. 30, 2004 (2 pages).
GenBank Accession No. AF028704, Adena-associated virus 6, complete genome, retrieved on Feb. 26, 2018 from www.ncbi.nlm.nih.gov/nuccore/AF028704, modified Jan. 12, 1998 (3 pages).
Muzyczka, N. et al., Chapter 69: Parvoviridae: The Viruses and Their Replication. *Fields Virology*, vol. 2, Fourth Edition. Lippincott-Raven Publishers, pp. 2327-2359 (2001).
Chiorini, J.A. et al., "Adena-Associated Virus (AAV) Type 5 Rep Protein Cleaves a Unique Terminal Resolution Site Compared with other AA V Serotypes," J Virol. 73(5): 4293-8. (1999).
GenBank Accession No. EU285562, Adena-associated virus 13 nonstructural protein and capsid protein genes, complete cds, retrieved Feb. 26, 2018 from www.ncbi.nlm.nih.gov/nuccore/EU285562, modified Sep. 23, 2008 (2 pages).
GenBank Accession No. NC006261, Adena-associated virus-8, complete genome, retrieved on Feb. 26, 2018 from www.ncbi.nlm.nih.gov/nuccore/NC_006261, modified Mar. 11, 2010 (3 pages).
GenBank Accession No. NC001358, Parvovirus H1, complete genome, retrieved on Feb. 26, 2018 from www.ncbi.nlm.nih.gov/nuccore/NC_001358.1?report=genbank, modified Feb. 10, 2015 (3 pages).
Gao, G. et al. "Glades of Adeno-Associated Virus Are Widely Disseminated in Human Tissues," J Virol. 78(12): 6381-8. (2004).
GenBank Accession No. AY028226, B19 virus isolate patient_A.2.1 genomic sequence, retrieved on Feb. 26, 2018 from www.ncbi.nlm.nih.gov/nuccore/AY028226, modified Apr. 16, 2001 (1 page).
GenBank Accession No. NC_002077, Adena-associated virus-1, complete genome, retrieved on Feb. 26, 2018 from www.ncbi.nlm.nih.gov/nuccore/NC_002077, modified Mar. 11, 2010 (3 pages).
Miyatake, S. et al. "Transcriptional targeting of herpes simplex virus for cell-specific replication," J Virol. 71(7): 5124-32. (1997).

Li, X. el al., "Synthetic Muscle Promoters: Activities Exceeding Naturally Occurring Regulatory Sequences," Nat Biotechnol. (17)3:241-5. (1999).
GenBank Accession No. AX753250, Sequence 5 from Patent EP1310571, retrieved on Feb. 26, 2018 from www.ncbi.nlm.nih.gov/nuccore/AX753250, modified Jun. 23, 2003 (2 pages).
GenBank Accession No. NC006152, Adena-associated virus 5, complete genome, retrieved on Feb. 26, 2018 from www.ncbi.nlm.nih.gov/nuccore/NC_006152, modified Dec. 8, 2008 (3 pages).
Piccioli, P. et al., "Neuroantibodies: Molecular Cloning of a Monoclonal Antibody Against Substance P for Expression in the Central Nervous System," Proc. Natl. Acad. Sci. USA. 88(13):5611-5. (1991).
Okuyama, T. et al., "Liver-Directed Gene Therapy: A Retroviral Vector with a Complete LTR and the ApoE Enhancer apha1-Antitrypsin Promoter Dramatically Increases Expression of Human alpha1-Antitrypsin In Vivo," Hum Gene Ther. 7(5):637-45. (1996).
GenBank Accession No. AF063497, Adeno-associated virus 1, complete genome, retrieved on Feb. 26, 2018 from www.ncbi.nlm.nih.gov/nuccore/AF063497, modified Apr. 27, 1999 (3 pages).
GenBank Accession No. NC_001729, Adeno-associated virus-3, complete genome, retrieved on Feb. 26, 2018 from www.ncbi.nlm.nih.gov/nuccore/9628918, modified Jun. 28, 2010 (3 pages).
GenBank Accession No. NC_001829, Adeno-associated virus-4, complete genome, retrieved on Feb. 26, 2018 from www.ncbi.nlm.nih.gov/nuccore/NC_001829, modified Jan. 28, 2010 (3 pages).
GenBank Accession No. AF043303, Adena-associated virus 2, complete genome, retrieved on Feb. 26, 2018 from www.ncbi.nlm.nih.gov/nuccore/AF043303, modified May 20, 2010 (5 pages).
GenBank Accession No. NC_001401, Adena-associated virus-2, complete genome, Retrieved on Feb. 26, 2018 from www.ncbi.nlm.nih.gov/nuccore/110645916 Modified Dec. 2, 2014 (7 pages).
GenBank Accession No. X01457, Parvovirus h-1, complete genome, retrieved on Feb. 26, 2018 from www.ncbi.nlm.nih.gov/nuccore/X01457, modified Apr. 18, 2005 (3 pages).
Arbuthnot, P. B. et al., "In Vitro and In Vivo Hepatoma Cell-Specific Expression of a Gene Transferred with an Menoviral Vector," Hum Gene Ther. 7(13): 1503-14 (1996).
Boshart, M. et al. "A Very Strong Enhancer Is Located Upstream of an Immediate Early Gene of Human Cytomegalovirus," Cell. 41(2): 521-30 (1985).
Chiorini, J. et al., "Cloning of Adeno-Associated Virus Type 4 (AAV4) and Generation of Recombinant AAV4 particles," J Virol. 71(9):6823-33 (1997).
GenBank Accession No. J01901, Adena-associated virus 2, complete genome, retrieved on Feb. 26, 2018 from www.ncbi.nlm.nih.gov/nuccore/J01901, modified Apr. 27, 1993 (3 pages).
Gao, G. et al., "Novel Adeno-Associated Virus from Rhesus Monkeys as Vectors for Human Gene Therapy," Proc Natl Acad Sci U S A. (9918):11854-9 (2002).
Hansal, S. et al., "Cutting Edge: Induction of Antigen-Specific Hyporesponsiveness by Transplantation of Hemopoietic Cells Containing an MHC Class I Transgene Regulated by a Lymphocyte-Specific Promoter," J Immunol. 161(3):1063-8 (1998).
Kügler, S. et al., "Human Synapsin 1 Gene Promoter Confers Highly Neuron-Specific Long-Term Transgene Expression from an Adenoviral Vector in the Adult Rat Brain Depending on the Transduced Area," Gene Ther. 10(4): 337-47 (2003).
GenBank Accession No. AF513852 Adeno-associated virus 8 nonstructural protein and capsid protein genes, complete cds, retrieved on Feb. 26, 2018 from www.ncbi.nlm.nih.gov/nuccore/AF513852, modified Sep. 5, 2002 (3 pages).
Muramatsu, S. et al. "Nucleotide Sequencing and Generation of an Infectious Clone of Adeno-Associated Virus B," Virology. 221(1):208-17 (1996).
Piccioli, P. et al. "Neuroanlibodies: Ectopic Expression of a Recombinant Anti-Substance P Antibody in the Central Nervous System of Transgenic Mice," Neuron. 15(2): 373-84 (1995).
Schmidt, M. et al. "Molecular Characterization of the Heparin-Dependent Transduction Domain on the Capsid of a Novel Adeno-Associated Virus," J Virol. 82(17): 8911-6 (2008).

(56) References Cited

OTHER PUBLICATIONS

Sandig, V. et al. "HBV-Derived Promoters Direct Liver-Specific Expression of an Adenovirally Transduced LDL Receptor Gene," Gene Ther. 3(11):1002-9 (1996).

GenBank Accession No. NC-001862, Adeno-associated virus 6, complete genome, retrieved on Feb. 26, 2018 from www.ncbi.nlm.nih.gov/nuccore/NC_001862.I?report=genbank, modified Jan. 12, 2004 (3 pages).

GenBank Accession No. NC_001510, Minute virus of mice, complete genome, retrieved on Feb. 26, 2018 from www.ncbi.nlm.nih.gov/nuccore/9626993, modified on Mar. 28, 2016 (6 pages).

GenBank Accession No. NC_001701, Goose parvovirus, complete genome, retrieved on Feb. 26, 2018 from www.ncbi.nlm.nih.gov/nuccore/NC_001701, modified Jan. 28, 2010 (4 pages).

GenBank Accession No. J02275, Minute virus of mice, complete genome, retrieved on Feb. 26, 2018 from www/ncbi.nlm.nih.gov/nuccore/J02275, modified May 22, 1995 (5 pages).

GenBank Accession No. NC_001863, Adeno-associated virus 3B, complete genome, retrieved on Feb. 26, 2018 from <https://www.ncbi.nlm.nih.gov/nuccore/NC_001863.1?report=genbank>, last modified Jan. 12, 2004 (3 pages).

Gardiner-Garden et al., "CpG Islands in Vertebrate Genomes," J Mol Biol. 196(2):261-82 (1987).

GenBank Accession No. NC_000883, Human parvovirus B19, complete genome, retrieved on Feb. 26, 2018 from www.ncbi.nlm.nih.gov/nuccore/NC_000883, modified Feb. 10, 2015 (4 pages).

GenBank Accession No. AY028223, B19 virus isolate patient_A.1.1 genomic sequence, retrieved on Feb. 26, 2018 from www.ncbi.nlm.nih.gov/nuccore/AY028223 modified on Apr. 16, 2001 (1 page).

Andersen, J.K. et al. "Herpesvirus-Mediated Gene Delivery into the Rat Brain: Specificity and Efficiency of the Neuron-Specific Enolase Promoter," Cell Mol Neurobiol. 13(5):503-15 (1993).

Stein, G. S. et al. "The Osteocalcin Gene: A Model for Multiple Parameters of Skeletal-Specific Transcriptional Control," Mol Biol Rep. 24(3):185-96 (1997).

Mori, S. et al., "Two Novel Adeno-Associated Viruses form Cynomolgus Monkey: Pseudotyping Characterization of Capsid Protein," Virology. 330(2): 375-83 (2004).

GenBank Accession No. AY530579, Adeno-associated virus 9 isolate hu.14 capsid protein VP1 (cap) gene, complete cds, retrieved on Feb. 26, 2018 from www.ncbi.nlm.nih.gov/nuccore/AY530579, modified Jun. 24, 2004 (2 pages).

Fisher, K. et al., "Transduction with Recombinant Adeno-Associated Virus for Gene Therapy Is Limited by Leading-Strand Synthesis," J Virol. 71(1):520-32 (1996).

Srivastava, A. et al. "Nucleotide Sequence and Organization of the Adeno-Associated Virus 2 Genome," J Virol. 45(2):555-64 (1983).

Shade, R. O. et al. "Nucleotide Sequence and Genome Organization of Human Parvovirus 819 Isolated from the Serum of a Child during Aplastic Crisis," J Virol. 58(3): 921-36 (1986).

GenBank Accession No. AF513851, Adeno-associated virus 7 nonstructural protein and capsid protein genes, complete cds, retrieved on Feb. 26, 2018 from www.ncbi.nlm.nih.gov/nuccore/AF513851, modified Sep. 5, 2002 (3 pages).

* cited by examiner

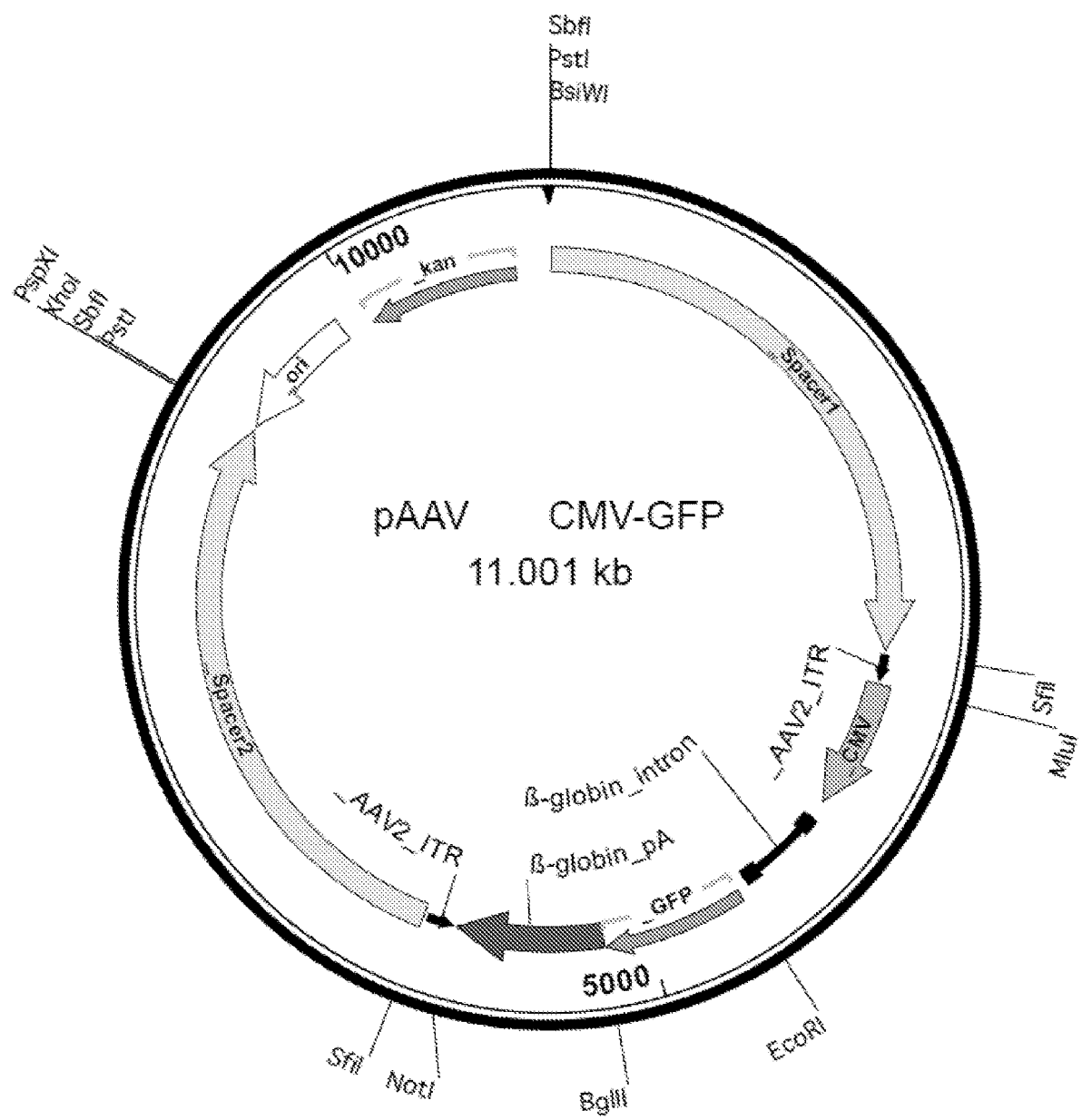

SEQUENCE LISTING

<160> NUMBER OF SEQ ID NOS: 12

<210> SEQ ID NO 1
<211> LENGTH: 3000
<212> TYPE: DNA
<213> ORGANISM: Homo sapiens

<400> SEQUENCE: 1

```
gtaaaaaaag gcatagctaa caaggtgtgg aaaaagaatt agtggttaga gagtgagcta        60
ttcgttgaaa caattgcgtt cttgaaacaa ttcttgctgg taaaatgtca cattttatgt       120
gactacaggt ggaggattgg cacataacct aaccagtggg ggaaacaatt gacctctgga       180
tttgtccaag tgtatagtag catttgccca atcgaatggt cctggtaagg tgttaatgtt       240
gactagaacc aaaggtggaa gttgcaggga aactggttta gtacaagggt ggacaccagg       300
cagtcatcca gaggcccatt aaaggccttg gaatgttttt ccgaaggaga atcactccct       360
cttctctcgc ttaaagtttt aggggattca tgaacagctg ctgtgggata gtttcatgtc       420
cctagcaatt gtaaagcaac tgagggtggc ttaaaccagt tttagcttta gggttaggggt       480 tactggacta aaatttgaga aattcataaa tcttaaggaa atccattgtg agttttcatt       540
```

```
atgagtgcat ccaatgtata atttccatga ccctcccatg caagtgagca tgtgaatcag    600
gaaacgttac aagaacccaa caaactcaac cactactaga caggcgatca cttccagtta    660
gtatgcaact ttctgtgtaa ttttagttac cattaaaatc tggatgacct tagtgtaagg    720
aaaaaatacc ttgaatagtg ttaaagatgt acacttggtg tcaggcattg taacattgat    780
aaatctgtgt aaggtgcttt ttgaaaactt caaagctgca tcaagtcaag tacaagaaag    840
gccatggctg ctaaagctgt tgaagatgtg ggatggaact gggtcacatt ggtgttaaca    900
gcgttgtgca gagccggcag gatcttggtg tgagcgaaca ttagtctatt taataaagct    960
gtgtgaatgt tgtagaggtg aggatgctca cttgaaaact cactgaagaa cacttggccc   1020
cttgaactaa agtgcttcta tcaagttcag tgagaaattc cgaattacaa gcataggtac   1080
tagaaaagtt ttgaaaagca gtatagagca acataagcac attcataaaa ttagtgatgt   1140
agaaagtgaa atttccacgt atggtcactc ccagagaaaa aaaatacgtt tatttacctt   1200
ttttaaaaat aggggatttc aggccgggtg aggtggctca cgcctgtaat cccagcactt   1260
tgggaggccc aggtgggcgg atcacctgag gtcaggagtt ggaggatgg caaatcccat   1320 ctctacaaaa tatacaaaaa aatagctggg tgtgttggca ggcgcctgta atcccagcta   1380
ctcggaaggc tgaggcagga gaatccctgg aaccagggat gtggaggttg cagtgagccg   1440
agattgtgta actgcattcc agcctgggca acaagagcaa gactccgtat caggaaaaaa   1500
aaaagggggg gttggatttc gcttgttgca taggttggtc tcaaactcct ggcctcaagt   1560
gattctcctg cctctgcctc ccaaagtgct gagattacag gtgtgaggca ccatgccagg   1620
tctcttactg tttgtaatta aatacataca cattttgtgt gtttgtgtgc acctttataa   1680
agtcaaaggt gatagtaacc catttaagtt cctactcaat tttactttcc agggataact   1740 aactacttt tcttttttgag atggagtctc gctgtgtagc ccaggctgga gtgcagtggc   1800
accatctcgg ctcactgcaa gctcctcctc cctggttcac gctattctcc tgcctcagcc   1860
tccccaacaa ctaggactac aggctcacct cgccatacct ggctaatttt ttgtattttt   1920
agtagagaca gggtttcact gtgttagcca ggatggtctc gatctcctga ccttgtgatc   1980
cgcctgcctc tgcctcccaa agtgctggga ttacaggcat gagcaacctc acccagctgg   2040
gataactact ttttacaggt tgatattctt ttggactttt cccctgtgta aaaatatact   2100
atatttgtta tgtacatatt atgtacatac agacacaaat tggaccattc tcagtataat   2160
gattctcagg ttttttttt tttttgagg tggggaacta gataattatg gacatctttc   2220
catactagca tatcaatatc tacctcattc tttttaatat tttgctagt attccattgt   2280 atgaatgtcc tatgatttac ttaacctgtc catcaatatt tgtttccagg tttttgctat   2340
tataatgctg ctgcaaagta catcctcaca catctttatt ttgtctattc atatttctgt   2400
aagataggtt actaaagttg gaactgccaa attaacacta tcatactatt ttgtttttta   2460
attttaattt tttaaaaaat gtaaaatgtg caatttcaag aggagaaact tgaacacaag   2520
gagcaaaatc tattttttata acatcctatt aaaagcttgc tttacataaa gattttgaaa   2580
gaatagcata aatacaagat ttctatttta attggattct tagggctaat aaaataatca   2640
gccttagcac ttatttattt atttttttg agagggagtc tcgctctgtt gtccatgctg   2700
gagtgcagtg gcgtgatctc ggctcactgc aagctccacc tcatgagttc acaccattct   2760
cctgcctcag tctcccgagt agctgggact ccaggcgccc tctacaaagc ccgtctaatt   2820 tttttgtat ttttagtaga cagggttt cactgtgtta gccaggatgg tcttgatctc   2880
ctgaccttgt gatctgcccg cctcggcctc ccaaagtgct gggattatag gcttgagcca   2940
```

| | | | | |
|---|---|---|---|---|
| ctgctcccgg | ccagcactta | tttttataat | tcttcatgat | tactgtgtta ctgtcccatg | 3000 |

<210> SEQ ID NO 2
<211> LENGTH: 2884
<212> TYPE: DNA
<213> ORGANISM: Homo sapiens

<400> SEQUENCE: 2

| | | | | | |
|---|---|---|---|---|---|
| atatttctca | attttttaaat | ttttcaaaaa | aattaatcct | taatgtgcat | attttttgaat | 60 |
| tgttaatata | acttttttgag | gtgatgtctt | catgtgtttc | aactacttaa | aaactttttaa | 120 |
| acagtatata | ataaaaaatc | ttccaggcca | ctcacacctg | taatcccagc | actttgggag | 180 |
| gctgaggtgg | gcagatcacc | tgagggcagg | agttcgagac | cagcctggcc | aatatatata | 240 |
| tattcatata | ttcatatata | tatatatatt | catatattca | tatatatata | ttcatatatt | 300 |
| catatatata | tatatatata | tatatagcaa | aacctcatct | ctaataaaat | acaaaaatta | 360 |
| gctgagcgtg | gtgatggatg | cctgtagtcc | cagctactcg | ggaggctgag | gcaggagaat | 420 |
| ctcttgaacc | tgggaggtgg | aggttgcagt | gagctgagat | ggtgccactg | ccctccagcc | 480 |
| tgagtgacag | agcgagactc | ggtctccaaa | aaaaaacaac | aaaaaaatct | tccatccttg | 540 |
| tctcccatcc | accccttccc | cccagcatgt | acttgcagac | tttatgcata | tacagtgagt | 600 |
| actgtatata | cacaaataat | aaaaaaatca | tatatataat | atatgtaatt | cccctttaca | 660 |
| tgaaaggtag | cacactggtc | tgtacagtct | gtctgcactg | tgctatttca | ctttatattt | 720 |
| ttatagtttg | acagagttct | aacatttctt | tttttttttt | tttaacagag | tcttgttcct | 780 |
| gattgttaaa | tttttaaagca | tcctaaagtt | tggtttcaca | cttgaatgaa | taccatgtaa | 840 |
| ggattcactt | acatagatgt | ggttgcctga | atcttaagaa | taaaataaca | ttgtttgtat | 900 |
| ttatttaaat | tagtgttcct | tttatggttt | gcctgaaagc | acaacaaaat | cctcaccaag | 960 |
| atattacaat | tatgactccc | atacaggtaa | actgttaga | gattggcaag | cacccttttaa | 1020 |
| tgaaaggagt | cagccagctt | agtgtgcagt | atttatttct | gccggaagag | ggagcttcag | 1080 |
| ggacagactt | tggtttagtc | atgaagcctc | cagcactccc | aagcggttgt | ggttgaccaa | 1140 |
| gcaatttatg | cttttacctt | tctacttcca | gaggcttgtt | tacttatcag | taagcattaa | 1200 |
| tttagtgtcc | cctcagatgc | cttttacttt | cttcttttct | gcctagaata | agctgctctt | 1260 |
| ccaattttgc | agctacatgt | ttccacccca | gttggaattt | ctccataaca | tccattgtag | 1320 |
| ctatccttca | atctacagcc | tctatttcct | gttatagctg | gtcaggtcta | atccctcaaa | 1380 |
| atactctgtc | ccctgcttcc | cttatctgct | ggccaccttt | ttcccccaca | tacacactgc | 1440 |
| catgtcccac | ccttcactca | agttgttccc | tgccacctca | acaaatttaa | gtccataaaa | 1500 |
| tagagtaagt | gttcctgact | gttaaatttt | aaagcatccc | aaagtctgat | ttcacactcg | 1560 |
| aatgaatact | atgtacggat | tcatttacat | agatgcggtt | gcatgagtct | taacaaaaaa | 1620 |
| ataacattat | ttgtatttat | tcaaagtact | gtcaagatat | aatgtcaaga | cctaattcaa | 1680 |
| aggttccaca | aagccttcct | tgactgcccc | caacgaagat | tatccatttt | ccctgaaatc | 1740 |
| ccattgactt | ttctattttg | taaggaggct | cgtgagactc | tgtctaaaaa | caaaacaaaa | 1800 |
| caaaagaaa | caatcaaacg | gcttgcttct | gttctttgat | ctgctagtaa | gcaaaaatta | 1860 |
| cacatggtga | caggagctat | gtgaggctgt | caggttgaat | gggaggagtt | tgggatcctg | 1920 |
| cttgtggatg | gttggaagag | gctttcggga | aagacagtat | ttatgtgaga | cctgaagat | 1980 |
| gggccttagc | tttgcagaag | gtggagaggc | aggaaatagc | acgggggccc | tggggctgga | 2040 |

-continued

| agacttgggc ataTTTgagg aacagaaagg agaccagcat aactgaggtg ggaaaagcat | 2100 |
| gtgaagagat ggggctggag gaggccggga gtggtggctc acgcctgtaa tcccagcact | 2160 |
| tgggaggcc aaggcaggcg gatcatgagc tcaggagatt gagaccatcc tggctaacac | 2220 |
| ggtgaaaccc cctctctact aaaaatacaa aaaaaaaaaa aaaaaaaatt agctgggcgt | 2280 |
| ggtggcagga gcctgtagtc ccagctacct gggaggctga ggcaggagaa tggcgtgaac | 2340 |
| ctggaaggct gagcttgcag tgagccgaga ttgcaccact gcactccagc ctgggagaca | 2400 |
| gagagagact ccctctcaaa aaaacaaaca aacgaaacaa aacaaaacaa aaattagcca | 2460 |
| ggcgtggtgg tatgcacctg taatcccagc tactcgggag gttgaggcag gagaaacgct | 2520 |
| tgaactcagg aggcggaggt tgcagtgagc cgagactgcg ccactgcact ccagcctcaa | 2580 |
| cctcccagc tgaagccatc tcttgcctc agcctcctaa gtagctggga ctacaggcgc | 2640 |
| gcacctccag gcttggctct tattctttt attgttttg aaactataga acctattttt | 2700 |
| aaaaaatgtt ttggttgttt ttattgctgc ttttcctttt ggggttagaa cacaagtttt | 2760 |
| gatgggaaac aggttagaac acattcatct cttcccatag cgatggtcat agaaaaacgg | 2820 |
| ggcatattta taaactctca gttgatctta aaatgtgcaa aagctgccga actcctggga | 2880 |
| gtga | 2884 |

<210> SEQ ID NO 3
<211> LENGTH: 1501
<212> TYPE: DNA
<213> ORGANISM: Homo sapiens

<400> SEQUENCE: 3

| gaaaaggggg ggttggattt cgcttgttgc ataggttggt ctcaaactcc tggcctcaag | 60 |
| tgattctcct gcctctgcct cccaaagtgc tgagattaca ggtgtgaggc accatgccag | 120 |
| gtctcttact gtttgtaatt aaatacatac acattttgtg tgtttgtgtg cacctttata | 180 |
| aagtcaaagg tgatagtaac ccatttaagt tcctactcaa ttttactttc cagggataac | 240 |
| taactacttt ttctttttga gatggagtct cgctgtgtag cccaggctgg agtgcagtgg | 300 |
| caccatctcg gctcactgca agctcctcct ccctggttca cgctattctc ctgcctcagc | 360 |
| ctccccaaca actaggacta caggctcacc tcgccatacc tggctaattt tttgtatttt | 420 |
| tagtagagac agggtttcac tgtgttagcc aggatggtct cgatctcctg accttgtgat | 480 |
| ccgcctgcct ctgcctccca agtgctggg attacaggca tgagcaacct cacccagctg | 540 |
| ggataactac tttttacagg ttgatattct tttggacttt tcccctgtgt aaaaatatac | 600 |
| tatatttgtt atgtacatat tatgtacata cagacacaaa ttggaccatt tcagtataa | 660 |
| tgattctcag gttttttttt ttttttgag gtggggaact agataattat ggacatcttt | 720 |
| ccatactagc atatcaatat ctacctcatt ctttttaata tttttgctag tattccattg | 780 |
| tatgaatgtc ctatgattta cttaacctgt ccatcaatat ttgtttccag ttttttgcta | 840 |
| ttataatgct gctgcaaagt acatcctcac acatctttat tttgtctatt catatttctg | 900 |
| taagataggt tactaaagtt ggaactgcca aattaacact atcatactat tttgttttt | 960 |
| aattttaatt ttttaaaaaa tgtaaaatgt gcaattcaa gaggagaaac ttgaacacaa | 1020 |
| ggagcaaaat ctatttttat aacatcctat taaaagcttg ctttacataa agattttgaa | 1080 |
| agaatagcat aaaatcaaga tttctatttt aattggattc ttagggctaa taaaataatc | 1140 |
| agccttagca cttattttatt tattttttt gagagggagt ctcgctctgt tgtccatgct | 1200 |
| ggagtgcagt ggcgtgatct cggctcactg caagctccac ctcatgagtt cacaccattc | 1260 |

| | | | | |
|---|---|---|---|---|
| tcctgcctca gtctcccgag tagctgggac tccaggcgcc ctctacaaag cccgtctaat | 1320 |
| tttttttgta ttttttagtag agacaggggt tcactgtgtt agccaggatg gtcttgatct | 1380 |
| cctgaccttg tgatctgccc gcctcggcct cccaaagtgc tgggattata ggcttgagcc | 1440 |
| actgctcccg gccagcactt attttttataa ttcttcatga ttactgtgtt actgtcccat | 1500 |
| g | 1501 |

<210> SEQ ID NO 4
<211> LENGTH: 1501
<212> TYPE: DNA
<213> ORGANISM: Homo sapiens

<400> SEQUENCE: 4

| | |
|---|---|
| atatttctca atttttaaat ttttcaaaaa aattaatcct taatgtgcat attttttgaat | 60 |
| tgttaatata acttttttgag gtgatgtctt catgtgtttc aactacttaa aaacttttaa | 120 |
| acagtatata ataaaaaatc ttccaggcca ctcacacctg taatcccagc actttgggag | 180 |
| gctgaggtgg gcagatcacc tgagggcagg agttcgagac cagcctggcc aatatatata | 240 |
| tattcatata ttcatatata tatatatatt catatattca tatatatata ttcatatatt | 300 |
| catatatata tatatatata tatatagcaa aacctcatct ctaataaaat acaaaaatta | 360 |
| gctgagcgtg gtgatggatg cctgtagtcc cagctactcg ggaggctgag gcaggagaat | 420 |
| ctcttgaacc tgggaggtgg aggttgcagt gagctgagat ggtgccactg ccctccagcc | 480 |
| tgagtgacag agcgagactc ggtctccaaa aaaaaacaac aaaaaaatct tccatccttg | 540 |
| tctcccatcc accccttccc cccagcatgt acttgcagac tttatgcata tacagtgagt | 600 |
| actgtatata cacaaataat aaaaaaatca tatatataat atatgtaatt ccccttttaca | 660 |
| tgaaaggtag cacactggtc tgtacagtct gtctgcactg tgctatttca ctttatattt | 720 |
| ttatagtttg acagagttct aacatttctt ttttttttttt tttaacagag tcttgttcct | 780 |
| gattgttaaa ttttaaagca tcctaaagtt tggtttcaca cttgaatgaa taccatgtaa | 840 |
| ggattcactt acatagatgt ggttgcctga atcttaagaa taaaataaca ttgtttgtat | 900 |
| ttatttaaat tagtgttcct tttatggttt gcctgaaagc acaacaaaat cctcaccaag | 960 |
| atattacaat tatgactccc atacaggtaa actgtttaga gattggcaag caccttttaa | 1020 |
| tgaaaggagt cagccagctt agtgtgcagt atttatttct gccggaagag ggagcttcag | 1080 |
| ggacagactt tggtttagtc atgaagcctc cagcactccc aagcggttgt ggttgaccaa | 1140 |
| gcaatttatg cttttacctt tctacttcca gaggcttgtt tacttatcag taagcattaa | 1200 |
| tttagtgtcc cctcagatgc cttttacttt cttctttttct gcctagaata agctgctctt | 1260 |
| ccaattttgc agctacatgt ttccacccca gttggaattt ctccataaca tccattgtag | 1320 |
| ctatccttca atctacagcc tctatttcct gttatagctg gtcaggtcta atccctcaaa | 1380 |
| atactctgtc ccctgcttcc cttatctgct ggccaccttt ttcccccaca tacacactgc | 1440 |
| catgtcccac ccttcactca agttgttccc tgccacctca acaaatttaa gtccataaaa | 1500 |
| c | 1501 |

<210> SEQ ID NO 5
<211> LENGTH: 14
<212> TYPE: DNA
<213> ORGANISM: Homo sapiens

<400> SEQUENCE: 5
gagcgagcga gcgc                                                          14

<210> SEQ ID NO 6
<211> LENGTH: 6015
<212> TYPE: DNA
<213> ORGANISM: Homo sapiens

<400> SEQUENCE: 6

| | | | | | |
|---|---|---|---|---|---|
| gagggtttca | gcgctaaaac | taggctgtcc | tgggcaaaca | gcataagctg | gtcacccac | 60 |
| acccagacct | gacccaaacc | cagctcccct | gcttcttggc | cacgtaacct | gagaagggaa | 120 |
| tccctcctct | ctgaaccca | gcccacccca | atgctccagg | cctcctggga | taccccgaag | 180 |
| agtgagtttg | ccaagcagtc | accccacagt | tggaggagaa | tccacccaaa | aggcagcctg | 240 |
| gtagacaggg | ctggggtggc | ctctcgtggg | gtccaggcca | agtaggtggc | ctggggcctc | 300 |
| tgggggatgc | agggaaggg | ggatgcaggg | gaacggggat | gcaggggaac | ggggctcagt | 360 |
| ctgaagagca | gagccaggaa | ccctgtagg | gaaggggcag | gagagccagg | ggcatgagat | 420 |
| ggtggacgag | gaaggggac | agggaagcct | gagcgcctct | cctgggcttg | ccaaggactc | 480 |
| aaacccagaa | gcccagagca | gggccttagg | gaagcgggac | cctgctctgg | gcggaggaat | 540 |
| atgtcccaga | tagcactggg | gactcttta | ggaaagaagg | atggagaaag | agaaggga | 600 |
| tagaggcggc | cacgacctgg | tgaacaccta | ggacgcacca | ttctcacaaa | gggagttttc | 660 |
| cacacggaca | ccccctcct | caccacagcc | ctgccaggac | ggggctggct | actggcctta | 720 |
| tctcacaggt | aaaactgacg | cacggaggaa | caatataaat | tggggactag | aaaggtgaag | 780 |
| agccaaagtt | agaactcagg | accaacttat | tctgattttg | tttttccaaa | ctgcttctcc | 840 |
| tcttgggaag | tgtaaggaag | ctgcagcacc | aggatcagtg | aaacgcacca | gacagccgcg | 900 |
| tcagagcagc | tcaggttctg | ggagagggta | gcgcagggtg | gccactgaga | accgggcagg | 960 |
| tcacgcatcc | ccccttccc | tcccacccc | tgccaagctc | tccctcccag | gatcctctct | 1020 |
| ggctccatcg | taagcaaacc | ttagaggttc | tggcaaggag | agatggct | ccaggaaatg | 1080 |
| ggggtgtgtc | accagataag | gaatctgcct | aacaggaggt | gggggttaga | cccaatatca | 1140 |
| ggagactagaa | aaggaggagg | cctaaggatg | gggcttttct | gtcaccaatc | ctgtccctag | 1200 |
| tggccccact | gtgggtgga | ggggacagat | aaaagtaccc | agaaccagag | ccacattaac | 1260 |
| cggccctggg | aatataaggt | ggtcccagct | cggggacaca | ggatccctgg | aggcagcaaa | 1320 |
| catgctgtcc | tgaagtggac | atagggccc | gggttggagg | aagaagacta | gctgagctct | 1380 |
| cggacccctg | gaagatgcca | tgacaggggg | ctggaagagc | tagcacagac | tagagaggta | 1440 |
| agggggtag | gggagctgcc | caaatgaaag | gagtgagagg | tgacccgaat | ccacaggaga | 1500 |
| acggggtgtc | caggcaaaga | aagcaagagg | atggagaggt | ggctaaagcc | agggagacgg | 1560 |
| ggtactttgg | ggttgtccag | aaaaacggtg | atgatgcagg | cctacaagaa | ggggaggcgg | 1620 |
| gacgcaaggg | agacatccgt | cggagaaggc | catcctaaga | aacgagagat | ggcacaggcc | 1680 |
| ccagaaggag | aaggaaaagg | gaacccagcg | agtgaagacg | gcatggggtt | gggtgaggga | 1740 |
| ggagagatgc | ccggagagga | cccagacacg | ggaggatcc | gctcagagga | catcacgtgg | 1800 |
| tgcagcgccg | agaaggaagt | gctccggaaa | gagcatcctt | gggcagcaac | acagcagaga | 1860 |
| gcaaggggaa | gagggagtgg | aggaagacgg | aacctgaagg | aggcggcagg | gaaggatctg | 1920 |
| ggccagccgt | agaggtgacc | caggccacaa | gctgcagaca | gaaagcggca | caggcccagg | 1980 |
| ggagagaatg | caggtcagag | aaagcaggac | ctgcctggga | aggggaaaca | gtgggccaga | 2040 |
| ggcggcgcag | aagccagtag | agctcaaagt | ggtccggact | caggagagag | acggcagcgt | 2100 |

```
tagagggcag agttccggcg gcacagcaag ggcactcggg ggcgagagga gggcagcgca    2160
aagtgacaat ggccagggcc aggcagatag accagactga gctatgggag ctggctcagg    2220
ttcaggagag ggcagggcag ggaaggagac aaagtccagg accggctgga ggggctcaac    2280
atcggaagag gggaagtcga gggagggatg gtaaggagga ctgcatgggt cagcacaggc    2340
tgccaaagcc agggccagtt aaagcgactc caatgcggaa gagagtaggt cgaaggggaa    2400
tggtaaggag gcctggggca gagtggtcag cacagagtgg ctaagcccag gccagttga    2460 agcggctcca attcggaagt ggggtggtcg aaggggaatg gtaaggggga ctgggacggg    2520
gtgtcagcat agggtggcaa agcccagggc caggaacgac ggggcggatc gagactggca    2580
acggggaagg aggatgcccc aggtggcgca gcagagggtg gacctggccc cgggagacgc    2640
cgggcggggg gcgctgacct ggtgcagggc gctgataccg tcggcgttgg tggagtccag    2700
cacggcgcgg gcgggcggcg gcgcggcggg gtcgagctcg gcgccggggc cagggtcggc    2760
ggcgcgcagc atcagacgcg cctcgtccag gtcgccgccc gcacaggccg ccaggaactc    2820
ggcggcgcgc tcgaagcgga cggtgcgggc gcggcgctct ccggggccag gctcggcgcc    2880
cgcccgcgcc ccccactgcc gcagctgctc ccgtcgccgc tcccgggcag ccgccgccgc    2940
cgcccccggg ccagccgccg ggccatcctc tccggacatc gcaccgcccg cccgcccagc    3000
gagcgagcga gcgccgagcc ccaaccgccg ccaccacccg cccgcccgcc cgccccgggg    3060
gccgccggga actgccgctg gccccccacc gccccaagga tctcccggtc cccgcccggc    3120
gtgctgacgt cacggcgctg cccccagggtg tgctgggcag gtcgcgggga gcgctgggaa    3180
atggagtcca ttagcagaag tggcccttgg ccacttccag gagtcgctgt gccccgatgc    3240
acactgggaa gtccgcagct ccgaggcgcc cagtggaaat cgccagatga gggcctcctc    3300
cggggaatgc tgggaaatgg agtctacagg ccggaggggt gccccacggc atactaggaa    3360
gtgtgtagca ccgggtaaag gggatgaata gcagactgcc ccggggcagt taggaattcg    3420
actggacagc cgcgtgggag ggagtgcggg gagaggcaga gttgttttgt tattgttgtt    3480
ttattttgtt ttctttgttt tgagacggag tctcgctctg tcgccacgct ggagttcagt    3540
ggcgcgatat cggctcgctg caacctccgc ttcccaggtt caagcaattc tggctcagtc    3600
cccagagtag ctgggataac aggcgcgcgc caccccgccc tgctaatttt tatattttta    3660
gtagagacgg gatttcacca tgttggccat gatggtcttg atctcttgac ctcatgatcc    3720
gcccgcctcg gcctgtaatc ctgctgggat gacgagcgta agccaccatg cccagctggg    3780
ttttatttat tttggttttt ttcctgaccc cttaactaga aataagctcc acgagagcgg    3840 gatctttttgt cttctgtgca ctacttgtcc tcggttctta gaacagaacc tgagagaacc    3900
tgatcgcaaa tattttttgga atgaatgaat gaatgggttc accagggcac catgggaaac    3960
tgagtccgca acctagaagc catgaaagac agtccacttc caagcttccc tgggtgacct    4020
cgcagggcat gctgggaaat gaaatttgcg gtgaaaaggt caggaccacg atcctagggc    4080
acgctgggaa atgtagccca cagggccaca cccctaaaag cacagtgggg tgcaaggcag    4140 ggcccccaagg catttaggcc tcggggcaag agaaatccac actccactcc ctaatggtaa    4200
tccctgagcc acaccgagta aaggaaccca agacacagtg tccacaggga cagggctctc    4260
agagctttca ctggcccgcg cttctcctgc gcccacccgg acctcctggg aaccgcccag    4320
gccctcgcgc gctctcaagg catgctggga ttggtggtcc cggcaagga gttccagcag    4380 gtggggggcg aatcaccttt cagcgggccc aagcgatgag cacaccttga tcttcacctt    4440
```

```
acggatcccg cgcccaactc aagattggga aggtggctgg cactttgtga caggaagagt    4500
cccataaaaa tcatacagaa aagggccaaa atcgggacag agactacaga ctgtttccca    4560
agcgctgtgg gagtttccca cccactctga agtccttggg tttgcgcgga gacgtaaact    4620
gcgcatccca cgaggcctgt ttctttccct ctctctttct cttttgttgt tgttgttgct    4680
gctgctgtta cgaaaatttt tgtggtttta ttgtatcatg aggcattgaa acatccggcg    4740
actcaatgtc taggcggtga ggcagccgct ttctccttca ctttctttgg gttaagtaga    4800
gcaacttgtc agtagttttg ttttttttg ttgttgttgt tgttttgag acggaggctt    4860 gctctgtcgc ccaggctgga gtgcagtggc gcgatgtcgg ctcactgcaa gctctgcctc    4920 ccggggttcaa gcgattctcc tgcctcagcc tcctgagtag ctgggactac aggcgtgctc    4980
caccacgccc ggctaatttt tgtttttag tagagacggg gtttcaccat gttggccagg    5040
ctggtctcga attcctgacc tcgtgatccg actgcctcgg cctcccaaaa tgctgggatt    5100
acaggcgtga gccgccgcga ccggccagat ttttttttt tttaaaggac aaccttttgc    5160
attacttaag tctttccaag gcatgcgctg gtacaacaca aacttttccc attacatgca    5220
gctagtctag tgtccagacg tcatgcacaa cacctccgtg gcatcagcgc actgcgccca    5280
ctcccactgc gaccctgctc atttgtcat catatctgga ggagtggcaa tagttctgga    5340
aagaggaggg aagaggaggc agcgtgaggg cccggtggag aggaggtcag ctgaagttgt    5400
gcagagcaag cctgcatatc attggtgcaa acccaagcat cattgcatcg ctgatgtttt    5460
gttttgtttg gttttgtttt gttttgaga cggagtctca ctgtgtcgcc caggctggag    5520
tgcagtgatg tgatctcggc tcactgcaac ctccgcctcc caggttcaag tgattctcct    5580
acctcagcct cccaagtagc tgggattaca ggcgtgctcc acgcctggct aattttttgta    5640 tttttagtag agacaaggtt tcaccatgtt ggccaggctg gtctcgatct cctgacctca    5700
agtgatccac ccgcctcagc ttcccaaagt gctgggatta caggcatgag ccaccacacc    5760
cagctgatgt tctttagtag gaatatctgg tggaaccca agatgggggtc ttcatccgcc    5820 acgaagcctg tttctataga aagggatagt tctggtggct cttaggtgtg gtccctgaac    5880
cccacacttt ccacatactt acacaccaac ctccttcccc caggaaaaca agaagtcggt    5940
cttcagggtg ttaccgtgta gctctggttc tgtatgtatt ctgtgccttt atgtataatt    6000 gtgtgtatt gcaat                                                     6015

<210> SEQ ID NO 7
<211> LENGTH: 3000
<212> TYPE: DNA
<213> ORGANISM: Homo sapiens

<400> SEQUENCE: 7
catgggacag taacacagta atcatgaaga attataaaaa taagtgctgg ccgggagcag      60
tggctcaagc ctataatccc agcactttgg gaggccgagg cgggcagatc acaaggtcag     120
gagatcaaga ccatcctggc taacacagtg aaaccctgtc tctactaaaa atacaaaaaa     180
aattagacgg gctttgtaga gggcgcctgg agtcccagct actcgggaga ctgaggcagg     240
agaatggtgt gaactcatga ggtggagctt gcagtgagcc gagatcacgc cactgcactc     300
cagcatggac aacagagcga gactccctct caaaaaaaat aaataaataa gtgctaaggc     360
tgattatttt attagcccta agaatccaat taaaatagaa atcttgtatt tatgctattc     420
tttcaaaatc tttatgtaaa gcaagctttt aataggatgt tataaaaata gattttgctc     480
cttgtgttca agtttctcct cttgaaattg cacattttac attttttaaa aaattaaaat     540
```

```
taaaaaacaa aatagtatga tagtgttaat ttggcagttc caactttagt aacctatctt      600
acagaaatat gaatagacaa aataaagatg tgtgaggatg tactttgcag cagcattata      660
atagcaaaaa cctggaaaca aatattgatg acaggttaa gtaaatcata ggacattcat       720
acaatggaat actagcaaaa atattaaaaa gaatgaggta gatattgata tgctagtatg      780
gaaagatgtc cataattatc tagttcccca cctcaaaaaa aaaaaaaaaa cctgagaatc      840
attatactga gaatggtcca atttgtgtct gtatgtacat aatatgtaca taacaaatat      900
agtatatttt tacacagggg aaaagtccaa aagaatatca acctgtaaaa agtagttatc      960
ccagctgggt gaggttgctc atgcctgtaa tcccagcact ttgggaggca gaggcaggcg     1020
gatcacaagg tcaggagatc gagaccatcc tggctaacac agtgaaaccc tgtctctact     1080
aaaaatacaa aaaattagcc aggtatggcg aggtgagcct gtagtcctag ttgttgggga     1140
ggctgaggca ggagaatagc gtgaaccagg gaggaggagc ttgcagtgag ccgagatggt     1200
gccactgcac tccagcctgg gctacacagc gagactccat ctcaaaaaga aaaagtagtt     1260
agttatccct ggaaagtaaa attgagtagg aacttaaatg ggttactatc acctttgact     1320
ttataaaggt gcacacaaac acacaaaatg tgtatgtatt taattacaaa cagtaagaga     1380
cctggcatgg tgcctcacac ctgtaatctc agcactttgg gaggcagagg caggagaatc     1440
acttgaggcc aggagtttga gaccaaccta tgcaacaagc gaaatccaac ccccccttt      1500 tttttttcctg atacggagtc ttgctcttgt tgcccaggct ggaatgcagt tacacaatct     1560
cggctcactg caacctccac atccctggtt ccagggattc tcctgcctca gccttccgag     1620
tagctgggat tacaggcgcc tgccaacaca cccagctatt tttttgtata ttttgtagag     1680
atgggatttg ccatccctcc aactcctgac ctcaggtgat ccgcccacct gggcctccca     1740
aagtgctggg attacaggcg tgagccacct cacccggcct gaaatcccct atttttaaaa     1800
aaggtaaata aacgtatttt ttttctctgg gagtgaccat acgtggaaat ttcactttct     1860
acatcactaa ttttatgaat gtgcttatgt tgctctatac tgcttttcaa aacttttcta     1920
gtacctatgc ttgtaattcg gaatttctca ctgaacttga tagaagcact ttagttcaag     1980
gggccaagtg ttcttcagtg agttttcaag tgagcatcct cacctctaca acattcacac     2040
agctttatta aatagactaa tgttcgctca caccaagatc ctgccggctc tgcacaacgc     2100
tgttaacacc aatgtgaccc agttccatcc cacatcttca acagctttag cagccatggc     2160
ctttcttgta cttgacttga tgcagctttg aagttttcaa aaagcacctt acacagattt     2220
atcaatgtta caatgcctga caccaagtgt acatctttaa cactattcaa ggtatttttt     2280
ccttacacta aggtcatcca gatttttaatg gtaactaaaa ttacacagaa agttgcatac    2340
taactggaag tgatcgcctg tctagtagtg gttgagtttg ttggggttctt gtaacgtttc    2400 ctgattcaca tgctcacttg catgggaggg tcatggaaat tatacattgg atgcactcat     2460
aatgaaaact cacaatggat ttccttaaga tttatgaatt tctcaaattt tagtccagta     2520
accctaaccc taaagctaaa actggtttaa gccaccctca gttgctttac aattgctagg     2580
gacatgaaac tatcccacag cagctgttca tgaatcccct aaaactttaa gcgagagaag     2640
agggagtgat tctccttcgg aaaaacattc caaggccttt aatgggcctc tggatgactg     2700
cctggtgtcc acccttgtac taaaccagtt tccctgcaac ttccaccttt ggttctagtc     2760
aacattaaca ccttaccagg accattcgat tgggcaaatg ctactataca cttgacaaa      2820 tccagaggtc aattgtttcc cccactggtt aggttatgtg ccaatcctcc acctgtagtc     2880
```

-continued

| | |
|---|---|
| acataaaatg tgacatttta ccagcaagaa ttgtttcaag aacgcaattg tttcaacgaa | 2940 |
| tagctcactc tctaaccact aattctttt ccacaccttg ttagctatgc cttttttac | 3000 |

<210> SEQ ID NO 8
<211> LENGTH: 2884
<212> TYPE: DNA
<213> ORGANISM: Homo sapiens

<400> SEQUENCE: 8

| | |
|---|---|
| tcactcccag gagttcggca gcttttgcac attttaagat caactgagag tttataaata | 60 |
| tgccccgttt ttctatgacc atcgctatgg gaagagatga atgtgttcta acctgtttcc | 120 |
| catcaaaact tgtgttctaa ccccaaaagg aaaagcagca ataaaaacaa ccaaaacatt | 180 |
| ttttaaaaat aggttctata gtttcaaaaa caataaaaag aataagagcc aagcctggag | 240 |
| gtgcgcgcct gtagtcccag ctacttagga ggctgaggca agaggatggc ttcagctggg | 300 |
| gaggttgagg ctggagtgca gtggcgcagt ctcggctcac tgcaacctcc gcctcctgag | 360 |
| ttcaagcgtt tctcctgcct caacctcccg agtagctggg attacaggtg cataccacca | 420 |
| cgcctggcta attttgttt tgttttgttt cgtttgtttg tttttttgag agggagtctc | 480 |
| tctctgtctc ccaggctgga gtgcagtggt gcaatctcgg ctcactgcaa gctcagcctt | 540 |
| ccaggttcac gccattctcc tgcctcagcc tcccaggtag ctgggactac aggctcctgc | 600 |
| caccacgccc agctaatttt ttttttttt ttttttgtat ttttagtaga gggggttt | 660 |
| caccgtgtta gccaggatgg tctcaatctc ctgagctcat gatccgcctg ccttggcctc | 720 |
| ccaaagtgct gggattacag gcgtgagcca ccactcccgg cctcctccag ccccatctct | 780 |
| tcacatgctt ttcccacctc agttatgctg gtctcctttc tgttcctcaa atatgcccaa | 840 |
| gtcttccagc ccagggccc ccgtgctatt tcctgcctct ccaccttctg caaagctaag | 900 |
| gcccatcttc caggtctcac ataaatactg tctttcccga aagcctcttc caaccatcca | 960 |
| caagcaggat cccaaactcc tcccattcaa cctgacagcc tcacatagct cctgtcacca | 1020 |
| tgtgtaattt ttgcttacta gcagatcaaa gaacagaagc aagccgtttg attgtttctt | 1080 |
| tttgttttgt tttgttttta gacagagtct cacgagcctc cttacaaaat agaaaagtca | 1140 |
| atgggatttc agggaaaatg gataatcttc gttggggca gtcaaggaag gctttgtgga | 1200 |
| acctttgaat taggtcttga cattatatct tgacagtact ttgaataaat acaataatg | 1260 |
| ttatttttt gttaagactc atgcaaccgc atctatgtaa atgaatccgt acatagtatt | 1320 |
| cattcgagtg tgaaatcaga ctttgggatg ctttaaaatt taacagtcag gaacacttac | 1380 |
| tctatttat ggacttaaat ttgttgaggt ggcagggaac aacttgagtg aagggtggga | 1440 |
| catggcagtg tgtatgtggg ggaaaaaggt ggccagcaga aagggaagc aggggacaga | 1500 |
| gtattttgag ggattagacc tgaccagcta taacaggaaa tagaggctgt agattgaagg | 1560 |
| atagctacaa tggatgttat ggagaaattc caactgggt ggaaacatgt agctgcaaaa | 1620 |
| ttggaagagc agcttattct aggcagaaaa gaagaaagta aaaggcatct gaggggacac | 1680 |
| taaattaatg cttactgata agtaaacaag cctctggaag tagaaaggta aaagcataaa | 1740 |
| ttgcttggtc aaccacaacc gcttgggagt gctggaggct tcatgactaa accaaagtct | 1800 |
| gtccctgaag ctccctcttc cggcagaaat aaatactgca cactaagctg gctgactcct | 1860 |
| ttcattaaaa ggtgcttgcc aatctctaaa cagtttacct gtatgggagt cataattgta | 1920 |
| atatcttggt gaggattttg ttgtgctttc aggcaaacca taaaggaac actaatttaa | 1980 |
| ataaatacaa acaatgttat tttattctta agattcaggc aaccacatct atgtaagtga | 2040 |

| | |
|---|---|
| atccttacat ggtattcatt caagtgtgaa accaaacttt aggatgcttt aaaatttaac | 2100 |
| aatcaggaac aagactctgt taaaaaaaaa aaaaaagaaa tgttagaact ctgtcaaact | 2160 |
| ataaaaatat aaagtgaaat agcacagtgc agacagactg tacagaccag tgtgctacct | 2220 |
| ttcatgtaaa ggggaattac atatattata tatatgattt ttttattatt tgtgtatata | 2280 |
| cagtactcac tgtatatgca taaagtctgc aagtacatgc tgggggaag gggtggatgg | 2340 |
| gagacaagga tggaagattt ttttgttgtt ttttttgga gaccgagtct cgctctgtca | 2400 |
| ctcaggctgg agggcagtgg caccatctca gctcactgca acctccacct cccaggttca | 2460 |
| agagattctc ctgcctcagc ctcccgagta gctgggacta caggcatcca tcaccacgct | 2520 |
| cagctaattt ttgtatttta ttagagatga ggttttgcta tatatatata tatatata | 2580 |
| tatgaatata tgaatatata tatgaata tatgaatata tatatatata tgaatatatg | 2640 |
| aatatatata tattggccag gctggtctcg aactcctgcc ctcaggtgat ctgcccacct | 2700 |
| cagcctccca aagtgctggg attacaggtg tgagtggcct ggaagatttt ttattatata | 2760 |
| ctgtttaaaa gttttaagt agttgaaaca catgaagaca tcacctcaaa aagttatatt | 2820 |
| aacaattcaa aaatatgcac attaaggatt aatttttttg aaaaatttaa aaattgagaa | 2880 |
| atat | 2884 |

<210> SEQ ID NO 9
<211> LENGTH: 1501
<212> TYPE: DNA
<213> ORGANISM: Homo sapiens

<400> SEQUENCE: 9

| | |
|---|---|
| catgggacag taacacagta atcatgaaga attataaaaa taagtgctgg ccgggagcag | 60 |
| tggctcaagc ctataatccc agcactttgg gaggccgagg cgggcagatc acaaggtcag | 120 |
| gagatcaaga ccatcctggc taacacagtg aaaccctgtc tctactaaaa atacaaaaaa | 180 |
| aattagacgg gctttgtaga gggcgcctgg agtcccagct actcgggaga ctgaggcagg | 240 |
| agaatggtgt gaactcatga ggtggagctt gcagtgagcc gagatcacgc cactgcactc | 300 |
| cagcatggac aacagagcga gactccctct caaaaaaaat aaataataa gtgctaaggc | 360 |
| tgattatttt attagcccta agaatccaat taaaatagaa atcttgtatt tatgctattc | 420 |
| tttcaaaatc tttatgtaaa gcaagctttt aataggatgt tataaaaata gattttgctc | 480 |
| cttgtgttca gtttctcct cttgaaattg cacattttac attttttaaa aaattaaaat | 540 |
| taaaaacaa aatagtatga tagtgttaat ttggcagttc caactttagt aacctatctt | 600 |
| acagaaatat gaatagacaa aataaagatg tgtgaggatg tactttgcag cagcattata | 660 |
| atagcaaaaa cctggaaaca aatattgatg gacaggttaa gtaaatcata ggacattcat | 720 |
| acaatggaat actagcaaaa atattaaaaa gaatgaggta gatattgata tgctagtatg | 780 |
| gaaagatgtc cataattatc tagttcccca cctcaaaaaa aaaaaaaaa cctgagaatc | 840 |
| attatactga gaatggtcca atttgtgtct gtatgtacat aatatgtaca taacaaatat | 900 |
| agtatatttt tacacagggg aaaagtccaa aagaatatca acctgtaaaa agtagttatc | 960 |
| ccagctgggt gaggttgctc atgcctgtaa tcccagcact tgggaggca gaggcaggcg | 1020 |
| gatcacaagg tcaggagatc gagaccatcc tggctaacac agtgaaaccc tgtctctact | 1080 |
| aaaaatacaa aaaattagcc aggtatggcg aggtgagcct gtagtcctag ttgttgggga | 1140 |
| ggctgaggca ggagaatagc gtgaaccagg gaggaggagc ttgcagtgag ccgagatggt | 1200 |

| | | |
|---|---|---|
| gccactgcac tccagcctgg gctacacagc gagactccat ctcaaaaaga aaaagtagtt | 1260 | |
| agttatccct ggaaagtaaa attgagtagg aacttaaatg ggttactatc acctttgact | 1320 | |
| ttataaaggt gcacacaaac acacaaaatg tgtatgtatt taattacaaa cagtaagaga | 1380 | |
| cctggcatgg tgcctcacac ctgtaatctc agcactttgg gaggcagagg caggagaatc | 1440 | |
| acttgaggcc aggagtttga gaccaaccta tgcaacaagc gaaatccaac cccccctttt | 1500 | |
| c | 1501 | |

<210> SEQ ID NO 10
<211> LENGTH: 1501
<212> TYPE: DNA
<213> ORGANISM: Homo sapiens

<400> SEQUENCE: 10

| | | |
|---|---|---|
| gttttatgga cttaaatttg ttgaggtggc agggaacaac ttgagtgaag ggtgggacat | 60 | |
| ggcagtgtgt atgtggggga aaaaggtggc cagcagataa gggaagcagg ggacagagta | 120 | |
| ttttgaggga ttagacctga ccagctataa caggaaatag aggctgtaga ttgaaggata | 180 | |
| gctacaatgg atgttatgga gaaattccaa ctggggtgga aacatgtagc tgcaaaattg | 240 | |
| gaagagcagc ttattctagg cagaaaagaa gaaagtaaaa ggcatctgag gggacactaa | 300 | |
| attaatgctt actgataagt aaacaagcct ctggaagtag aaaggtaaaa gcataaattg | 360 | |
| cttggtcaac cacaaccgct tgggagtgct ggaggcttca tgactaaacc aaagtctgtc | 420 | |
| cctgaagctc cctcttccgg cagaaataaa tactgcacac taagctggct gactcctttc | 480 | |
| attaaaaggt gcttgccaat ctctaaacag tttacctgta tgggagtcat aattgtaata | 540 | |
| tcttggtgag gattttgttg tgctttcagg caaaccataa aaggaacact aatttaaata | 600 | |
| aatacaaaca atgttatttt attcttaaga ttcaggcaac cacatctatg taagtgaatc | 660 | |
| cttacatggt attcattcaa gtgtgaaacc aaactttagg atgctttaaa atttaacaat | 720 | |
| caggaacaag actctgttaa aaaaaaaaaa aaagaaatgt tagaactctg tcaaactata | 780 | |
| aaaatataaa gtgaaatagc acagtgcaga cagactgtac agaccagtgt gctacctttc | 840 | |
| atgtaaaggg gaattacata tattatatat atgattttt tattatttgt gtatatacag | 900 | |
| tactcactgt atatgcataa agtctgcaag tacatgctgg ggggaagggg tggatgggag | 960 | |
| acaaggatga agattttttt tgttgttttt ttttggagac cgagtctcgc tctgtcactc | 1020 | |
| aggctggagg gcagtggcac catctcagct cactgcaacc tccacctccc aggttcaaga | 1080 | |
| gattctcctg cctcagcctc ccgagtagct gggactacag gcatccatca ccacgctcag | 1140 | |
| ctaattttg tattttatta gagatgaggt tttgctatat atatatatat atatatatat | 1200 | |
| gaatatatga atatatatat atgaatatat gaatatatat atatatatga atatatgaat | 1260 | |
| atatatatat tggccaggct ggtctcgaac tcctgccctc aggtgatctg cccacctcag | 1320 | |
| cctcccaaag tgctgggatt acaggtgtga gtggcctgga agattttta ttatatactg | 1380 | |
| tttaaaagtt tttaagtagt tgaaacacat gaagacatca cctcaaaaag ttatattaac | 1440 | |
| aattcaaaaa tatgcacatt aaggattaat ttttttgaaa aatttaaaaa ttgagaaata | 1500 | |
| t | 1501 | |

<210> SEQ ID NO 11
<211> LENGTH: 14
<212> TYPE: DNA
<213> ORGANISM: Homo sapiens

<400> SEQUENCE: 11
gcgctcgctc gctc                                                     14

<210> SEQ ID NO 12
<211> LENGTH: 6015
<212> TYPE: DNA
<213> ORGANISM: Homo sapiens

<400> SEQUENCE: 12

| | | | | | |
|---|---|---|---|---|---|
| attgcaaata | cacacaatta | tacataaagg | cacagaatac | atacagaacc | agagctacac | 60 |
| ggtaacaccc | tgaagaccga | cttcttgttt | tcctggggga | aggaggttgg | tgtgtaagta | 120 |
| tgtggaaagt | gtggggttca | gggaccacac | ctaagagcca | ccagaactat | ccctttctat | 180 |
| agaaacaggc | ttcgtggcgg | atgaagaccc | catcttgggg | ttccaccaga | tattcctact | 240 |
| aaagaacatc | agctgggtgt | ggtggctcat | gcctgtaatc | ccagcacttt | gggaagctga | 300 |
| ggcgggtgga | tcacttgagg | tcaggagatc | gagaccagcc | tggccaacat | ggtgaaacct | 360 |
| tgtctctact | aaaaatacaa | aaattagcca | ggcgtggagc | acgcctgtaa | tcccagctac | 420 |
| ttgggaggct | gaggtaggag | aatcacttga | acctgggagg | cggaggttgc | agtgagccga | 480 |
| gatcacatca | ctgcactcca | gcctgggcga | cacagtgaga | ctccgtctca | aaaacaaaac | 540 |
| aaaaccaaac | aaaacaaaac | atcagcgatg | caatgatgct | tgggtttgca | ccaatgatat | 600 |
| gcaggcttgc | tctgcacaac | ttcagctgac | ctcctctcca | ccgggccctc | acgctgcctc | 660 |
| ctcttccctc | ctctttccag | aactattgcc | actcctccag | atatgatgca | caaatgagca | 720 |
| gggtcgcagt | gggagtgggc | gcagtgcgct | gatgccacgg | aggtgttgtg | catgacgtct | 780 |
| ggacactaga | ctagctgcat | gtaatgggaa | aagtttgtgt | tgtaccagcg | catgccttgg | 840 |
| aaagacttaa | gtaatgcaaa | aggttgtcct | ttaaaaaaaa | aaaaaatctg | gccggtcgcg | 900 |
| gcggctcacg | cctgtaatcc | cagcattttg | ggaggccgag | gcagtcggat | cacgaggtca | 960 |
| ggaattcgag | accagcctgg | ccaacatggt | gaaaccccgt | ctctactaaa | aacaaaaat | 1020 |
| tagccgggcg | tggtggagca | cgcctgtagt | cccagctact | caggaggctg | aggcaggaga | 1080 |
| atcgcttgaa | cccgggaggc | agagcttgca | gtgagccgac | atcgcgccac | tgcactccag | 1140 |
| cctgggcgac | agagcaagcc | tccgtctcaa | aacaacaac | aacaacaaaa | aaaaacaaaa | 1200 |
| ctactgacaa | gttgctctac | ttaacccaaa | gaaagtgaag | gagaaagcgg | ctgcctcacc | 1260 |
| gcctagacat | tgagtcgccg | gatgtttcaa | tgcctcatga | tacaataaaa | ccacaaaaat | 1320 |
| tttcgtaaca | gcagcagcaa | caacaacaac | aaaagagaaa | gagagaggga | aagaaacagg | 1380 |
| cctcgtggga | tgcgcagttt | acgtctccgc | gcaaacccaa | ggacttcaga | gtgggtggga | 1440 |
| aactcccaca | gcgcttggga | aacagtctgt | agtctctgtc | ccgatttttgg | ccctttttctg | 1500 |
| tatgattttt | atgggactct | tcctgtcaca | aagtgccagc | caccttccca | atcttgagtt | 1560 |
| gggcgcggga | tccgtaaggt | gaagatcaag | gtgtgctcat | cgcttgggcc | cgctgaaagg | 1620 |
| tgattcgccc | ccacctgct | ggaactcctt | gccggacc | accaatccca | gcatgccttg | 1680 |
| agagcgcgcg | agggcctggg | cggttcccag | gaggtccggg | tgggcgcagg | agaagcgcgg | 1740 |
| gccagtgaaa | gctctgagag | ccctgtccct | gtggacactg | tgtcttgggt | tcctttactc | 1800 |
| ggtgtggctc | agggattacc | attagggagt | ggagtgtgga | tttctcttgc | cccgagccct | 1860 |
| aaatgccttg | gggccctgcc | ttgcacccca | ctgtgctttt | aggggtgtgg | ccctgtgggc | 1920 |
| tacatttccc | agcgtgccct | aggatcgtgg | tcctgacctt | ttcaccgcaa | atttcatttc | 1980 |
| ccagcatgcc | ctgcgaggtc | acccagggaa | gcttggaagt | ggactgtctt | tcatggcttc | 2040 |

```
taggttgcgg actcagtttc ccatggtgcc ctggtgaacc cattcattca ttcattccaa    2100
aaatatttgc gatcaggttc tctcaggttc tgttctaaga accgaggaca agtagtgcac    2160
agaagacaaa agatcccgct ctcgtggagc ttatttctag ttaagggggtc aggaaaaaaa   2220 ccaaaataaa taaaacccag ctgggcatgg tggcttacgc tcgtcatccc agcaggatta    2280
caggccgagg cgggcggatc atgaggtcaa gagatcaaga ccatcatggc caacatggtg    2340
aaatcccgtc tctactaaaa atataaaaat tagcagggcg gggtggcgcg cgcctgttat    2400
cccagctact ctggggactg agccagaatt gcttgaacct gggaagcgga ggttgcagcg    2460
agccgatatc gcgccactga actccagcgt ggcgacagag cgagactccg tctcaaaaca    2520
aagaaaacaa aataaaacaa caataacaaa acaactctgc ctctcccgc actccctccc     2580 acgcggctgt ccagtcgaat tcctaactgc cccggggcag tctgctattc atccccttta    2640
cccggtgcta cacacttcct agtatgccgt ggggcacccc tccggcctgt agactccatt    2700
tcccagcatt ccccgaggga ggccctcatc tggcgatttc cactgggcgc ctcggagctg    2760
cggacttccc agtgtgcatc ggggcacagc gactcctgga agtggccaag ggccacttct    2820
gctaatggac tccatttccc agcgctcccc gcgacctgcc cagcacaccc tggggcagcg    2880
ccgtgacgtc agcacgccgg gcggggaccg ggagatcctt ggggcggtgg ggggccagcg    2940
gcagttcccg gcggcccccg gggcgggcgg gcgggcgggt ggtggcggcg gttgggggctc   3000 ggcgctcgct cgctcgctgg gcgggcgggc ggtgcgatgt ccggagagga tggcccggcg    3060
gctggcccgg gggcggcggc ggcggctgcc cgggagcggc gacgggagca gctgcggcag    3120 tgggggggcgc gggcggcgc cgagcctggc cccggagagc gccgcgcccg caccgtccgc    3180
ttcgagcgcg ccgccgagtt cctggcggcc tgtgcgggcg gcgacctgga cgaggcgcgt    3240
ctgatgctgc gcgccgccga ccctggcccc ggcgccgagc tcgacccgc cgcgccgccg     3300 cccgcccgcg ccgtgctgga ctccaccaac gccgacggta tcagcgccct gcaccaggtc    3360 agcgccccc gccggcgtc tcccggggcc aggtccaccc tctgctgcgc cacctggggc      3420
atcctccttc ccgttgcca gtctcgatcc gccccgtcgt tcctggccct gggctttgcc     3480
accctatgct gacaccccgt cccagtcccc cttaccattc cccttcgacc acccacttc     3540 cgaattggag ccgcttcaac tggccctggg cttagccact ctgtgctgac cactctgccc    3600
caggcctcct taccattccc cttcgaccta ctctcttccg cattggagtc gctttaactg    3660
gccctggctt tggcagcctg tgctgaccca tgcagtcctc cttaccatcc ctccctcgac    3720
ttcccctctt ccgatgttga gccctccag ccggtcctgg actttgtctc cttccctgcc    3780
ctgccctctc ctgaacctga ccagctccc atagctcagt ctggtctatc tgcctggccc    3840
tggccattgt cactttgcgc tgccctcctc tcgcccccga gtgcccttgc tgtgccgccg    3900
gaactctgcc ctctaacgct gccgtctctc tcctgagtcc ggaccacttt gagctctact    3960
ggcttctgcg ccgcctctgg cccactgttt cccttccca ggcaggtcct gctttctctg     4020
acctgcattc tctcccctgg gcctgtgccg ctttctgtct gcagcttgtg gcctgggtca    4080
cctctacggc tggcccagat ccttccctgc cgcctccttc aggttccgtc ttcctccact    4140
ccctcttccc cttgctctct gctgtgttgc tgcccaagga tgctctttcc ggagcacttc    4200
cttctcggcg ctgcaccacg tgatgtcctc tgagcggatc ctccccgtgt ctgggtcctc    4260
tccgggcatc tctcctccct cacccaaccc catgccgtct tcactcgctg ggttcccttt    4320
tccttctcct tctggggcct gtgccatctc tcgtttctta ggatggcctt ctccgacgga    4380
tgtctccctt gcgtcccgcc tcccttctt gtaggcctgc atcatcaccg ttttctgga     4440
```

```
caacccccaaa gtacccgtc tccctggctt tagccacctc tccatcctct tgctttcttt     4500
gcctggacac cccgttctcc tgtggattcg ggtcacctct cactcctttc atttgggcag     4560
ctcccctacc ccccttacct ctctagtctg tgctagctct tccagccccc tgtcatggca    4620
tcttccaggg gtccgagagc tcagctagtc ttcttcctcc aacccgggcc cctatgtcca    4680
cttcaggaca gcatgtttgc tgcctccagg gatcctgtgt ccccgagctg ggaccacctt    4740
atattcccag ggccggttaa tgtggctctg gttctgggta cttttatctg tcccctccac    4800
cccacagtgg ggccactagg gacaggattg gtgacagaaa agcccatcc ttaggcctcc     4860 tccttcctag tctcctgata ttgggtctaa cccccaccto ctgttaggca gattccttat    4920
ctggtgacac accccccattt cctggagcca tctctctcct tgccagaacc tctaaggttt   4980
gcttacgatg gagccagaga ggatcctggg agggagagct tggcagggg tgggagggaa     5040 ggggggatg cgtgacctgc ccggttctca gtggccaccc tgcgctaccc tctcccagaa     5100
cctgagctgc tctgacgcgg ctgtctggtg cgtttcactg atcctggtgc tgcagcttcc    5160
ttacacttcc caagaggaga agcagtttgg aaaaacaaaa tcagaataag ttggtcctga    5220
gttctaactt tggctcttca cctttctagt ccccaattta tattgttcct ccgtgcgtca    5280
gttttacctg tgagataagg ccagtagcca gccccgtcct ggcagggctg tggtgaggag    5340
gggggtgtcc gtgtggaaaa ctccctttgt gagaatggtg cgtcctaggt gttcaccagg    5400
tcgtggccgc ctctactccc tttctctttc tccatccttc tttccttaaa gagtccccag    5460
tgctatctgg gacatattcc tccgcccaga gcagggtccc gcttccctaa ggccctgctc    5520
tgggcttctg ggtttgagtc cttggcaagc ccaggagagg cgctcaggct tccctgtccc    5580
ccttcctcgt ccaccatctc atgcccctgg ctctcctgcc ccttccctac aggggttcct   5640
ggctctgctc ttcagactga gccccgttcc cctgcatccc cgttcccctg catcccccttt   5700 cccctgcatc ccccagaggc cccaggccac ctacttggcc tggacccac gagaggccac     5760 cccagccctg tctaccaggc tgccttttgg gtggattctc ctccaactgt ggggtgactg    5820
cttggcaaac tcactcttcg gggtatccca ggaggcctgg agcattgggg tgggctgggg    5880
ttcagagagg agggattccc ttctcaggtt acgtggccaa gaagcagggg agctgggttt    5940
gggtcaggtc tgggtgtggg gtgaccagct tatgctgttt gcccaggaca gcctagtttt    6000
agcgctgaaa ccctc                                                    6015
```

NUCLEIC ACID MOLECULES CONTAINING SPACERS AND METHODS OF USE THEREOF

FIELD OF THE INVENTION

The present invention relates to nucleic acid molecules containing spacers for the production of viral particles with improved efficiency and that contain reduced quantities of contaminating nucleic acids.

BACKGROUND

Parvoviral gene therapy vectors, such as those based on adeno-associated virus (AAV), have been successfully used for stable gene expression in animal models and in patients. While parvoviral gene therapy vectors represent a promising paradigm, safety issues including contaminants found in vector stocks have limited the tolerable dose for otherwise effective treatments. One source of reduced efficacy and vector toxicity is contaminating nucleic acids from the vector (e.g., prokaryotic and baculoviral nucleic acids, antibiotic resistance gene, and nucleic acids with high CpG content) present inside viral vector particles. Another challenge that has hindered the clinical development of viral gene therapy has been the inability to robustly package viral genomes into capsid proteins, particularly when these genomes inherently contain self-inactivating sequences. A need currently exists for nucleic acid molecules that are capable of being efficiently packaged into viral particles while preventing the incorporation contaminating nucleic acids into such vectors.

SUMMARY

The present invention relates to nucleic acid molecules and concatemers containing spacer sequences that can be efficiently packaged into viral particles, as well as methods of producing viral particles containing these nucleic acid cassettes.

In a first aspect, the invention provides a nucleic acid molecule containing a first spacer (SS1); a first inverted terminal repeat (ITR1); a cloning site (CS); a second inverted terminal repeat (ITR2); and a second spacer (SS2). The SS1 and/or the SS2 has at least 85% sequence identity (e.g., at least 90%, 91%, 92%, 93%, 94%, 95%, 96%, 97%, 98%, 99%, or 100% sequence identity) to a nucleic acid sequence selected from the group consisting of SEQ ID NOS: 3-5 and 9-11. Additionally, the components are operably linked to each other in a 5'-to-3' direction as: SS1-ITR1-CS-ITR2-SS2.

In a second aspect the invention features a nucleic acid molecule including a first spacer (SS1); a first inverted terminal repeat (ITR1); a heterologous polynucleotide molecule (HPM); a second inverted terminal repeat (ITR2); and a second spacer (SS2), wherein the SS1 and/or the SS2 includes a portion having at least 85% sequence identity (e.g., at least 90%, 91%, 92%, 93%, 94%, 95%, 96%, 97%, 98%, 99%, or 100% sequence identity) to a nucleic acid sequence selected from the group consisting of SEQ ID NOS: 3-5 and 9-11. In this aspect, the components are operably linked to each other in a 5'-to-3' direction as: SS1-ITR1-HPM-ITR2-SS2.

In some embodiments of the above-described aspects, the SS1 and/or the SS2 contains a portion that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 3. In some embodiments, the SS1and/or the SS2 has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 1 or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 3.

In some embodiments of the above-described aspects, the SS1 and/or the SS2 contains a portion that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 4. In some embodiments, the SS1and/or the SS2 has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 2 or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 4.

In some embodiments of the above-described aspects, the SS1 has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 1, or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 3, and the SS2 has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 2, or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 4.

In some embodiments of the above-described aspects, the SS1 has at least SS2% sequence identity (e.g., at least 90%, 91%, 92%, 93%, 94%, 95%, 96%, 97%, 98%, 99%, or 100% sequence identity) to the nucleic acid sequence of SEQ ID NO: 2, or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 4, and the SS2 has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 1, or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 3.

In some embodiments of the above-described aspects, the SS1 and/or the SS2 contains a portion that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 5. In some embodiments, the SS1and/or the SS2 has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 6 or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 5.

In some embodiments of the above-described aspects, the SS1 and/or the SS2 contains a portion that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 9. In some embodiments, the SS1and/or the SS2 has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 7 or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 9.

In some embodiments of the above-described aspects, the SS1 and/or the SS2 contains a portion that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 10. In some embodiments, the SS1and/or the SS2 has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 8 or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 10.

In some embodiments of the above-described aspects, the SS1 has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 7, or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 9, and the SS2 has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 8, or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 10.

In some embodiments of the above-described aspects, the SS1 has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 8, or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 10, and the SS2 has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 7, or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 9.

In some embodiments of the above-described aspects, the SS1 and/or the SS2 contains a portion that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 11. In some embodiments, the SS1and/or the SS2 has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 12 or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 11.

In some embodiments of the foregoing aspects, the SS1 and the SS2 includes any combination of polynucleotide sequences listed in Table 2.

In an additional aspect, the invention provides a nucleic acid molecule including a first spacer (SS1); a first inverted terminal repeat (ITR1); a heterologous polynucleotide molecule (HPM); a second inverted terminal repeat (ITR2); and a second spacer (SS2), wherein the HPM encodes XLMTM, GAA, FKRP, UGT1A1, PPCA, MYBPC3, CASQ2, GAN, GNS, HGSNAT, NAGLU, SGSH, IDUA, ARSB, GALNS, IDS, CLN2, CLN5, G6PC, SMN1, MECP2, HEXA, ASPA, GNE, SGCA, POMT1, POMT2, LARGE, FKTN, ISPD, POMGnT1, GTDC2, B3GALNT2, DMD, GUSB, or mini-dystrophin. The above components are operably linked to each other in a 5'-to-3' direction as: SS1-ITR1-HPM-ITR2-SS2.

In another aspect, the invention features a nucleic acid molecule including a first spacer (SS1); a first inverted terminal repeat (ITR1); a heterologous polynucleotide molecule (HPM); a second inverted terminal repeat (ITR2); and a second spacer (SS2), wherein the HPM encodes miR-128. In this aspect, the components are operably linked to each other in a 5'-to-3' direction as: SS1-ITR1-HPM-ITR2-SS2.

In an additional aspect, the invention features a nucleic acid molecule including a first spacer (SS1); a first inverted terminal repeat (ITR1); a first homology arm (HR1); a cloning site (CS); a second homology arm (HR2); a second inverted terminal repeat (ITR2); and a second spacer (SS2), wherein the components are operably linked to each other in a 5'-to-3' direction as: SS1-ITR1-HR1-CS-HR2-ITR2-SS2.

In another aspect, the invention features a nucleic acid molecule including a first spacer (SS1); a first inverted terminal repeat (ITR1); a first homology arm (HR1); a heterologous polynucleotide molecule (HPM); a second homology arm (HR2); a second inverted terminal repeat (ITR2); and a second spacer (SS2), wherein the components are operably linked to each other in a 5'-to-3' direction as: SS1-ITR1-HR1-HPM-HR2-ITR2-SS2.

In some embodiments of the foregoing aspects of the invention, HPM encodes XLMTM, GAA, FKRP, UGT1A1, PPCA, MYBPC3, CASQ2, GAN, GNS, HGSNAT, NAGLU, SGSH, IDUA, ARSB, GALNS, IDS, CLN2, CLN5, G6PC, SMN1, MECP2, HEXA, ASPA, GNE, SGCA, POMT1, POMT2, LARGE, FKTN, ISPD, POMGnT1, GTDC2, B3GALNT2, DMD, GUSB, or mini-dystrophin. In some embodiments, the HPM encodes for an inhibitory RNA molecule. In some embodiments, the inhibitory RNA molecule is small or short hairpin RNA (shRNA), microRNA (miRNA), small or short interfering (si)RNA, trans-splicing RNA, antisense RNA, or ribozyme. In some embodiments, the miRNA is miR-128.

In some embodiments of the above-described aspects of the invention, the SS1 and/or the SS2 includes a portion having at least 85% sequence identity (e.g., at least 90%, 91%, 92%, 93%, 94%, 95%, 96%, 97%, 98%, 99%, or 100% sequence identity) to a nucleic acid sequence selected from the group consisting of SEQ ID NOS: 3-5 and 9-11.

In some embodiments, the SS1 and/or the SS2 contains a portion that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 3. In some embodiments, the SS1and/or the SS2 has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 1 or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 3.

In some embodiments, the SS1 and/or the SS2 contains a portion that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 4. In some embodiments, the SS1 and/or the SS2 has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 2 or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 4.

In some embodiments, the SS1 has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 1, or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 3, and the SS2 has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 2, or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 4.

In some embodiments, the SS1 has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 2, or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 4, and the SS2 has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 1, or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 3.

In some embodiments, the SS1 and/or the SS2 contains a portion that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 5. In some embodiments, the SS1 and/or the SS2 has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 6 or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 5.

In some embodiments, the SS1 and/or the SS2 contains a portion that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 9. In some embodiments, the SS1 and/or the SS2 has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 7 or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 9.

In some embodiments, the SS1 and/or the SS2 contains a portion that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 10. In some embodiments, the SS1 and/or the SS2 has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 8 or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 10.

In some embodiments, the SS1 has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 7, or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 9, and the SS2 has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 8, or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 10.

In some embodiments, the SS1 has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 8, or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 10, and the SS2 has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 7, or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 9.

In some embodiments, the SS1 and/or the SS2 contains a portion that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 11. In some embodiments, the SS1 and/or the SS2 has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 12 or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 11.

In some embodiments of the above-described aspects, the SS1 and the SS2 includes any combination of polynucleotide sequences listed in Table 2.

In some embodiments of the above-described aspects of the invention, the nucleic acid molecule further includes a eukaryotic promoter ($P_{Euk}$), wherein the eukaryotic promoter and the heterologous polynucleotide molecule are operably linked to each other in a 5'-to-3' direction as: $P_{Euk}$-HPM.

In some embodiments, the eukaryotic promoter is a tissue specific promoter (e.g., a liver specific promoter, muscle specific promoter, or neuronal specific promoter) or a constitutive promoter (e.g., a cytomegalovirus promoter or a chicken-(β-actin promoter).

In some embodiments of the above-described aspects of the invention, the nucleic acid molecule further includes a polyadenylation site (pA), wherein the polyadenylation site and the ITR2 are operably linked to each other in a 5'-to-3' direction as: pA-ITR2.

In some embodiments, the polyadenylation site contains the human P-globin polyadenylation site, the SV40 late polyadenylation site, the SV40 early polyadenylation site, or the bovine growth hormone polyadenylation site.

In some embodiments of the invention, the SS2 and/or SS2 does not contain an open reading frame that is greater than 100 amino acids. In some embodiments, the SS1 and/or SS2 contains an open reading frame that is less than 50 amino acids. In additional embodiments, the SS1 and/or SS2 does not contain a prokaryotic or baculoviral transcription factor binding site.

In some embodiments of the above-described aspects of the invention, the SS1 and/or SS2 contains a total CpG content that is less than 1% (e.g., less than 0.9%, 0.8%, 0.7%, 0.6%, 0.5%, 0.4%, 0.3%, 0.2%, or 0.1%) of the total nucleic acid sequence of the SS1 and/or SS2. In some embodiments, the SS1 and/or SS2 contains a total CpG content that is less than 0.5% (e.g., less than 0.4%, 0.3%, 0.2%, or 0.1%) of the total nucleic acid sequence of the SS1 and/or SS2. In some embodiments, the SS1 and/or SS2 contains an intron (e.g., a vertebrate intron). For instance, the vertebrate intron may be a mammalian intron, such as a human intron. In some embodiments, the SS1 is about 2.0 Kb to about 5.0 Kb. In some embodiments, the SS2 is about 2.0 Kb to about 5.0 Kb. In some embodiments, the SS1 and SS2 together are about 4.0 Kb to about 10.0 Kb. In some embodiments, the HPM and either SS1 or SS2 together are about 5.0 Kb to about 10.0 Kb. In some embodiments, the SS1, SS2, and HPM together are about 10.0 Kb to about 15.0 Kb.

In some embodiments, the SS1 is flanked by one or more cloning sites. In some embodiments, the SS2 is flanked by one or more cloning sites. In some embodiments, the ITR1 and/or ITR2 is a parvoviral ITR, such as an adeno-associated virus (AAV) ITR. In some embodiments, the AAV ITR is an AAV serotype 2 ITR.

In another aspect, the invention provides a vector including the nucleic acid molecule of any of the above-described embodiments of the invention. In some embodiments, the vector includes a prokaryotic or baculoviral promoter operably linked to a selectable marker gene positioned 5' to SS1 and/or 3' to SS2. In some embodiments, the selectable marker gene is an antibiotic resistance gene. In some embodiments, the vector contains a prokaryotic origin of replication positioned 5' to SS1 and/or 3' to SS2. In some embodiments, the nucleic acid molecule is circular. In some embodiments, the nucleic acid molecule is linear.

In another aspect, the invention provides a nucleic acid molecule of the formula: $(SS1-ITR1-CS-ITR2-SS2)_n$. In this aspect, SS1 is a first spacer; ITR1 is a first inverted terminal repeat; CS is a cloning site; ITR2 is a second inverted terminal repeat; and SS2 is a second spacer. These components are operably linked to each other in a 5'-to-3' direction, and n is an integer that is greater than 1 (e.g., an integer from 2 to 100 (e.g., an integer from 5 to 90, from 10 to 80, from 20 to 70, from 30 to 60, from 40 to 50, from 10 to 50, from 15 to 45, from 16 to 44, from 17 to 43, from 18 to 42, from 19to 41, or from 20 to 40)).

In another aspect, the invention features a nucleic acid molecule of the formula: $(SS1-ITR1-HPM-ITR2-SS2)_n$. In this aspect, SS1 is a first spacer (SS1); ITR1 is a first inverted terminal repeat; HPM is a heterologous polynucleotide molecule; ITR2 is a second inverted terminal repeat; and SS2 is a second spacer. These components are operably linked to each other in a 5'-to-3' direction, and n is an integer that is greater than 1 (e.g., an integer from 2 to 100 (e.g., an integer from 5 to 90, from 10 to 80, from 20 to 70, from 30 to 60, from 40 to 50, from 10 to 50, from 15 to 45, from 16 to 44, from 17 to 43, from 18 to 42, from 19 to 41, or from 20 to 40).

In some embodiments of either of the foregoing aspects of the invention, n is an integer from 20 to 40.

In some embodiments of either of the foregoing aspects, the SS1 and the SS2 together include a portion having at least 85% sequence identity (e.g., at least 90%, 91%, 92%, 93%, 94%, 95%, 96%, 97%, 98%, 99%, or 100% sequence identity) to a nucleic acid sequence selected from the group consisting of SEQ ID NOS: 3-5 and 9-11.

In some embodiments, the SS1 and the SS2 together include a portion that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 3. In some embodiments, the SS1 and the SS2 together contain a polynucleotide that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 1 or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 3.

In some embodiments, the SS1 and the SS2 together include a portion that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 4. In some embodiments, the SS1 and the SS2 together contain a polynucleotide that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 2 or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 4.

In some embodiments, the SS1 has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 2, or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 4, and the SS2 has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 1, or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 3.

In some embodiments, the SS1 and the SS2 together include a portion that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 5. In some embodiments, the SS1 and the SS2 together contain a polynucleotide that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 6 or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 5.

In some embodiments, the SS1 and the SS2 together include a portion that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 9. In some embodiments, the SS1 and the SS2 together contain a polynucleotide that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 7 or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 9.

In some embodiments, the SS1 and the SS2 together include a portion that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 10. In some embodiments, the SS1 and the SS2 together contain a polynucleotide that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 8 or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 10.

In some embodiments, the SS1 has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 7, or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 9, and the SS2 has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 8, or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 10.

In some embodiments, the SS1 and the SS2 together include a portion that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 11. In some embodiments, the SS1 and the SS2 together contain a polynucleotide that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 12 or a portion thereof that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 11.

In some embodiments of the above-described aspects, the SS1 and the SS2 includes any combination of polynucleotide sequences listed in Table 2.

In some embodiments, the HPM encodes XLMTM, GAA, FKRP, UGT1A1, PPCA, MYBPC3, CASQ2, GAN, GNS, HGSNAT, NAGLU, SGSH, IDUA, ARSB, GALNS, IDS, CLN2, CLNS, G6PC, SMN1, MECP2, HEXA, ASPA, GNE, SGCA, POMT1, POMT2, LARGE, FKTN, ISPD, POMGnT1, GTDC2, B3GALNT2, DMD, GUSB, or mini-dystrophin. In some embodiments, the HPM encodes an inhibitory RNA molecule. In some embodiments, the nucleic acid molecule is a small or short hairpin RNA (shRNA), microRNA (miRNA), small or short interfering (si)RNA, trans-splicing RNA, antisense RNA, or ribozyme. In some embodiments, the miRNA is miR-128.

In some embodiments, the nucleic acid molecule further contains a HR1 and a HR2, wherein the first inverted terminal repeat and the first homology arm are operably linked to each other in a 5'-to-3' direction as ITR1-HR1, wherein the second homology arm and the second inverted terminal repeat are operably linked to each other in a 5'-to-3' direction as HR2-ITR2.

In some embodiments, the nucleic acid molecule further includes a $P_{Euk}$, wherein the eukaryotic promoter and the heterologous polynucleotide molecule are operably linked to each other in a 5'-to-3' direction as $P_{Euk}$-HPM. In some embodiments, the eukaryotic promoter is a tissue specific promoter (e.g., a liver specific promoter, muscle specific promoter, or neuronal specific promoter) or a constitutive promoter (e.g., a cytomegalovirus promoter or a chicken-(β-actin promoter).

In some embodiments of the foregoing aspects of the invention, the nucleic acid molecule further includes a pA. In these embodiments, the pA and the ITR2 are operably linked to each other in a 5'-to-3' direction as: pA-ITR2.

In some embodiments, the pA contains the human β-globin polyadenylation site, the SV40 late polyadenylation site, the SV40 early polyadenylation site, or the bovine growth hormone polyadenylation site.

In some embodiments, the SS2 and the SS2 together do not include an open reading frame that is greater than 100 amino acids. In some embodiments, the SS1 and the SS2 together include an open reading frame that is less than 50 amino acids. In some embodiments, the SS1 and the SS2 together do not include a prokaryotic or baculoviral transcription factor binding site.

In some embodiments, the SS1 and the SS2 together contain a total CpG content that is less than 1% (e.g., less than 0.9%, 0.8%, 0.7%, 0.6%, 0.5%, 0.4%, 0.3%, 0.2%, or 0.1%) of the combined nucleic acid sequence of the SS1 and the SS2. In some embodiments, the SS1 and the SS2 together contain a total CpG content that is less than 0.5% (e.g., less than 0.4%, 0.3%, 0.2%, or 0.1%) of the combined nucleic acid sequence of the SS1 and the SS2. In some embodiments, the SS1 and the SS2 together contain an intron (e.g., a vertebrate intron). In some embodiments, the intron is a mammalian intron (e.g., a human intron). In some embodiments, the SS1 is about 1.0 Kb to about 2.5 Kb. In some embodiments, the SS2 is about 1.0 Kb to about 2.5 Kb. In some embodiments, the SS1 and SS2 together are about 2.0 Kb to about 5.0 Kb. In some embodiments, the HPM and either SS1 or SS2 together are about 4.0 Kb to about 7.5 Kb. In some embodiments, the SS1, SS2, and HPM together are about 5.0 Kb to about 10.0 Kb.

In some embodiments, the SS1 is flanked by one or more cloning sites. In some embodiments, the SS2 is flanked by one or more cloning sites. In some embodiments, the ITR1 and/or ITR2 is a parvoviral ITR, such as an adeno-associated virus (AAV) ITR. In some embodiments, the ITR is an AAV serotype 2 ITR.

The invention also provides a vector including a nucleic acid molecule of any of the foregoing aspects of the invention. In some embodiments, this vector includes a prokaryotic or baculoviral promoter operably linked to a selectable marker gene positioned 5' and/or 3' to the nucleic acid molecule. In some embodiments, the selectable marker gene is an antibiotic resistance gene. In some embodiments, the vector contains a prokaryotic origin of replication positioned 5' and/or 3' to the nucleic acid molecule. In some embodiments, the vector contains a circular polynucleotide. In some embodiments, the vector contains a linear polynucleotide.

In another aspect, the invention provides a plurality of viral particles containing a nucleic acid molecule that includes a first inverted terminal repeat, a heterologous polynucleotide molecule, and a second inverted terminal repeat. In this aspect, less than 1% of the viral particles contain a nucleic acid molecule that includes a contaminant nucleic acid that contains a prokaryotic nucleic acid, a baculoviral nucleic acid, and/or a nucleic acid that has a CpG content greater than 2% of the total nucleic acid of the contaminant nucleic acid. In some embodiments, less than 0.75% (e.g., less than 0.5%, 0.25%, or 0.15%) of the viral particles contain a nucleic acid molecule that includes the contaminant nucleic acid. In some embodiments, the prokaryotic nucleic acid or the baculoviral nucleic acid contains an origin of replication, a selectable marker gene, and/or a promoter including transcription factor binding sites.

In another aspect, the invention provides a plurality of viral particles that include the nucleic acid molecule of any one of the above-described embodiments of the invention.

In an additional aspect, the invention provides a host cell that contains the vector of any of the above aspects. In some embodiments, the host cell is prokaryotic (e.g., a bacterial cell, such as an *E. coli* cell). In other embodiments, the host cell is a eukaryotic cell (e.g., an insect cell or a mammalian cell, such as a HEK293 cell or a HeLa cell).

In another aspect, the invention provides a method of producing a plurality of viral particles that includes the steps of introducing into a host cell the nucleic acid molecule or vector of any one of the above-described aspects. In some embodiments, the introducing step is performed by contacting the host cell with a vector selected from the group consisting of a viral vector (such as retrovirus, adenovirus, parvovirus, coronavirus, rhabdovirus, paramyxovirus, picornavirus, alphavirus, herpes virus, or poxvirus) and a transposable element (such as a piggybac transposon or sleeping beauty transposon). In some embodiments, the introducing step is performed by electroporation or by contacting the host cell with a transformation agent selected from the group consisting of a cationic polymer (such as diethylaminoethyl-dextran), a cationic lipid, calcium phosphate, an activated dendrimer, and a magnetic bead. In some embodiments, the method further includes the step of contacting the host cell with a cell culture medium. In some embodiments, the method includes the step of isolating the plurality of viral particles from the cell culture medium. In some embodiments, the isolating step is performed by contacting the cell culture medium with a resin that includes one or more ionic substances covalently bound to the resin. In some embodiments, the contacting step is performed for a time sufficient for the plurality of viral particles to bind the one or more ionic substances. In some embodiments, the method includes the step of eluting the plurality of viral particles from the one or more ionic substances, e.g., by contacting the resin with a buffer solution that has a pH of from about 5 to about 7. In some embodiments, the plurality of viral particles includes AAV particles.

BRIEF DESCRIPTION OF THE DRAWINGS

FIG. 1 is a schematic depicting an AAV vector containing a first spacer (spacer 1), a first AAV2 ITR, a CMV promoter, a β-globin intron, a GFP-encoding polynucleotide, a β-globin polyadenylation (pA), a second AAV2 ITR, a second spacer (spacer 2), a prokaryotic origin of replication (oriC), and a kanamycin (kan) selection gene.

DETAILED DESCRIPTION OF EMBODIMENTS OF THE INVENTION

DEFINITIONS

As used herein, the term "cloning site" refers to a nucleic acid sequence containing a restriction site for restriction endonuclease-mediated cloning by ligation of a nucleic acid containing compatible cohesive or blunt ends, a region of nucleic acid serving as a priming site for PCR-mediated cloning o insert DNA by homology and extension "overlap FOR stitching", or a recombination site for recombinase-mediated insertion of target nucleic acids by recombination-exchange reaction, or mosaic ends for transposon mediated insertion of target nucleic acids, as well as other techniques common in the art.

The terms "host cell," "host cell line," and "host cell culture" are used interchangeably and refer to one or more cells into which exogenous nucleic acid has been introduced, including the progeny of such cells. Host cells include "transformants" and "transformed cells," which include the primary transformed cell and progeny derived therefrom without regard to the number of passages.

The terms "linked" or "links" or "link" as used herein are meant to refer to the covalent joining of two nucleic acids together through phosphodiester bonds, such joining can include any number of additional nucleic acids between the two nucleic acids that are being joined.

"Nucleic acid" or "polynucleotide," as used interchangeably herein, refer to polymers of nucleotides of any length, and include DNA and RNA.

The terms "heterologous polynucleotide" and "heterologous nucleic acid" are used interchangeably herein and refer to a nucleic acid molecule that is not naturally occurring in the virus.

A nucleic acid is "operably linked" when it is placed into a structural or functional relationship with another nucleic acid. For example, one segment of DNA may be operably linked to another segment of DNA if they are positioned relative to one another on the same contiguous DNA molecule and have a structural or functional relationship, such as a promoter or enhancer that is positioned relative to a coding region so as to facilitate transcription of the coding region. In other examples, the operably linked nucleic acids are not contiguous, but are positioned in such a way that they have a functional relationship with each other as nucleic acids or as proteins that are expressed by them. Enhancers, for example, do not have to be contiguous. Linking may be accomplished by ligation at convenient restriction sites or by using synthetic oligonucleotide adaptors or linkers.

The term "polyadenylation signal" or "polyadenylation site" is used to herein to mean a nucleic acid sequence sufficient to direct the addition of polyadenosine ribonucleic acid to an RNA molecule expressed in a cell.

A "promoter" is a nucleic acid enabling the initiation of the transcription of a gene in a messenger RNA, such transcription being initiated with the binding of an RNA polymerase on or nearby the promoter.

An "ITR" is a palindromic nucleic acid, e.g., an inverted terminal repeat, that is about 120 nucleotides to about 250 nucleotides in length and capable of forming a hairpin. The term "ITR" includes the site of the viral genome replication that can be recognized and bound by a parvoviral protein (e.g., Rep78/68). An ITR may be from any adeno-associated virus (AAV), with serotype 2 being preferred. An ITR includes a replication protein binding element (RBE) and a terminal resolution sequences (TRS). The term "ITR" does not require a wild-type parvoviral ITR (e.g., a wild-type nucleic acid sequence may be altered by insertion, deletion, truncation, or missense mutations), as long as the ITR functions to mediate virus packaging, replication, integration, and/or provirus rescue, and the like. The "5' ITR" is intended to mean the parvoviral ITR located at the 5' boundary of the nucleic acid molecule; and the term "3' ITR" is intended to mean the parvoviral ITR located at the 3' boundary of the nucleic acid molecule.

"Percent (%) nucleic acid sequence identity" with respect to a reference polynucleotide sequence is defined as the percentage of nucleic acids in a candidate sequence that are identical with the nucleic acids in the reference polynucleotide sequence, after aligning the sequences and introducing gaps, if necessary, to achieve the maximum percent sequence identity, and not considering any conservative substitutions as part of the sequence identity. Alignment for purposes of determining percent nucleic acid sequence identity can be achieved in various ways that are within the skill in the art, for instance, using publicly available computer software such as BLAST, BLAST-2, or Megalign (DNASTAR) software. Those skilled in the art can determine appropriate parameters for aligning sequences, including any algorithms needed to achieve maximal alignment over the full length of the sequences being compared. For purposes herein, however, % nucleic acid sequence identity values are generated using the sequence comparison computer program BLAST. The % nucleic acid sequence identity of a given nucleic acid sequence A to, with, or against a given nucleic acid sequence B (which can alternatively be phrased as a given nucleic acid sequence A that has or comprises a certain % nucleic acid sequence identity to, with, or against a given nucleic acid sequence B) is calculated as follows:

100 multiplied by (the fraction X/Y)

where X is the number of nucleotides scored as identical matches by the sequence alignment program BLAST in that program's alignment of A and B, and where Y is the total number of nucleic acids in B. It will be appreciated that where the length of nucleic acid sequence A is not equal to the length of nucleic acid sequence B, the % nucleic acid sequence identity of A to B will not equal the % nucleic acid sequence identity of B to A.

A "capsid protein" as used herein refers to any of the AAV capsid proteins that are components of AAV viral particles, including AAV8 and AAV9.

A "spacer" is any polynucleotide of at least 2.0 Kb in length that contains an open reading frame (ORF) of less than 100 amino acids; has a CpG content that is less than 1% of the total nucleic acid sequence; or does not contain transcription factor (TF) binding sites (e.g., sites recognized by a prokaryotic or baculoviral transcription factor). The term spacer does not include nucleic acids of prokaryotic or baculoviral origin. A spacer may be isolated from a naturally occurring source or modified, e.g., to reduce the size of an ORF, the CpG content, or number of transcription factor binding sites. A spacer may be selected from naturally occurring nucleic acids that promote expression of a polynucleotide, e.g., an intron found adjacent to an ORF or an enhancer found near a transcriptional start site. Use of a "spacer," as defined herein, results in a reduction of contaminating nucleic acids packaged into a viral particle.

"CpG content of X %" refers to a polynucleotide which presents X CpG dinucleotides for 100 nucleotides where X represents the number of CpG dinucleotides (Gardiner-Garden and Frommer, *J. Mol. Biol.*, 196: 261-282 (1987). By "CpG sites" is meant regions of DNA where a cytosine nucleotide occurs next to a guanine nucleotide in the linear nucleic acid sequence of nucleotides along its length, e.g., —C—phosphate—G—, cytosine and guanine separated by only one phosphate, or a cytosine 5' to the guanine nucleotide.

The term "contaminant" or "contaminating" nucleic add refers to nucleic acids that are prokaryotic or baculoviral in origin (e.g., contain prokaryotic or baculoviral transcripts or fragments thereof, transcription factor binding sites, or promoter elements); contain a CpG content of greater than 2%; or a selectable marker gene. For example, a "contaminant" or "contaminating" nucleic acid includes a bacterial origin or replication, a bacterial selectable marker gene, a bacterial antibiotic resistance gene, and a bacterial or baculoviral promoter containing transcription factor binding sites. A "contaminant" or "contaminating" nucleic acid as described herein is any polynucleotide present in a vector that is not a spacer molecule, a eukaryotic promoter, a mammalian heterologous polynucleotide molecule, a polyadenylation site, or an ITR.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Certain vectors are capable of directing the expression of genes to which they are operably linked.

The term "parvovirus" as used herein encompasses the family Parvoviridae, including autonomously-replicating parvoviruses and dependoviruses. The autonomous parvoviruses include members of the genera Parvovirus, Erythrovirus, Densovirus, Iteravirus, and Contravirus. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, snake parvovirus, and B19 virus. Other autonomous parvoviruses are known to those skilled in the art. See, e.g., Fields et al. Virology, 4th ed. Lippincott-Raven Publishers, Philadelphia, 1996. The genus Dependovirus contains the adeno-associated viruses (AAV), including but not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, avian AAV, bovine AAV, canine AAV, goat AAV, snake AAV, equine AAV, and ovine AAV.

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, snake AAV, avian AAV, bovine AAV, canine AAV, equine AAV, ovine AAV, goat AAV, shrimp AAV, and any other AAV now known or later discovered. See, e.g., Fields et al. Virology, 4th ed. Lippincott-Raven Publishers, Philadelphia, 1996. Additional AAV serotypes and clades have been identified recently. (See, e.g., Gao et al. J. Virol. 78:6381 (2004); Moris et al. Virol. 33:375 (2004). The genomic sequences of various serotypes of AAV, as well as the sequences of the native ITRs, Rep proteins, and capsid subunits are known in the art. Such sequences may be found in the literature or in public databases such as GenBank. See, e.g., GenBank Accession Numbers NC-002077, NC—001401, NC—001729, NC—001863, NC—001829, NC—001862, NC—000883, NC—001701, NC—001510, NC—-006152, NC—006261, AF063497, U89790, AF043303, AF028705, AF028704, J02275, J01901, J02275, X01457, AF288061, AH009962, AY028226, AY028223, AY631966, AX753250, EU285562, NC—001358, NC—001540, AF513851, AF513852 and AY530579; the disclosures of which are incorporated by reference herein for teaching AAV nucleic acid and amino acid sequences. See also, e.g., Bantel-Schaal et al. J. Virol. 73:939 (1999); Chiorini et al. J. Virol. 71:6823 (1997); Chiorini et al. J. Virol. 73:1309 (1999); Gao et al. Proc. Nat. Acad. Sci. USA 99:11854 (2002); Moris et al. Virol. 33:375 (2004); Muramatsu et al. Virol. 221:208 (1996); Ruffing et al. J. Gen. Virol. 75:3385 (1994); Rutledge et al. J. Virol. 72:309 (1998); Schmidt et al. J. Virol. 82:8911 (2008); Shade et al. J. Virol. 58:921 (1986); Srivastava et al. J. Virol. 45:555 (1983); Xiao et al. J. Virol. 73:3994 (1999); WO 00/28061, WO 99/61601, WO 98/11244; and U.S. Pat. No. 6,156,303; the disclosures of which are incorporated by reference herein for teaching AAV nucleic acid and amino acid sequences.

As used herein, an "asymmetric restriction site" refers to a nucleic acid sequence that is cleaved by a restriction enzyme (e.g., a restriction endonuclease) and whereupon cleavage at this site within double stranded DNA produces non-palindromic overhang sequences. Exemplary restriction enzymes that site-specifically cleave DNA at asymmetric restriction sites are known in the art and include, without limitation, Sfil and Pf/MI, among others.

As used herein, the term "about" refers to a value that is no more than 10% above or below the value being described. For example, the term "about 5 nM" indicates a range of from 4.5 nM to 5.5 nM.

A. Nucleic Acid Molecules

During replication and packaging of nucleic acid molecules encoding for viral genomes, the viral replication machinery initiates synthesis of the nucleic acid molecule at the inverted terminal repeat (ITR) and promotes incorporation of the nucleic acid molecule into a viral particle. In some instances, adjacent contaminant nucleic acids (e.g., prokaryotic origin of replication, prokaryotic promoter, and/ or an antibiotic resistance gene) are incorporated into the viral particle and can produce undesirable effects if transduced into a mammalian host cell. This invention is based, at least in part, on the discovery that inclusion of two spacers that flank ITRs of a nucleic acid molecule reduces the inadvertent packaging of contaminant nucleic acids. Here, we describe the generation of multiple nucleic acid molecules having two spacers that can be incorporated into a viral vector or a viral particle to reduce the number of viral particles containing contaminating nucleic acids. The required nucleic acid components, vectors, viral particles, host cells, and methods of producing viral particles are described herein.

The practice of the present invention will employ, unless otherwise indicated, conventional techniques of molecular biology (including recombinant techniques), microbiology, virology, and cell biology, which are within the skill of the art.

The present invention provides a means for generating nucleic acid molecules that enable the flexible, modular inclusion of two spacers linked to ITRs of a viral genome. A first nucleic acid molecule includes a first spacer (SS1), a first inverted terminal repeat (ITR1), a cloning site (CS), a second inverted terminal repeat (ITR2), and a second spacer (SS2) that are operably linked in a 5'-to-3' direction as: SS1-1TR1-CS-ITR2-SS2. The first nucleic acid molecule can be modified by cleavage of the nucleic acid molecule with a restriction endonuclease that recognizes the restriction site at the cloning site. Subsequently, a heterologous polynucleotide molecule (HPM), a eukaryotic promoter ($P_{Euk}$), a polyadenylation site (pA), and/or first and second homology arms (HR1 and HR2) can be introduced into the nucleic acid molecule at the cloning site. The following sections provide non-limiting examples of the spacer, heterologous polynucleotide molecule, eukaryotic promoter, and polyadenylation site that may be used in conjunction with the compositions described herein.

Spacers

Spacers can include naturally occurring nucleic acid molecules or synthetic nucleic acid molecules. Naturally occurring spacer molecules can be identified using on-line web tools, e.g., UCSC genome browser, and can be selected based on inherent features of the nucleic acid molecule, e.g., natural occurrence of a nucleic acid adjacent to a transcriptional start site. A spacer may be engineered to remove potentially negative features that may produce toxicity if introduced by a viral particle or suppress the functionality of the viral particle. Exemplary sources of toxicity and functionality suppressing features are found in contaminating nucleic acids frequently found adjacent to nucleic acids encoding for the viral genome to be packaged. These contaminating nucleic acids include, but are not limited to, prokaryotic (e.g., bacterial and baculoviral) nucleic acids (e.g., origin of replication, nucleic acids having greater than 2% CpG content, open reading frames, and transcription factor binding sites). In some embodiments, spacers are designed to minimize the inclusion of contaminating nucleic acids.

For example, in one embodiment a spacer does not contain an open reading frame (ORF) that is greater than about 100 amino acids. In another embodiment, a spacer contains an ORF that is less than about 50 amino acids. For example, a spacer can include an ORF that is less than 5 amino acids; less than 10 amino acids; less than 15 amino acids; less than 20 amino acids; less than 25 amino acids; less than 30 amino acids; less than 35 amino acids; less than 40 amino acids; less than 45 amino acids; less than 50 amino acids; less than 55 amino acids; less than 60 amino acids; less than 65 amino acids; less than 70 amino acids; less than 75 amino acids; less than 80 amino acids; less than 85 amino acids; less than 90 amino acids; less than 95 amino acids; or less than 100 amino acids. ORFs can be determined using on-line nucleic acid sequence analysis tools, e.g., BLAST or UCSC genome browser.

In other embodiments, the spacer has a total CpG content that is less than 1% of tile total genomic nucleic acid sequence (e.g., less than 0.5% CpG content, less than 0.2% CpG content; less than 0.05% CpG content; or less than 0.02% CpG content of the total spacer nucleic acid sequence). In some embodiments, the spacer does not contain greater than 2% CpG content across the length of the spacer nucleic acid. For example, for a spacer having a length of 3.0 Kb, the total number of CpG dinucleotides in the spacer nucleic acid may not exceed 60 CpG dinucleotides and is preferably less than 30 CpG dinucleotides.

In another embodiment, the spacer does not contain contaminant nucleic acids that are prokaryotic or baculoviral in origin. For example, the spacer does not contain prokaryotic nucleic acids that provide a transcription factor binding site for a prokaryotic transcription factor or an origin of replication recognized by a prokaryotic replication machinery. The spacer further does not include a selectable marker, e.g., an antibiotic resistance gene that can be expressed in prokaryotes. In other embodiments, the spacer does not include baculoviral nucleic acids that contain baculoviral transcription factor binding sites or baculoviral open reading frames.

In some embodiments, the spacer is an intron, or a fragment thereof. The intron may be from a vertebrate genome (e.g., a mammalian genome, e.g., a human genome). For example, the spacer is an intron associated with a gene of interest (e.g., where the heterologous polynucleotide encodes FIX, the intron is from an intron present in the FIX gene) or from another gene. Accordingly, other untranslated (non-protein encoding) regions of nucleic acid, such as introns found in cognate (related) genes (the heterologous polynucleotide encodes all or a portion of the same protein encoded by the gene) and non-cognate (unrelated) genes (the heterologous polynucleotide encodes a protein that is distinct from the protein encoded by the gene) can also function as a spacer.

In other embodiments, the spacer is an enhancer. For example, the spacer is a tissue-specific enhancer or a ubiquitously expressed enhancer. In an embodiment, the spacer is a tissue-specific enhancer, e.g., muscle specific (including cardiac, skeletal and/or smooth muscle specific), neural tissue specific (including brain-specific), eye specific (including retina-specific and cornea-specific), liver specific, bone marrow specific, pancreatic specific, spleen specific, and lung specific enhancer elements. In another embodiment, the spacer is a liver-specific enhancer, e.g., an apoE/apoC1 or an apoCIII enhancer.

An exemplary spacer includes nucleic acids from or adjacent to the human ubiquitin C locus. In some embodiments, a first and/or second spacer includes the nucleic acid sequence of SEQ ID NO: 1. In some embodiments, a first and/or second spacer includes the nucleic acid sequence of SEQ ID NO: 2. In some embodiments, a first and/or second spacer has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 1. In some embodiments, a first and/or second spacer has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 2. A spacer may contain a portion of SEQ ID NO: 1 or SEQ ID NO: 2, such as a nucleic acid sequence that is about half the length of SEQ ID NO: 1 or SEQ ID NO: 2. For instance, in some embodiments a first and/or second spacer includes the nucleic acid sequence of SEQ ID NO: 3, or a sequence that has at least 85% sequence identity (e.g., at least 90%, 91%, 92%, 93%, 94%, 95%, 96%, 97%, 98%, 99%, or 100% sequence identity) to SEQ ID NO: 3. In some embodiments, a first and/or second spacer includes the nucleic acid sequence of SEQ ID NO: 4, or a sequence that has at least 85% sequence identity (e.g., at least 90%, 91%, 92%, 93%, 94%, 95%, 96%, 97%, 98%, 99%, or 100% sequence identity) to SEQ ID NO: 4. For example, a first spacer may contain the nucleic acid sequence of SEQ ID NO: 1, or a sequence that has at least 85% sequence identity (e.g., at least 90%, 91%, 92%, 93%, 94%, 95%, 96%, 97%, 98%, 99%, or 100% sequence identity) to SEQ ID NO: 1, and a second spacer may include the nucleic acid sequence of SEQ ID NO: 2, or a sequence that has at least 85% sequence identity (e.g., at least 90%, 91%, 92%, 93%, 94%, 95%, 96%, 97%, 98%, 99%, or 100% sequence identity) to SEQ ID NO: 2. In another embodiment, a first spacer may contain the nucleic acid sequence of SEQ ID NO: 3, or a sequence that has at least 85% sequence identity (e.g., at least 90%, 91%, 92%, 93%, 94%, 95%, 96%, 97%, 98%, 99%, or 100% sequence identity) to SEQ ID NO: 3, and a second spacer may include the nucleic acid sequence of SEQ ID NO: 4, or a sequence that has at least 85% sequence identity (e.g., at least 90%, 91%, 92%, 93%, 94%, 95%, 96%, 97%, 98%, 99%, or 100% sequence identity) to SEQ ID NO: 4. Regions of the human ubiquitin C locus that can be incorporated into spacers may be selected based on the presence or absence of any of the aforementioned criteria (e.g., length of the ORF or % CpG content) or the nucleic acid sequence may be modified to remove or reduce, e.g., the length of the ORF or % CpG content.

A spacer may include all or a portion of a nucleic acid sequence that facilitates the covalent integration of the nucleic acid construct to which the spacer is attached into a heterologous nucleic acid molecule, such as a circular or linear host cell chromosome. For instance, a spacer may contain all or a portion of the human AAV integration site (AAVS1, SEQ ID NO: 6), or a sequence that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 6. The AAVS1 locus naturally occurs on cytogenetic band 13 of the q arm within human chromosome 19 (19q13), and is frequently a site of AAV genome integration. The AAVS1 site contains a region that bears a high degree of sequence similarity to naturally occurring Rep-binding motifs within AAV genomes, which provides a basis for Rep-mediated insertion of the viral genome into the human chromosome. Spacers may contain a portion of the AAVS1 sequence that is similar in sequence to a Rep-binding site of an AAV genome, such as a portion of the AAVS1 site that has at least 85% sequence identity (e.g., at least 90%, 91%, 92%, 93%, 94%, 95%, 96%, 97%, 98%, 99%, or 100% sequence identity) to a Rep-binding motif. For instance, a spacer may contain a minimal portion of the AAVS1 site that promotes insertion of neighboring DNA into a chromosome of a host cell, such as human chromosome 19. In some embodiments, the spacer contains the Rep-binding sequence GAGCGAGCGAGCGC (SEQ ID NO: 5) that naturally occurs in the middle of the human AAVS1 locus. In other embodiments, spacers contain a sequence that has at least 85% sequence identity (e.g., at least 90%, 91%, 92%, 93%, 94%, 95%, 96%, 97%, 98%, 99%, or 100% sequence identity) to SEQ ID NO: 5. Spacers may contain a portion of the AAVS1 locus, such as a portion that contains at least 100 kb (e.g., at least 100 kb, 200 kb, 300 kb, 400 kb, 500 kb, 600 kb, 700 kb, 800 kb, 900 kb, 1,000 kb, 1,100 kb, 1,200 kb, 1,300 kb, 1,400 kb, 1,500 kb, 1,600 kb, 1,700 kb, 1,800 kb, 1,900 kb, 2,000 kb, 2,100 kb, 2,200 kb, 2,300 kb, 2,400 kb, 2,500 kb, 2,600 kb, 2,700 kb, 2,800 kb, 2,900 kb, or 3,000 kb) of SEQ ID NO: 6. In some embodiments, a first and/or second spacer contains a nucleic acid sequence that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 6 or a portion thereof, e.g., wherein the portion includes a nucleic acid sequence that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 5.

Spacers may contain the reverse complement of any of the polynucleotides described above. For instance, in some embodiments a first and/or second spacer includes the nucleic acid sequence of SEQ ID NO: 7, which is the reverse complement of SEQ ID NO: 1. In some embodiments, a first and/or second spacer includes the nucleic acid sequence of SEQ ID NO: 8, which is the reverse complement of SEQ ID NO: 2. In some embodiments, a first and/or second spacer has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 7. In some embodiments, a first and/or second spacer has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 8. A spacer may contain a portion of SEQ ID NO: 7 or SEQ ID NO: 8, such as a nucleic acid sequence that is about half the length of SEQ ID NO: 9 or SEQ ID NO: 10. For instance, in some embodiments a first and/or second spacer includes the nucleic acid sequence of SEQ ID NO: 9, or a sequence that has at least 85% sequence identity (e.g., at least 90%, 91%, 92%, 93%, 94%, 95%, 96%, 97%, 98%, 99%, or 100% sequence identity) to SEQ ID NO: 9. In some embodiments, a first and/or second spacer includes the nucleic acid sequence of SEQ ID NO: 10, or a sequence that has at least 85% sequence identity (e.g., at least 90%, 91%, 92%, 93%, 94%, 95%, 96%, 97%, 98%, 99%, or 100% sequence identity) to SEQ ID NO: 10. For example, a first spacer may contain the nucleic acid sequence of SEQ ID NO: 7, or a sequence that has at least 85% sequence identity (e.g., at least 90%, 91%, 92%, 93%, 94%, 95%, 96%, 97%, 98%, 99%, or 100% sequence identity) to SEQ ID NO: 7, and a second spacer may include the nucleic acid sequence of SEQ ID NO: 8, or a sequence that has at least 85% sequence identity (e.g., at least 90%, 91%, 92%, 93%, 94%, 95%, 96%, 97%, 98%, 99%, or 100% sequence identity) to SEQ ID NO: 8. In another embodiment, a first spacer may contain the nucleic acid sequence of SEQ ID NO: 9, or a sequence that has at least 85% sequence identity (e.g., at least 90%, 91%, 92%, 93%, 94%, 95%, 96%, 97%, 98%, 99%, or 100% sequence identity) to SEQ ID NO: 9, and a second spacer may include the nucleic acid sequence of SEQ ID NO: 10, or a sequence that has at least 85% sequence identity (e.g., at least 90%, 91%, 92%, 93%, 94%, 95%, 96%, 97%, 98%, 99%, or 100% sequence identity) to SEQ ID NO: 10. In some embodiments, a first and/or second spacer contains a nucleic acid sequence that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 11, which is the reverse complement of SEQ ID NO: 5. In some embodiments, a spacer contains a portion of SEQ ID NO: 5 that includes a nucleic acid sequence that has at least 85% sequence identity (e.g., at least 90%, 91%, 92%, 93%, 94%, 95%, 96%, 97%, 98%, 99%, or 100% sequence identity) to the nucleic acid sequence of SEQ ID NO: 12, which is the reverse complement of the Rep-binding motif depicted in SEQ ID NO: 6. These sequences are provided in Table 1, below:

TABLE 1

Exempary DNA sequences useful for incorporation into spacers

| SEQ ID NO. | Description | Sequence |
| --- | --- | --- |
| 1 | Portion of human ubiquitin C locus | GTAAAAAAAGGCATAGCTAACAAGGTGTGGAAAAAGAATTAGTGGTT AGAGAGTGAGCTATTCGTTGAAACAATTGCGTTCTTGAAACAATTCT TGCTGGTAAAATGTCACATTTTATGTGACTACAGGTGGAGGATTGGC ACATAACCTAACCAGTGGGGGAAACAATTGACCTCTGGATTTGTCCA AGTGTATAGTAGCATTTGCCCAATCGAATGGTCCTGGTAAGGTGTTA ATGTTGACTAGAACCAAAGGTGGAAGTTGCAGGGAAACTGGTTTAGT ACAAGGGTGGACACCAGGCAGTCATCCAGAGGCCCATTAAAGGCCTT GGAATGTTTTTCCGAAGGAGAATCACTCCCTCTTCTCTCGCTTAAAG TTTTAGGGGATTCATGAACAGCTGCTGTGGGATAGTTTCATGTCCCT AGCAATTGTAAAGCAACTGAGGGTGGCTTAAACCAGTTTTAGCTTTA GGGTTAGGGTTACTGGACTAAAATTTGAGAAATTCATAAATCTTAAG GAAATCCATTGTGAGTTTTCATTATGAGTGCATCCAATGTATAATTT CCATGACCCTCCCATGCAAGTGAGCATGTGAATCAGGAAACGTTACA AGAACCCAACAAACTCAACCACTACTAGACAGGCGATCACTTCCAGT TAGTATGCAACTTTCTGTGTAATTTTAGTTACCATTAAAATCTGGAT GACCTTAGTGTAAGGAAAAAAATACCTTGAATAGTGTTAAAGATGTAC ACTTGGTGTCAGGCATTGTAACATTGATAAATCTGTGTAAGGTGCTT TTTGAAAACTTCAAAGCTGCATCAAGTCAAGTACAAGAAAGGCCATG GCTGCTAAAGCTGTTGAAGATGTGGGATGGAACTGGGTCACATTGGT GTTAACAGCGTTGTGCAGAGCCGGCAGGATCTTGGTGTGAGCGAACA TTAGTCTATTTAATAAAGCTGTGTGAATGTTGTAGAGGTGAGGATGC TCACTTGAAAACTCACTGAAGAACACTTGGCCCCTTGAACTAAAGTG CTTCTATCAAGTTCAGTGAGAAATTCCGAATTACAAGCATAGGTACT AGAAAAGTTTTGAAAAGCAGTATAGAGCAACATAAGCACATTCATAA AATTAGTGATGTAGAAAGTGAAATTTCCACGTATGGTCACTCCCAGA GAAAAAAAATACGTTTATTTACCTTTTTTAAAAATAGGGGATTTCAG GCCGGGTGAGGTGGCTCACGCCTGTAATCCCAGCACTTTGGGAGGCC CAGGTGGGCGGATCACCTGAGGTCAGGAGTTGGAGGGATGGCAAATC CCATCTCTACAAAATATACAAAAAAATAGCTGGGTGTGTTGGCAGGC GCCTGTAATCCCAGCTACTCGGAAGGCTGAGGCAGGAGAATCCCTGG AACCAGGGATGTGGAGGTTGCAGTGAGCCGAGATTGTGTAACTGCAT TCCAGCCTGGGCAACAAGAGCAAGACTCCGTATCAGGAAAAAAAAAA GGGGGGGTTGGATTTCGCTTGTTGCATAGGTTGGTCTCAAACTCCTG GCCTCAAGTGATTCTCCTGCCTCTGCCTCCCAAAGTGCTGAGATTAC AGGTGTGAGGCACCATGCCAGGTCTCTTACTGTTTGTAATTAAATAC ATACACATTTTGTGTGTTTGTGTGCACCTTTATAAAGTCAAAGGTGA |

TABLE 1-continued

Exemplary DNA sequences useful for incorporation into spacers

| SEQ ID NO. | Description | Sequence |
|---|---|---|
| | | TAGTAACCCATTTAAGTTCCTACTCAATTTTACTTTCCAGGGATAAC<br>TAACTACTTTTTCTTTTTGAGATGGAGTCTCGCTGTGTAGCCCAGGC<br>TGGAGTGCAGTGGCACCATCTCGGCTCACTGCAAGCTCCTCCTCCCT<br>GGTTCACGCTATTCTCCTGCCTCAGCCTCCCCAACAACTAGGACTAC<br>AGGCTCACCTCGCCATACCTGGCTAATTTTTTGTATTTTTAGTAGAG<br>ACAGGGTTTCACTGTGTTAGCCAGGATGGTCTCGATCTCCTGACCTT<br>GTGATCCGCCTGCCTCTGCCTCCCAAAGTGCTGGGATTACAGGCATG<br>AGCAACCTCACCCAGCTGGGATAACTACTTTTTACAGGTTGATATTC<br>TTTTGGACTTTTCCCCTGTGTAAAAATATACTATATTTGTTATGTAC<br>ATATTATGTACATACAGACACAAATTGGACCATTCTCAGTATAATGA<br>TTCTCAGGTTTTTTTTTTTTTTTGAGGTGGGGAACTAGATAATTAT<br>GGACATCTTTCCATACTAGCATATCAATATCTACCTCATTCTTTTTA<br>ATATTTTTGCTAGTATTCCATTGTATGAATGTCCTATGATTTACTTA<br>ACCTGTCCATCAATATTTGTTTCCAGGTTTTTGCTATTATAATGCTG<br>CTGCAAAGTACATCCTCACACATCTTTATTTTGTCTATTCATATTTC<br>TGTAAGATAGGTTACTAAAGTTGGAACTGCCAAATTAACACTATCAT<br>ACTATTTTGTTTTTAATTTTAATTTTTTAAAAAATGTAAATGTGC<br>AATTTCAAGAGGAGAAACTTGAACACAAGGAGCAAAATCTATTTTTA<br>TAACATCCTATTAAAAGCTTGCTTTACATAAAGATTTTGAAAGAATA<br>GCATAAATACAAGATTTCTATTTTAATTGGATTCTTAGGGCTAATAA<br>AATAATCAGCCTTAGCACTTATTTATTTATTTTTTTGAGAGGGAGT<br>CTCGCTCTGTTGTCCATGCTGGAGTGCAGTGGCGTGATCTCGGCTCA<br>CTGCAAGCTCCACCTCATGAGTTCACACCATTCTCCTGCCTCAGTCT<br>CCCGAGTAGCTGGGACTCCAGGCGCCCTCTACAAAGCCCGTCTAATT<br>TTTTTTGTATTTTTAGTAGAGACAGGGTTTCACTGTGTTAGCCAGGA<br>TGGTCTTGATCTCCTGACCTTGTGATCTGCCCGCCTCGGCCTCCCAA<br>AGTGCTGGGATTATAGGCTTGAGCCACTGCTCCCGGCCAGCACTTAT<br>TTTTATAATTCTTCATGATTACTGTGTTACTGTCCCATG |
| 2 | Portion of human<br>ubiquitin C locus | ATATTTCTCAATTTTTAAATTTTTCAAAAAAATTAATCCTTAATGTG<br>CATATTTTTGAATTGTTAATATAACTTTTTGAGGTGATGTCTTCATG<br>TGTTTCAACTACTTAAAAACTTTTAAACAGTATATAATAAAAAATCT<br>TCCAGGCCACTCACACCTGTAATCCCAGCACTTTGGGAGGCTGAGGT<br>GGGCAGATCACCTGAGGGCAGGAGTTCGAGACCAGCCTGGCCAATAT<br>ATATATATTCATATATTCATATATATATATATATTCATATATTCATA<br>TATATATATTCATATATTCATATATATATATATATATATATAGCA<br>AAACCTCATCTCTAATAAAATACAAAAATTAGCTGAGCGTGGTGATG<br>GATGCCTGTAGTCCCAGCTACTCGGGAGGCTGAGGCAGGAGAATCTC<br>TTGAACCTGGGAGGTGGAGGTTGCAGTGAGCTGAGATGGTGCCACTG<br>CCCTCCAGCCTGAGTGACAGAGCGAGACTCGGTCTCAAAAAAAAAC<br>AACAAAAAAATCTTCCATCCTTGTCTCCCATCCACCCCTTCCCCCCA<br>GCATGTACTTGCAGACTTTATGCATATACAGTGAGTACTGTATATAC<br>ACAAATAATAAAAAAATCATATATATAATATATGTAATTCCCCTTTA<br>CATGAAAGGTAGCACACTGGTCTGTACAGTCTGTCTGCACTGTGCTA<br>TTTCACTTTATATTTTTATAGTTTGACAGAGTTCTAACATTTCTTTT<br>TTTTTTTTTTTAACAGAGTCTTGTTCCTGATTGTTAAATTTTAAAGC<br>ATCCTAAAGTTTGGTTTCACACTTGAATGAATACCATGTAAGGATTC<br>ACTTACATAGATGTGGTTGCCTGAATCTTAAGAATAAAATAACATTG<br>TTTGTATTTATTTAAATTAGTGTTCCTTTTATGGTTTGCCTGAAAGC<br>ACAACAAAATCCTCACCAAGATATTACAATTATGACTCCCATACAGG<br>TAAACTGTTTAGAGATTGGCAAGCACCTTTTAATGAAAGGAGTCAGC<br>CAGCTTAGTGTGCAGTATTTATTTCTGCCGGAAGAGGGAGCTTCAGG<br>GACAGACTTTGGTTTAGTCATGAAGCCTCCAGCACTCCCAAGCGGTT<br>GTGGTTGACCAAGCAATTTATGCTTTTACCTTTCTACTTCCAGAGGC<br>TTGTTTACTTATCAGTAAGCATTAATTTAGTGTCCCCTCAGATGCCT<br>TTTACTTTCTTCTTTTCTGCCTAGAATAAGCTGCTCTTCCAATTTTG<br>CAGCTACATGTTTCCACCCCAGTTGGAATTTCTCCATAACATCCATT<br>GTAGCTATCCTTCAATCTACAGCCTCTATTTCCTGTTATAGCTGGTC<br>AGGTCTAATCCCTCAAAATACTCTGTCCCCTGCTTCCCTTATCTGCT<br>GGCCACCTTTTTCCCCCACATACACACTGCCATGTCCCACCCTTCAC<br>TCAAGTTGTTCCCTGCCACCTCAACAAATTTAAGTCCATAAAATAGA<br>GTAAGTGTTCCTGACTGTTAAATTTTAAAGCATCCCAAAGTCTGATT<br>TCACACTCGAATGAATACTATGTACGGATTCATTTACATAGATGCGG<br>TTGCATGAGTCTTAACAAAAAAATAACATTATTTGTATTTATTCAAA<br>GTACTGTCAAGATATAATGTCAAGACCTAATTCAAAGGTTCCACAAA<br>GCCTTCCTTGACTGCCCCAACGAAGATTATCCATTTTCCCTGAAAT<br>CCCATTGACTTTCTATTTTGTAAGGAGGCTCGTGAGACTCTGTCTA<br>AAAACAAAACAAAACAAAAAGAAACAATCAAACGGCTTGCTTCTGTT<br>CTTTGATCTGCTAGTAAGCAAAAATTACACATGGTGACAGGAGCTAT<br>GTGAGGCTGTCAGGTTGAATGGGAGGAGTTTGGGATCCTGCTTGTGG<br>ATGGTTGGAAGAGGCTTTCGGGAAAGACAGTATTTATGTGAGACCTG<br>GAAGATGGGCCTTAGCTTTGCAGAAGGTGGAGAGGCAGGAAATAGCA<br>CGGGGGCCCTGGGGCTGGAAGACTTGGGCATATTTGAGGAACAGAAA<br>GGAGACCAGCATAACTGAGGTGGGAAAAGCATGTGAAGAGATGGGGC<br>TGGAGGAGGCCGGGAGTGGTGGCTCACGCCTGTAATCCCAGCACTTT<br>GGGAGGCCAAGGCAGGCGGATCATGAGCTCAGGAGATTGAGACCATC |

TABLE 1-continued

Exempary DNA sequences useful for incorporation into spacers

| SEQ ID NO. | Description | Sequence |
|---|---|---|
|  |  | CTGGCTAACACGGTGAAACCCCTCTCTACTAAAAATACAAAAAAAA<br>AAAAAAAAAAAATTAGCTGGGCGTGGTGGCAGGAGCCTGTAGTCCCA<br>GCTACCTGGGAGGCTGAGGCAGGAGAATGGCGTGAACCTGGAAGGCT<br>GAGCTTGCAGTGAGCCGAGATTGCACCACTGCACTCCAGCCTGGGAG<br>ACAGAGAGAGACTCCCTCTCAAAAAAACAAACAAACGAAACAAAACA<br>AAACAAAAATTAGCCAGGCGTGGTGGTATGCACCTGTAATCCCAGCT<br>ACTCGGGAGGTTGAGGCAGGAGAAACGCTTGAACTCAGGAGGCGGAG<br>GTTGCAGTGAGCCGAGACTGCGCCACTGCACTCCAGCCTCAACCTCC<br>CCAGCTGAAGCCATCCTCTTGCCTCAGCCTCCTAAGTAGCTGGGACT<br>ACAGGCGCGCACCTCCAGGCTTGGCTCTTATTCTTTTTATTGTTTTT<br>GAAACTATAGAACCTATTTTTAAAAAATGTTTTGGTTGTTTTTATTG<br>CTGCTTTTCCTTTTGGGGTTAGAACACAAGTTTTGATGGGAAACAGG<br>TTAGAACACATTCATCTCTTCCCATAGCGATGGTCATAGAAAAACGG<br>GGCATATTTATAAACTCTCAGTTGATCTTAAAATGTGCAAAAGCTGC<br>CGAACTCCTGGGAGTGA |
| 3 | Portion of human<br>ubiquitin C locus | GAAAAGGGGGGTTGGATTTCGCTTGTTGCATAGGTTGGTCTCAAAC<br>TCCTGGCCTCAAGTGATTCTCCTGCCTCTGCCTCCCAAAGTGCTGAG<br>ATTACAGGTGTGAGGCACCATGCCAGGTCTCTTACTGTTTGTAATTA<br>AATACATACACATTTTGTGTGTTTGTGTGCACCTTTATAAAGTCAAA<br>GGTGATAGTAACCCATTTAAGTTCCTACTCAATTTTACTTTCCAGGG<br>ATAACTAACTACTTTTTCTTTTTGAGATGGAGTCTCGCTGTGTAGCC<br>CAGGCTGGAGTGCAGTGGCACCATCTCGGCTCACTGCAAGCTCCTCC<br>TCCCTGGTTCACGCTATTCTCCTGCCTCAGCCTCCCCAACAACTAGG<br>ACTACAGGCTCACCTCGCCATACCTGGCTAATTTTTTGTATTTTTAG<br>TAGAGACAGGGTTTCACTGTGTTAGCCAGGATGGTCTCGATCTCCTG<br>ACCTTGTGATCCGCCTGCCTCTGCCTCCCAAAGTGCTGGGATTACAG<br>GCATGAGCAACCTCACCCAGCTGGGATAACTACTTTTTACAGGTTGA<br>TATTCTTTTGGACTTTTCCCCTGTGTAAAAATATACTATATTTGTTA<br>TGTACATATTATGTACATACAGACACAAATTGGACCATTCTCAGTAT<br>AATGATTCTCAGGTTTTTTTTTTTTTTTGAGGTGGGGAACTAGATA<br>ATTATGGACATCTTTCCATACTAGCATATCAATATCTACCTCATTCT<br>TTTTAATATTTTGCTAGTATTCCATTGTATGAATGTCCTATGATTT<br>ACTTAACCTGTCCATCAATATTTGTTTCCAGGTTTTTGCTATTATAA<br>TGCTGCTGCAAAGTACATCCTCACACATCTTTATTTTGTCTATTCAT<br>ATTTCTGTAAGATAGGTTACTAAAGTTGGAACTGCCAAATTAACACT<br>ATCATACTATTTTGTTTTTTAATTTTAATTTTTTAAAAAATGTAAAA<br>TGTGCAATTTCAAGAGGAGAAACTTGAACACAAGGAGCAAAATCTAT<br>TTTTATAACATCCTATTAAAAGCTTGCTTTACATAAAGATTTTGAAA<br>GAATAGCATAAATACAAGATTTCTATTTTAATTGGATTCTTAGGGCT<br>AATAAAATAATCAGCCTTAGCACTTATTTATTTATTTTTTTGAGAG<br>GGAGTCTCGCTCTGTTGTCCATGCTGGAGTGCAGTGGCGTGATCTCG<br>GCTCACTGCAAGCTCCACCTCATGAGTTCACACCATTCTCCTGCCTC<br>AGTCTCCCGAGTAGCTGGGACTCCAGGCGCCCTCTACAAAGCCCGTC<br>TAATTTTTTTGTATTTTTAGTAGAGACAGGGTTTCACTGTGTTAGC<br>CAGGATGGTCTTGATCTCCTGACCTTGTGATCTGCCCGCCTCGGCCT<br>CCCAAAGTGCTGGGATTATAGGCTTGAGCCACTGCTCCCGGCCAGCA<br>CTTATTTTTATAATTCTTCATGATTACTGTGTTACTGTCCCATG |
| 4 | Portion of human<br>ubiquitin C locus | ATATTTCTCAATTTTTAAATTTTTCAAAAAAATTAATCCTTAATGTG<br>CATATTTTTGAATTGTTAATATAACTTTTTGAGGTGATGTCTTCATG<br>TGTTTCAACTACTTAAAAACTTTTAAACAGTATATAATAAAAAATCT<br>TCCAGGCCACTCACACCTGTAATCCCAGCACTTTGGGAGGCTGAGGT<br>GGGCAGATCACCTGAGGGCAGGAGTTCGAGACCAGCCTGGCCAATAT<br>ATATATATTCATATATTCATATATATATATATATTCATATATTCATA<br>TATATATATTCATATATTCATATATATATATATATATATATATAGCA<br>AAACCTCATCTCTAATAAAATACAAAAATTAGCTGAGCGTGGTGATG<br>GATGCCTGTAGTCCCAGCTACTCGGGAGGCTGAGGCAGGAGAATCTC<br>TTGAACCTGGGAGGTGGAGGTTGCAGTGAGCTGAGATGGTGCCACTG<br>CCCTCCAGCCTGAGTGACAGAGCGAGACTCGGTCTCCAAAAAAAAAC<br>AACAAAAAAATCTTCCATCCTTGTCTCCCATCCACCCCTTCCCCCCA<br>GCATGTACTTGCAGACTTTATGCATATACAGTGAGTACTGTATATAC<br>ACAAATAATAAAAAAATCATATATATAATATATGTAATTCCCCTTTA<br>CATGAAAGGTAGCACACTGGTCTGTACAGTCTGTCTGCACTGTGCTA<br>TTTCACTTTATATTTTATAGTTTGACAGAGTTCTAACATTTCTTTT<br>TTTTTTTTTTAACAGAGTCTTGTTCCTGATTGTTAAATTTTAAAGC<br>ATCCTAAAGTTTGGTTTCACACTTGAATGAATACCATGTAAGGATTC<br>ACTTACATAGATGTGGTTGCCTGAATCTTAAGAATAAAATAACATTG<br>TTTGTATTTATTTAAATTAGTGTTCCTTTTATGGTTTGCCTGAAAGC<br>ACAACAAAATCCTCACCAAGATATTACAATTATGACTCCCATACAGG<br>TAAACTGTTTAGAGATTGGCAAGCACCTTTTAATGAAAGGAGTCAGC<br>CAGCTTAGTGTGCAGTATTTATTTCTGCCGGAAGAGGGAGCTTCAGG<br>GACAGACTTTGGTTTAGTCATGAAGCCTCCAGCACTCCCAAGCGGTT<br>GTGGTTGACCAAGCAATTTATGCTTTTACCTTTCTACTTCCAGAGGC<br>TTGTTTACTTATCAGTAAGCATTAAATTTAGTGTCCCCTCAGATGCCT<br>TTTACTTTCTTCTTTTCTGCCTAGAATAAGCTGCTCTTCCAATTTTG |

TABLE 1-continued

Exemplary DNA sequences useful for incorporation into spacers

| SEQ ID NO. | Description | Sequence |
|---|---|---|
|  |  | CAGCTACATGTTTCCACCCCAGTTGGAATTTCTCCATAACATCCATT GTAGCTATCCTTCAATCTACAGCCTCTATTTCCTGTTATAGCTGGTC AGGTCTAATCCCTCAAAATACTCTGTCCCCTGCTTCCCTTATCTGCT GGCCACCTTTTTCCCCCACATACACACTGCCATGTCCCACCCTTCAC TCAAGTTGTTCCCTGCCACCTCAACAAATTTAAGTCCATAAAAC |
| 5 | Rep-binding site of human AAVS1 locus | GAGCGAGCGAGCGC |
| 6 | Human AAVS1 locus | GAGGGTTTCAGCGCTAAAACTAGGCTGTCCTGGGCAAACAGCATAAG CTGGTCACCCCACACCCAGACCTGACCCAAACCCAGCTCCCCTGCTT CTTGGCCACGTAACCTGAGAAGGGAATCCCTCCTCTCTGAACCCCAG CCCACCCCAATGCTCCAGGCCTCCTGGGATACCCCGAAGAGTGAGTT TGCCAAGCAGTCACCCCACAGTTGGAGGAGAATCCACCCAAAAGGCA GCCTGGTAGACAGGGCTGGGGTGGCCTCTCGTGGGGTCCAGGCCAAG TAGGTGGCCTGGGGCCTCTGGGGATGCAGGGGAAGGGGGATGCAGG GGAACGGGGATGCAGGGGAACGGGGCTCAGTCTGAAGAGCAGAGCCA GGAACCCCTGTAGGGAAGGGGCAGGAGAGCCAGGGGCATGAGATGGT GGACGAGGAAGGGGGACAGGGAAGCCTGAGCGCCTCTCCTGGGCTTG CCAAGGACTCAAACCCAGAAGCCCAGAGCAGGGCCTTAGGGAAGCGG GACCCTGCTCTGGGCGGAGGAATATGTCCCAGATAGCACTGGGGACT CTTTAAGGAAAGAAGGATGGAGAAAGAGAAAGGGAGTAGAGGCGGCC ACGACCTGGTGAACACCTAGGACGCACCATTCTCACAAAGGGAGTTT TCCACACGGACACCCCCCTCCTCACCACAGCCCTGCCAGGACGGGGC TGGCTACTGGCCTTATCTCACAGGTAAAACTGACGCACGGAGGAACA ATATAAATTGGGGACTAGAAAGGTGAAGAGCCAAAGTTAGAACTCAG GACCAACTTATTCTGATTTTGTTTTTCCAAACTGCTTCTCCTCTTGG GAAGTGTAAGGAAGCTGCAGCACCAGGATCAGTGAAACGCACCAGAC AGCCGCGTCAGAGCAGCTCAGGTTCTGGGAGAGGGTAGCGCAGGGTG GCCACTGAGAACCGGGCAGGTCACGCATCCCCCCCTTCCCTCCCACC CCCTGCCAAGCTCTCCCTCCCAGGATCCTCTCTGGCTCCATCGTAAG CAAACCTTAGAGGTTCTGGCAAGGAGAGAGATGGCTCCAGGAAATGG GGGTGTGTCACCAGATAAGGAATCTGCCTAACAGGAGGTGGGGGTTA GACCCAATATCAGGAGACTAGGAAGGAGGAGGCCTAAGGATGGGGCT TTTCTGTCACCAATCCTGTCCCTAGTGGCCCCACTGTGGGGTGGAGG GGACAGATAAAAGTACCCAGAACCAGAGCCACATTAACCGGCCCTGG GAATATAAGGTGGTCCCAGCTCGGGGACACAGGATCCCTGGAGGCAG CAAACATGCTGTCCTGAAGTGGACATAGGGGCCCGGGTTGGAGGAAG AAGACTAGCTGAGCTCTCGGACCCCTGGAAGATGCCATGACAGGGGG CTGGAAGAGCTAGCACAGACTAGAGAGGTAAGGGGGGTAGGGGAGCT GCCCAAATGAAAGGAGTGAGAGGTGACCCGAATCCACAGGAGAACGG GGTGTCCAGGCAAAGAAAGCAAGAGGATGGAGAGGTGGCTAAAGCCA GGGAGACGGGGTACTTTGGGGTTGTCCAGAAAAACGGTGATGATGCA GGCCTACAAGAAGGGGAGGCGGGACGCAAGGGAGACATCCGTCGGAG AAGGCCATCCTAAGAAACGAGAGATGGCACAGGCCCCAGAAGGAGAA GGAAAAGGGAACCCAGCGAGTGAAGACGGCATGGGGTTGGGTGAGGG AGGAGAGATGCCCGGAGAGGACCCAGACACGGGGAGGATCCGCTCAG AGGACATCACGTGGTGCAGCGCCGAGAAGGAAGTGCTCCGGAAAGAG CATCCTTGGGCAGCAACACAGCAGAGACAAGGGGAAGAGGGAGTGG AGGAAGACGGAACCTGAAGGAGGCGGCAGGGAAGGATCTGGGCCAGC CGTAGAGGTGACCCAGGCCACAAGCTGCAGACAGAAAGCGGCACAGG CCCAGGGGAGAGAATGCAGGTCAGAGAAAGCAGGACCTGCCTGGGAA GGGGAAACAGTGGGCCAGAGGCGGCGCAGAAGCCAGTAGAGCTCAAA GTGGTCCGGACTCAGGAGAGAGACGGCAGCGTTAGAGGGCAGAGTTC CGGCGGCACAGCAAGGGCACTCGGGGGCGAGAGGAGGGCAGCGCAAA GTGACAATGGCCAGGGCCAGGCAGATAGACCAGACTGAGCTATGGGA GCTGGCTCAGGTTCAGGAGAGGGCAGGGCAGGGAAGGAGACAAAGTC CAGGACCGGCTGGAGGGGCTCAACATCGGAAGAGGGGAAGTCGAGGG AGGGATGGTAAGGAGGACTGCATGGGTCAGCACAGGCTGCCAAAGCC AGGGCCAGTTAAAGCGACTCCAATGCGGAAGAGAGTAGGTCGAAGGG GAATGGTAAGGAGGCCTGGGGCAGAGTGGTCAGCACAGAGTGGCTAA GCCCAGGGCCAGTTGAAGCGGCTCCAATTCGGAAGTGGGGTGGTCGA AGGGGAATGGTAAGGGGGACTGGGACGGGGTGTCAGCATAGGGTGGC AAAGCCCAGGGCCAGGAACGACGGGGCGGATCGAGACTGGCAACGGG GAAGGAGGATGCCCCAGGTGGCGCAGCAGAGGGTGGACCTGGCCCCG GGAGACGCCGGGCGGGGGCGCTGACCTGGTGCAGGGCGCTGATACC GTCGGCGTTGGTGGAGTCCAGCACGGCGCGGGCGGGCGGCGGCGCGG CGGGGTCGAGCTCGGCGCCGGGCCAGGGTCGGCGGCGCGCAGCATC AGACGCGCCTCGTCAGGTCGCCGCCCGCACAGGCCGCCAGGAACTC GGCGGCGCGCTCGAAGCGGACGGTGCGGCGCGGCGCTCTCCGGGGC CAGGCTCGGCGCCCGCCCGCGCCCCCCACTGCCGCAGCTGCTCCCGT CGCCGCTCCCGGGCAGCCGCCGCCGCCGCCCCGGGCCAGCCGCCGG GCCATCCTCTCCGGACATCGCACCGCCCGCCCGCCCAGCGAGCGAGC GAGCGCCGAGCCCAACCGCCGCCACCACCCGCCCGCCCGCCCGCCC CGGGGGCCGCCGGGAACTGCCGCTGGCCCCCCACCGCCCCAAGGATC |

TABLE 1-continued

Exemplary DNA sequences useful for incorporation into spacers

| SEQ ID NO. | Description | Sequence |
|---|---|---|
| | | TCCCGGTCCCCGCCCGGCGTGCTGACGTCACGGCGCTGCCCCAGGGT
GTGCTGGGCAGGTCGCGGGGAGCGCTGGGAAATGGAGTCCATTAGCA
GAAGTGGCCCTTGGCCACTTCCAGGAGTCGCTGTGCCCCGATGCACA
CTGGGAAGTCCGCAGCTCCGAGGCGCCCAGTGGAAATCGCCAGATGA
GGGCCTCCTCCGGGGAATGCTGGGAAATGGAGTCTACAGGCCGGAGG
GGTGCCCCACGGCATACTAGGAAGTGTGTAGCACCGGGTAAAGGGGA
TGAATAGCAGACTGCCCCGGGGCAGTTAGGAATTCGACTGGACAGCC
GCGTGGGAGGGAGTGCGGGGAGAGGCAGAGTTGTTTTGTTATTGTTG
TTTTATTTTGTTTTCTTTGTTTTGAGACGGAGTCTCGCTCTGTCGCC
ACGCTGGAGTTCAGTGGCGCGATATCGGCTCGCTGCAACCTCCGCTT
CCCAGGTTCAAGCAATTCTGGCTCAGTCCCCAGAGTAGCTGGGATAA
CAGGCGCGCGCCACCCCGCCCTGCTAATTTTTATATTTTTAGTAGAG
ACGGGATTTCACCATGTTGGCCATGATGGTCTTGATCTCTTGACCTC
ATGATCCGCCCGCCTCGGCCTGTAATCCTGCTGGGATGACGAGCGTA
AGCCACCATGCCCAGCTGGGTTTTATTTATTTTGGTTTTTTTCCTGA
CCCCTTAACTAGAAATAAGCTCCACGAGAGCGGGATCTTTTGTCTTC
TGTGCACTACTTGTCCTCGGTTCTTAGAACAGAACCTGAGAGAACCT
GATCGCAAATATTTTTGGAATGAATGAATGAATGGGTTCACCAGGGC
ACCATGGGAAACTGAGTCCGCAACCTAGAAGCCATGAAAGACAGTCC
ACTTCCAAGCTTCCCTGGGTGACCTCGCAGGGCATGCTGGGAAATGA
AATTTGCGGTGAAAAGGTCAGGACCACGATCCTAGGGCACGCTGGGA
AATGTAGCCCACAGGGCCACACCCCTAAAAGCACAGTGGGGTGCAAG
GCAGGGCCCCAAGGCATTTAGGGCTCGGGCAAGAGAAATCCACACT
CCACTCCCTAATGGTAATCCCTGAGCCACACCGAGTAAAGGAACCCA
AGACACAGTGTCCACAGGGACAGGGCTCTCAGAGCTTTCACTGGCCC
GCGCTTCTCCTGCGCCCACCCGGACCTCCTGGGAACCGCCCAGGCCC
TCGCGCGCTCTCAAGGCATGCTGGGATTGGTGGTCCCGGGCAAGGAG
TTCCAGCAGGTGGGGGGCGAATCACCTTTCAGCGGGCCCAAGCGATG
AGCACACCTTGATCTTCACCTTACGGATCCCGCGCCCAACTCAAGAT
TGGGAAGGTGGCTGGCACTTTGTGACAGGAAGAGTCCCATAAAAATC
ATACAGAAAAGGGCCAAATCGGGACAGAGACTACAGACTGTTTCCC
AAGCGCTGTGGGAGTTTCCCACCCACTCTGAAGTCCTTGGGTTTGCG
CGGAGACGTAAACTGCGCATCCCACGAGGCCTGTTTCTTTCCCTCTC
TCTTTCTCTTTTGTTGTTGTTGTTGCTGCTGCTGTTACGAAAATTTT
TGTGGTTTTATTGTATCATGAGGCATTGAAACATCCGGCGACTCAAT
GTCTAGGCGGTGAGGCAGCCGCTTTCTCCTTCACTTTCTTTGGGTTA
AGTAGAGCAACTTGTCAGTAGTTTTGTTTTTTTTGTTGTTGTTGTT
GTTTTTGAGACGGAGGCTTGCTCTGTCGCCCAGGCTGGAGTGCAGTG
GCGCGATGTCGGCTCACTGCAAGCTCTGCCTCCCGGGTTCAAGCGAT
TCTCCTGCCTCAGCCTCCTGAGTAGCTGGGACTACAGGCGTGCTCCA
CCACGCCCGGCTAATTTTTGTTTTTTAGTAGAGACGGGGTTTCACCA
TGTTGGCCAGGCTGGTCTCGAATTCCTGACCTCGTGATCCGACTGCC
TCGGCCTCCCAAAATGCTGGGATTACAGGCGTGAGCCGCCGCGACCG
GCCAGATTTTTTTTTTTTAAAGGACAACCTTTTGCATTACTTAAG
TCTTTCCAAGGCATGCGCTGGTACAACACAAACTTTTCCCATTACAT
GCAGCTAGTCTAGTGTCCAGACGTCATGCACAACACCTCCGTGGCAT
CAGCGCACTGCGCCCACTCCCACTGCGACCCTGCTCATTTGTGCATC
ATATCTGGAGGAGTGGCAATAGTTCTGGAAAGAGGAGGGAAGAGGAG
GCAGCGTGAGGGCCCGGTGGAGAGGAGGTCAGCTGAAGTTGTGCAGA
GCAAGCCTGCATATCATTGGTGCAAACCCAAGCATCATTGCATCGCT
GATGTTTTGTTTTGTTTGGTTTTGTTTTGTTTTTGAGACGGAGTCTC
ACTGTGTCGCCCAGGCTGGAGTGCAGTGATGTGATCTCGGCTCACTG
CAACCTCCGCCTCCCAGGTTCAAGTGATTCTCCTACCTCAGCCTCCC
AAGTAGCTGGGATTACAGGCGTGCTCCACGCCTGGCTAATTTTTGTA
TTTTTAGTAGAGACAAGGTTTCACCATGTTGGCCAGGCTGGTCTCGA
TCTCCTGACCTCAAGTGATCCACCCGCCTCAGCTTCCCAAAGTGCTG
GGATTACAGGCATGAGCCACCACACCCAGCTGATGTTCTTTAGTAGG
AATATCTGGTGGAACCCCAAGATGGGGTCTTCATCCGCCACGAAGCC
TGTTTCTATAGAAAGGGATAGTTCTGGTGGCTCTTAGGTGTGGTCCC
TGAACCCCACACTTTCCACATACTTACACACCAACCTCCTTCCCCCA
GGAAAACAAGAAGTCGGTCTTCAGGGTGTTACCGTGTAGCTCTGGTT
CTGTATGTATTCTGTGCCTTTATGTATAATTGTGTGTATTTGCAAT |
| 7 | Portion of human ubiquitin C locus: Reverse complement of SEQ ID NO: 1 | CATGGGACAGTAACACAGTAATCATGAAGAATTATAAAAATAAGTGC
TGGCCGGGAGCAGTGGCTCAAGCCTATAATCCCAGCACTTTGGGAGG
CCGAGGCGGGCAGATCACAAGGTCAGGAGATCAAGACCATCCTGGCT
AACACAGTGAAACCCTGTCTCTACTAAAAATACAAAAAAAATTAGAC
GGGCTTTGTAGAGGGCGCCTGGAGTCCCAGCTACTCGGGAGACTGAG
GCAGGAGAATGGTGTGAACTCATGAGGTGGAGCTTGCAGTGAGCCGA
GATCACGCCACTGCACTCCAGCATGGACAACAGAGCGAGACTCCCTC
TCAAAAAAAATAAATAAATAAGTGCTAAGGCTGATTATTTTATTAGC
CCTAAGAATCCAATTAAAAATAGAAATCTTGTATTTATGCTATTCTTT
CAAAATCTTTATGTAAAGCAAGCTTTTAATAGGATGTTATAAAAATA
GATTTTGCTCCTTGTGTTCAAGTTTCTCCTCTTGAAATTGCACATTT
TACATTTTTTAAAAAATTAAAATTAAAAAACAAAATAGTATGATAGT
GTTAATTTGGCAGTTCCAACTTTAGTAACCTATCTTACAGAAATATG |

TABLE 1-continued

Exempary DNA sequences useful for incorporation into spacers

| SEQ ID NO. | Description | Sequence |
|---|---|---|
| | | AATAGACAAAATAAAGATGTGTGAGGATGTACTTTGCAGCAGCATTA<br>TAATAGCAAAAACCTGGAAACAAATATTGATGGACAGGTTAAGTAAA<br>TCATAGGACATTCATACAATGGAATACTAGCAAAAATATTAAAAAGA<br>ATGAGGTAGATATTGATATGCTAGTATGGAAAGATGTCCATAATTAT<br>CTAGTTCCCCACCTCAAAAAAAAAAAAAAAACCTGAGAATCATTATA<br>CTGAGAATGGTCCAATTTGTGTCTGTATGTACATAATATGTACATAA<br>CAAATATAGTATATTTTTACACAGGGGAAAAGTCCAAAAGAATATCA<br>ACCTGTAAAAAGTAGTTATCCCAGCTGGGTGAGGTTGCTCATGCCTG<br>TAATCCCAGCACTTTGGGAGGCAGAGGCAGGCGGATCACAAGGTCAG<br>GAGATCGAGACCATCCTGGCTAACACAGTGAAACCCTGTCTCTACTA<br>AAAATACAAAAAATTAGCCAGGTATGGCGAGGTGAGCCTGTAGTCCT<br>AGTTGTTGGGGAGGCTGAGGCAGGAGAATAGCGTGAACCAGGGAGGA<br>GGAGCTTGCAGTGAGCCGAGATGGTGCCACTGCACTCCAGCCTGGGC<br>TACACAGCGAGACTCCATCTCAAAAAGAAAAAGTAGTTAGTTATCCC<br>TGGAAAGTAAAATTGAGTAGGAACTTAAATGGGTTACTATCACCTTT<br>GACTTTATAAAGGTGCACACAAACACACAAAATGTGTATGTATTTAA<br>TTACAAACAGTAAGAGACCTGGCATGGTGCCTCACACCTGTAATCTC<br>AGCACTTTGGGAGGCAGAGGCAGGAGAATCACTTGAGGCCAGGAGTT<br>TGAGACCAACCTATGCAACAAGCGAAATCCAACCCCCCCTTTTTTTT<br>TTCCTGATACGGAGTCTTGCTCTTGTTGCCCAGGCTGGAATGCAGTT<br>ACACAATCTCGGCTCACTGCAACCTCCACATCCCTGGTTCCAGGGAT<br>TCTCCTGCCTCAGCCTTCCGAGTAGCTGGGATTACAGGCGCCTGCCA<br>ACACACCCAGCTATTTTTTTGTATATTTTGTAGAGATGGGATTTGCC<br>ATCCCTCCAACTCCTGACCTCAGGTGATCCGCCCACCTGGGCCTCCC<br>AAAGTGCTGGGATTACAGGCGTGAGCCACCTCACCCGGCCTGAAATC<br>CCCTATTTTTAAAAAAGGTAAATAAACGTATTTTTTTTCTCTGGGAG<br>TGACCATACGTGGAAATTTCACTTTCTACATCACTAATTTTATGAAT<br>GTGCTTATGTTGCTCTATACTGCTTTTCAAAACTTTTCTAGTACCTA<br>TGCTTGTAATTCGGAATTTCTCACTGAACTTGATAGAAGCACTTTAG<br>TTCAAGGGGCCAAGTGTTCTTCAGTGAGTTTTCAAGTGAGCATCCTC<br>ACCTCTACAACATTCACACAGCTTTATTAAATAGACTAATGTTCGCT<br>CACACCAAGATCCTGCCGGCTCTGCACAACGCTGTTAACACCAATGT<br>GACCCAGTTCCATCCCACATCTTCAACAGCTTTAGCAGCCATGGCCT<br>TTCTTGTACTTGACTTGATGCAGCTTTGAAGTTTTCAAAAAGCACCT<br>TACACAGATTTATCAATGTTACAATGCCTGACACCAAGTGTACATCT<br>TTAACACTATTCAAGGTATTTTTTCCTTACACTAAGGTCATCCAGAT<br>TTTAATGGTAACTAAAATTACACAGAAAGTTGCATACTAACTGGAAG<br>TGATCGCCTGTCTAGTAGTGGTTGAGTTTGTTGGGTTCTTGTAACGT<br>TTCCTGATTCACATGCTCACTTGCATGGGAGGGTCATGGAAATTATA<br>CATTGGATGCACTCATAATGAAAACTCACAATGGATTTCCTTAAGAT<br>TTATGAATTTCTCAAATTTTAGTCCAGTAACCCTAACCCTAAAGCTA<br>AAACTGGTTTAAGCCACCCTCAGTTGCTTTACAATTGCTAGGGACAT<br>GAAACTATCCCACAGCAGCTGTTCATGAATCCCCTAAAACTTTAAGC<br>GAGAGAAGAGGGAGTGATTCTCCTTCGGAAAAACATTCCAAGGCCTT<br>TAATGGGCCTCTGGATGACTGCCTGGTGTCCACCCTTGTACTAAACC<br>AGTTTCCCTGCAACTTCCACCTTTGGTTCTAGTCAACATTAACACCT<br>TACCAGGACCATTCGATTGGGCAAATGCTACTATACACTTGGACAAA<br>TCCAGAGGTCAATTGTTTCCCCCACTGGTTAGGTTATGTGCCAATCC<br>TCCACCTGTAGTCACATAAAATGTGACATTTTACCAGCAAGAATTGT<br>TTCAAGAACGCAATTGTTTCAACGAATAGCTCACTCTCTAACCACTA<br>ATTCTTTTTCCACACCTTGTTAGCTATGCCTTTTTTTAC |
| 8 | Portion of human<br>ubiquitin C locus:<br>Reverse<br>complement of<br>SEQ ID NO: 2 | TCACTCCCAGGAGTTCGGCAGCTTTTGCACATTTTAAGATCAACTGA<br>GAGTTTATAAATATGCCCCGTTTTTCTATGACCATCGCTATGGGAAG<br>AGATGAATGTGTTCTAACCTGTTTCCCATCAAAACTTGTGTTCTAAC<br>CCCAAAAGGAAAAGCAGCAATAAAAACAACCAAAACATTTTTTAAAA<br>ATAGGTTCTATAGTTTCAAAAACAATAAAAAGAATAAGAGCCAAGCC<br>TGGAGGTGCGCGCCTGTAGTCCCAGCTACTTAGGAGGCTGAGGCAAG<br>AGGATGGCTTCAGCTGGGGAGGTTGAGGCTGGAGTGCAGTGGCGCAG<br>TCTCGGCTCACTGCAACCTCCGCCTCCTGAGTTCAAGCGTTTCTCCT<br>GCCTCAACCTCCCGAGTAGCTGGGATTACAGGTGCATACCACCACGC<br>CTGGCTAATTTTTGTTTTGTTTTGTTTCGTTTGTTTGTTTTTTTGAG<br>AGGGAGTCTCTCTCTGTCTCCCAGGCTGGAGTGCAGTGGTGCAATCT<br>CGGCTCACTGCAAGCTCAGCCTTCCAGGTTCACGCCATTCTCCTGCC<br>TCAGCCTCCCAGGTAGCTGGGACTACAGGCTCCTGCCACCACGCCCA<br>GCTAATTTTTTTTTTTTTTTTTGTATTTTTAGTAGAGAGGGGGT<br>TTCACCGTGTTAGCCAGGATGGTCTCAATCTCCTGAGCTCATGATCC<br>GCCTGCCTTGGCCTCCAAAGTGCTGGGATTACAGGCGTGAGCCACC<br>ACTCCCGGCCTCCTCCAGCCCCATCTCTTCACATGCTTTTCCCACCT<br>CAGTTATGCTGGTCTCCTTTCTGTTCCTCAAATATGCCCAAGTCTTC<br>CAGCCCCAGGGCCCCGTGCTATTTCCTGCCTCTCCACCTTCTGCAA<br>AGCTAAGGCCCATCTTCCAGGTCTCACATAAATACTGTCTTTCCCGA<br>AAGCCTCTTCCAACCATCCACAAGCAGGATCCCAAACTCCTCCCATT<br>CAACCTGACAGCCTCACATAGCTCCTGTCACCATGTGTAATTTTGC<br>TTACTAGCAGATCAAAGAACAGAAGCAAGCCGTTTGATTGTTTCTTT<br>TTGTTTTGTTTTGTTTTTAGACAGAGTCTCACGAGCCTCCTTACAAA |

TABLE 1-continued

Exemplary DNA sequences useful for incorporation into spacers

| SEQ ID NO. | Description | Sequence |
|---|---|---|
| | | ATAGAAAAGTCAATGGGATTTCAGGGAAAATGGATAATCTTCGTTGG<br>GGGCAGTCAAGGAAGGCTTTGTGGAACCTTTGAATTAGGTCTTGACA<br>TTATATCTTGACAGTACTTTGAATAAATACAAATAATGTTATTTTTT<br>TGTTAAGACTCATGCAACCGCATCTATGTAAATGAATCCGTACATAG<br>TATTCATTCGAGTGTGAAATCAGACTTTGGGATGCTTTAAAATTTAA<br>CAGTCAGGAACACTTACTCTATTTTATGGACTTAAATTTGTTGAGGT<br>GGCAGGGAACAACTTGAGTGAAGGGTGGGACATGGCAGTGTGTATGT<br>GGGGGAAAAAGGTGGCCAGCAGATAAGGGAAGCAGGGGACAGAGTAT<br>TTTGAGGGATTAGACCTGACCAGCTATAACAGGAAATAGAGGCTGTA<br>GATTGAAGGATAGCTACAATGGATGTTATGGAGAAATTCCAACTGGG<br>GTGGAAACATGTAGCTGCAAAATTGGAAGAGCAGCTTATTCTAGGCA<br>GAAAAGAAGAAAGTAAAAGGCATCTGAGGGGACACTAAATTAATGCT<br>TACTGATAAGTAAACAAGCCTCTGGAAGTAGAAAGGTAAAAGCATAA<br>ATTGCTTGGTCAACCACAACCGCTTGGGAGTGCTGGAGGCTTCATGA<br>CTAAACCAAAGTCTGTCCCTGAAGCTCCCTCTTCCGGCAGAAATAAA<br>TACTGCACACTAAGCTGGCTGACTCCTTTCATTAAAAGGTGCTTGCC<br>AATCTCTAAACAGTTTACCTGTATGGGAGTCATAATTGTAATATCTT<br>GGTGAGGATTTTGTTGTGCTTTCAGGCAAACCATAAAAGGAACACTA<br>ATTTAAATAAATACAAACAATGTTATTTTATTCTTAAGATTCAGGCA<br>ACCACATCTATGTAAGTGAATCCTTACATGGTATTCATTCAAGTGTG<br>AAACCAAACTTTAGGATGCTTTAAAATTTAACAATCAGGAACAAGAC<br>TCTGTTAAAAAAAAAAAAAAAGAAATGTTAGAACTCTGTCAAACTAT<br>AAAAATATAAAGTGAAATAGCACAGTGCAGACAGACTGTACAGACCA<br>GTGTGCTACCTTTCATGTAAAGGGGAATTACATATATTATATATATG<br>ATTTTTTTATTATTTGTGTATATACAGTACTCACTGTATATGCATAA<br>AGTCTGCAAGTACATGCTGGGGGGAAGGGGTGGATGGGAGACAAGGA<br>TGGAAGATTTTTTTGTTGTTTTTTTTTGGAGACCGAGTCTCGCTCTG<br>TCACTCAGGCTGGAGGGCAGTGGCACCATCTCAGCTCACTGCAACCT<br>CCCACCTCCCAGGTTCAAGAGATTCTCCTGCCTCAGCCTCCCGAGTAG<br>CTGGGACTACAGGCATCCATCACCACGCTCAGCTAATTTTTGTATTT<br>TATTAGAGATGAGGTTTTGCTATATATATATATATATATATATATGA<br>ATATATGAATATATATATGAATATATGAATATATATATATATATG<br>AATATATGAATATATATATATTGGCCAGGCTGGTCTCGAACTCCTGC<br>CCTCAGGTGATCTGCCCACCTCAGCCTCCCAAAGTGCTGGGATTACA<br>GGTGTGAGTGGCCTGGAAGATTTTTTATTATATACTGTTTAAAAGTT<br>TTTAAGTAGTTGAAACACATGAAGACATCACCTCAAAAAGTTATATT<br>AACAATTCAAAAATATGCACATTAAGGATTAATTTTTTTGAAAAATT<br>TAAAAATTGAGAAATAT |
| 9 | Portion of human ubiquitin C locus: Reverse complement of SEQ ID NO: 3 | CATGGGACAGTAACACAGTAATCATGAAGAATTATAAAAATAAGTGC<br>TGGCCGGGAGCAGTGGCTCAAGCCTATAATCCCAGCACTTTGGGAGG<br>CCGAGGCGGGCAGATCACAAGGTCAGGAGATCAAGACCATCCTGGCT<br>AACACAGTGAAACCCTGTCTCTACTAAAAATACAAAAAAAATTAGAC<br>GGGCTTTGTAGAGGGCGCCTGGAGTCCCAGCTACTCGGGAGACTGAG<br>GCAGGAGAATGGTGTGAACTCATGAGGTGGAGCTTGCAGTGAGCCGA<br>GATCACGCCACTGCACTCCAGCATGGACAACAGAGCGAGACTCCCTC<br>TCAAAAAAAATAAATAAATAAGTGCTAAGGCTGATTATTTTATTAGC<br>CCTAAGAATCCAATTAAAATAGAAATCTTGTATTTATGCTATTCTTT<br>CAAAATCTTTATGTAAAGCAAGCTTTTAATAGGATGTTATAAAAATA<br>GATTTTGCTCCTTGTGTTCAAGTTTCTCCTCTTGAAATTGCACATTT<br>TACATTTTTTAAAAAATTAAAATTAAAAAACAAAATAGTATGATAGT<br>GTTAATTTGGCAGTTCCAACTTTAGTAACCTATCTTACAGAAATATG<br>AATAGACAAAATAAAGATGTGTGAGGATGTACTTTGCAGCAGCATTA<br>TAATAGCAAAAACCTGGAAACAAATATTGATGGACAGGTTAAGTAAA<br>TCATAGGACATTCATACAATGGAATACTAGCAAAAATATTAAAAAGA<br>ATGAGGTAGATATTGATATGCTAGTATGGAAAGATGTCCATAATTAT<br>CTAGTTCCCCACCTCAAAAAAAAAAAAAAAACCTGAGAATCATTATA<br>CTGAGAATGGTCCAATTTGTGTCTGTATGTACATAATATGTACATAA<br>CAAATATAGTATATTTTTACACAGGGGAAAAGTCCAAAAGAATATCA<br>ACCTGTAAAAGTAGTTATCCCAGCTGGGTGAGGTTGCTCATGCCTG<br>TAATCCCAGCACTTTGGGAGGCAGAGGCAGGCGGATCACAAGGTCAG<br>GAGATCGAGACCATCCTGGCTAACACAGTGAAACCCTGTCTCTACTA<br>AAAATACAAAAAATTAGCCAGGTATGGCGAGGTGAGCCTGTAGTCCT<br>AGTTGTTGGGGAGGCTGAGGCAGGAGAATAGCGTGAACCAGGGAGGA<br>GGAGCTTGCAGTGAGCCGAGATGGTGCCACTGCACTCCAGCCTGGGC<br>TACACAGCGAGACTCCATCTCAAAAAGAAAAAGTAGTTAGTTATCCC<br>TGGAAAGTAAAATTGAGTAGGAACTTAAATGGGTTACTATCACCTTT<br>GACTTTATAAAGGTGCACACAAACACACAAAATGTGTATGTATTTAA<br>TTACAAACAGTAAGAGACCTGGCATGGTGCCTCACACCTGTAATCTC<br>AGCACTTTGGGAGGCAGAGGCAGGAGAATCACTTGAGGCCAGGAGTT<br>TGAGACCAACCTATGCAACAAGCGAAATCCAACCCCCCCTTTTC |
| 10 | Portion of human ubiquitin C locus: Reverse | GTTTTATGGACTTAAATTTGTTGAGGTGGCAGGGAACAACTTGAGTG<br>AAGGGTGGGACATGGCAGTGTGTATGTGGGGGAAAAAGGTGGCCAGC<br>AGATAAGGGAAGCAGGGGACAGAGTATTTTGAGGGATTAGACCTGAC |

TABLE 1-continued

Exemplary DNA sequences useful for incorporation into spacers

| SEQ ID NO. | Description | Sequence |
| --- | --- | --- |
|  | complement of SEQ ID NO: 4 | CAGCTATAACAGGAAATAGAGGCTGTAGATTGAAGGATAGCTACAAT<br>GGATGTTATGGAGAAATTCCAACTGGGGTGGAAACATGTAGCTGCAA<br>AATTGGAAGAGCAGCTTATTCTAGGCAGAAAAGAAGAAAGTAAAAGG<br>CATCTGAGGGGACACTAAATTAATGCTTACTGATAAGTAAACAAGCC<br>TCTGGAAGTAGAAAGGTAAAAGCATAAATTGCTTGGTCAACCACAAC<br>CGCTTGGGAGTGCTGGAGGCTTCATGACTAAACCAAAGTCTGTCCCT<br>GAAGCTCCCTCTTCCGGCAGAAATAAATACTGCACACTAAGCTGGCT<br>GACTCCTTTCATTAAAAGGTGCTTGCCAATCTCTAAACAGTTTACCT<br>GTATGGGAGTCATAATTGTAATATCTTGGTGAGGATTTTGTTGTGCT<br>TTCAGGCAAACCATAAAAGGAACACTAATTTAAATAAATACAAACAA<br>TGTTATTTTATTCTTAAGATTCAGGCAACCACATCTATGTAAGTGAA<br>TCCTTACATGGTATTCATTCAAGTGTGAAACCAAACTTTAGGATGCT<br>TTAAAATTTAACAATCAGGAACAAGACTCTGTTAAAAAAAAAAAAA<br>AGAAATGTTAGAACTCTGTCAAACTATAAAAATATAAAGTGAAATAG<br>CACAGTGCAGACAGACTGTACAGACCAGTGTGCTACCTTTCATGTAA<br>AGGGGAATTACATATATTTATATATATGATTTTTTTATTATTTGTGTA<br>TATACAGTACTCACTGTATATGCATAAAGTCTGCAAGTACATGCTGG<br>GGGGAAGGGGTGGATGGGAGACAAGGATGGAAGATTTTTTTGTTGTT<br>TTTTTTTGGAGACCGAGTCTCGCTCTGTCACTCAGGCTGGAGGGCAG<br>TGGCACCATCTCAGCTCACTGCAACCTCCACCTCCCAGGTTCAAGAG<br>ATTCTCCTGCCTCAGCCTCCCGAGTAGCTGGGACTACAGGCATCCAT<br>CACCACGCTCAGCTAATTTTTGTATTTTATTAGAGATGAGGTTTTGC<br>TATATATATATATATATATATATATATGAATATATGAATATATATATAT<br>GAATATATGAATATATATATATATATGAATATATGAATATATATATA<br>TTGGCCAGGCTGGTCTCGAACTCCTGCCCTCAGGTGATCTGCCCACC<br>TCAGCCTCCCAAAGTGCTGGGATTACAGGTGTGAGTGGCCTGGAAGA<br>TTTTTTATTATATACTGTTTAAAAGTTTTTAAGTAGTTGAAACACAT<br>GAAGACATCACCTCAAAAAGTTATATTAACAATTCAAAAATATGCAC<br>ATTAAGGATTAATTTTTTTGAAAAATTTAAAAATTGAGAAATAT |
| 11 | Rep-binding site of human AAVS1 locus: Reverse complement of SEQ ID NO: 5 | GCGCTCGCTCGCTC |
| 12 | Human AAVS1 locus: Reverse complement of SEQ ID NO: 6 | ATTGCAAATACACACAATTATACATAAAGGCACAGAATACATACAGA<br>ACCAGAGCTACACGGTAACACCCTGAAGACCGACTTCTTGTTTTCCT<br>GGGGGAAGGAGGTTGGTGTGTAAGTATGTGGAAAGTGTGGGGTTCAG<br>GGACCACACCTAAGAGCCACCAGAACTATCCCTTTCTATAGAAACAG<br>GCTTCGTGGCGGATGAAGACCCCATCTTGGGGTTCCACCAGATATTC<br>CTACTAAAGAACATCAGCTGGGTGTGGTGGCTCATGCCTGTAATCCC<br>AGCACTTTGGGAAGCTGAGGCGGGTGGATCACTTGAGGTCAGGAGAT<br>CGAGACCAGCCTGGCCAACATGGTGAAACCTTGTCTCTACTAAAAAT<br>ACAAAAATTAGCCAGGCGTGGAGCACGCCTGTAATCCCAGCTACTTG<br>GGAGGCTGAGGTAGGAGAATCACTTGAACCTGGGAGGCGGAGGTTGC<br>AGTGAGCCGAGATCACATCACTGCACTCCAGCCTGGGCGACACAGTG<br>AGACTCCGTCTCAAAAACAAAACAAAACCAAACAAAACAAAACATCA<br>GCGATGCAATGATGCTTGGGTTTGCACCAATGATATGCAGGCTTGCT<br>CTGCACAACTTCAGCTGACCTCCTCTCCACCGGGCCCTCACGCTGCC<br>TCCTCTTCCCTCCTCTTTCCAGAACTATTGCCACTCCTCCAGATATG<br>ATGCACAAATGAGCAGGGTCGCAGTGGGAGTGGGCGCAGTGCGCTGA<br>TGCCACGGAGGTGTTGTGCATGACGTCTGGACACTAGACTAGCTGCA<br>TGTAATGGGAAAAGTTTGTGTTGTACCAGCGCATGCCTTGGAAAGAC<br>TTAAGTAATGCAAAAGGTTGTCCTTTAAAAAAAAAAAAAATCTGGCC<br>GGTCGCGGCGGCTCACGCCTGTAATCCCAGCATTTTGGGAGGCCGAG<br>GCAGTCGGATCACGAGGTCAGGAATTCGAGACCAGCCTGGCCAACAT<br>GGTGAAACCCCGTCTCTACTAAAAACAAAAATTAGCCGGGCGTGGT<br>GGAGCACGCCTGTAGTCCCAGCTACTCAGGAGGCTGAGGCAGGAGAA<br>TCGCTTGAACCCGGGAGGCAGAGCTTGCAGTGAGCCGACATCGCGCC<br>ACTGCACTCCAGCCTGGGCGACAGAGCAAGCCTCCGTCTCAAAAACA<br>ACAACAACAAAAAAAACAAAACTACTGACAAGTTGCTCTACTT<br>AACCCAAAGAAAGTGAAGGAGAAAGCGGCTGCCTCACCGCCTAGACA<br>TTGAGTCGCCGGATGTTTCAATGCCTCATGATACAATAAAACCACAA<br>AAATTTTCGTAACAGCAGCAGCAACAACAACAAAAGAGAAAGAG<br>AGAGGGAAAGAAACAGGCCTCGTGGGATGCGCAGTTTACGTCTCCGC<br>GCAAACCCAAGGACTTCAGAGTGGGTGGGAAACTCCCACAGCGCTTG<br>GGAAACAGTCTGTAGTCTCTGTCCCGATTTTGGCCCTTTTCTGTATG<br>ATTTTTATGGGACTCTTCCTGTCACAAAGTGCCAGCCACCTTCCCAA<br>TCTTGAGTTGGGCGCGGGATCCGTAAGGTGAAGATCAAGGTGTGCTC<br>ATCGCTTGGGCCCGCTGAAAGGTGATTCGCCCCCCACCTGCTGGAAC<br>TCCTTGCCCGGGACCACCAATCCCAGCATGCCTTGAGAGCGCGCGAG<br>GGCCTGGGCGGTTCCCAGGAGGTCCGGGTGGGCGCAGGAGAAGCGCG<br>GGCCAGTGAAAGCTCTGAGAGCCCTGTCCCTGTGGACACTGTGTCTT<br>GGGTTCCTTTACTCGGTGTGGCTCAGGGATTACCATTAGGGAGTGGA<br>GTGTGGATTTCTCTTGCCCCGAGCCCTAAATGCCTTGGGGCCCTGCC |

TABLE 1-continued

Exempary DNA sequences useful for incorporation into spacers

| SEQ ID NO. | Description | Sequence |
|---|---|---|
| | | TTGCACCCCACTGTGCTTTTAGGGGTGTGGCCCTGTGGGCTACATTT |
| | | CCCAGCGTGCCCTAGGATCGTGGTCCTGACCTTTTCACCGCAAATTT |
| | | CATTTCCCAGCATGCCCTGCGAGGTCACCCAGGGAAGCTTGGAAGTG |
| | | GACTGTCTTTCATGGCTTCTAGGTTGCGGACTCAGTTTCCCATGGTG |
| | | CCCTGGTGAACCCATTCATTCATTCATTCCAAAAATATTTGCGATCA |
| | | GGTTCTCTCAGGTTCTGTTCTAAGAACCGAGGACAAGTAGTGCACAG |
| | | AAGACAAAAGATCCCGCTCTCGTGGAGCTTATTTCTAGTTAAGGGGT |
| | | CAGGAAAAAAACCAAAATAAATAAAACCCAGCTGGGCATGGTGGCTT |
| | | ACGCTCGTCATCCCAGCAGGATTACAGGCCGAGGCGGGCGGATCATG |
| | | AGGTCAAGAGATCAAGACCATCATGGCCAACATGGTGAAATCCCGTC |
| | | TCTACTAAAAATATAAAATTAGCAGGGCGGGGTGGCGCGCGCCTGT |
| | | TATCCCAGCTACTCTGGGGACTGAGCCAGAATTGCTTGAACCTGGGA |
| | | AGCGGAGGTTGCAGCGAGCCGATATCGCGCCACTGAACTCCAGCGTG |
| | | GCGACAGAGCGAGACTCCGTCTCAAAACAAAGAAAACAAAATAAAAC |
| | | AACAATAACAAAACAACTCTGCCTCTCCCCGCACTCCCTCCCACGCG |
| | | GCTGTCCAGTCGAATTCCTAACTGCCCCGGGGCAGTCTGCTATTCAT |
| | | CCCCTTTACCCGGTGCTACACACTTCCTAGTATGCCGTGGGGCACCC |
| | | CTCCGGCCTGTAGACTCCATTTCCCAGCATTCCCCGGAGGAGGCCCT |
| | | CATCTGGCGATTTCCACTGGGCGCCTCGGAGCTGCGGACTTCCCAGT |
| | | GTGCATCGGGGCACAGCGACTCCTGGAAGTGGCCAAGGGCCACTTCT |
| | | GCTAATGGACTCCATTTCCCAGCGCTCCCCGCGACCTGCCCAGCACA |
| | | CCCTGGGGCAGCGCCGTGACGTCAGCACGCCGGGCGGGGACCGGGAG |
| | | ATCCTTGGGCGGTGGGGGGCCAGCGGCAGTTCCCGGCGGCCCCCGG |
| | | GGCGGGCGGGCGGGCGGGTGGTGGCGGCGGTTGGGGCTCGGCGCTCG |
| | | CTCGCTCGCTGGGCGGGCGGGCGGTGCGATGTCCGGAGAGGATGGCC |
| | | CGGCGGCTGGCCCGGGGGCGGCGGCGGCGGCTGCCCGGGAGCGGCGA |
| | | CGGGAGCAGCTGCGGCAGTGGGGGGCGCGGGCGGGCGCCGAGCCTGG |
| | | CCCCGGAGAGCGCCGCGCCCGCACCGTCCGCTTCGAGCGCGCCGCCG |
| | | AGTTCCTGGCGGCCTGTGCGGGCGGCGACCTGGACGAGGCGCGTCTG |
| | | ATGCTGCGCGCCGCCGACCCTGGCCCCGGCGCCGAGCTCGACCCCGC |
| | | CGCGCCGCCGCCCGCCGCGCCGTGCTGGACTCCACCAACGCCGACG |
| | | GTATCAGCGCCCTGCACCAGGTCAGCGCCCCCGCCCGGCGTCTCCC |
| | | GGGGCCAGGTCCACCCTCTGCTGCGCCACCTGGGGCATCCTCCTTCC |
| | | CCGTTGCCAGTCTCGATCCGCCCCGTCGTTCCTGGCCCTGGGCTTTG |
| | | CCACCCTATGCTGACACCCCGTCCCAGTCCCCCTTACCATTCCCCTT |
| | | CGACCACCCCACTTCCGAATTGGAGCCGCTTCAACTGGCCCTGGGCT |
| | | TAGCCACTCTGTGCTGACCACTCTGCCCCAGGCCTCCTTACCATTCC |
| | | CCTTCGACCTACTCTCTTCCGCATTGGAGTCGCTTTAACTGGCCCTG |
| | | GCTTTGGCAGCCTGTGCTGACCCATGCAGTCCTCCTTACCATCCCTC |
| | | CCTCGACTTCCCCTCTTCCGATGTTGAGCCCCTCCAGCCGGTCCTGG |
| | | ACTTTGTCTCCTTCCCTGCCCTGCCCTCTCCTGAACCTGAGCCAGCT |
| | | CCCATAGCTCAGTCTGGTCTATCTGCCTGGCCCTGGCCATTGTCACT |
| | | TTGCGCTGCCCTCCTCTCGCCCCCGAGTGCCCTTGCTGTGCCGCCGG |
| | | AACTCTGCCCTCTAACGCTGCCGTCTCTCTCCTGAGTCCGGACCACT |
| | | TTGAGCTCTACTGGCTTCTGCGCCGCCTCTGGCCCACTGTTTCCCCT |
| | | TCCCAGGCAGGTCCTGCTTTCTCTGACCTGCATTCTCTCCCCTGGGC |
| | | CTGTGCCGCTTTCTGTCTGCAGCTTGTGGCCTGGGTCACCTCTACGG |
| | | CTGGCCCAGATCCTTCCCTGCCGCCTCCTTCAGGTTCCGTCTTCCTC |
| | | CACTCCCTCTTCCCCTTGCTCTCTGCTGTGTTGCTGCCCAAGGATGC |
| | | TCTTTCCGGAGCACTTCCTTCTCGGCGCTGCACCACGTGATGTCCTC |
| | | TGAGCGGATCCTCCCCGTGTCTGGGTCCTCTCCGGGCATCTCTCCTC |
| | | CCTCACCCAACCCCATGCCGTCTTCACTCGCTGGGTTCCCTTTTCCT |
| | | TCTCCTTCTGGGGCCTGTGCCATCTCTCGTTTCTTAGGATGGCCTTC |
| | | TCCGACGGATGTCTCCCTTGCGTCCCGCCTCCCCTTCTTGTAGGCCT |
| | | GCATCATCACCGTTTTTCTGGACAACCCCAAAGTACCCCGTCTCCCT |
| | | GGCTTTAGCCACCTCTCCATCCTCTTGCTTTCTTTGCCTGGACACCC |
| | | CGTTCTCCTGTGGATTCGGGTCACCTCTCACTCCTTTCATTTGGGCA |
| | | GCTCCCCTACCCCCCCTTACCTCTCTAGTCTGTGCTAGCTCTTCCAGC |
| | | CCCCTGTCATGGCATCTTCCAGGGGTCCGAGAGCTCAGCTAGTCTTC |
| | | TTCCTCCAACCCGGGCCCCTATGTCCACTTCAGGACAGCATGTTTGC |
| | | TGCCTCCAGGGATCCTGTGTCCCCGAGCTGGGACCACCTTATATTCC |
| | | CAGGGCCGGTTAATGTGGCTCTGGTTCTGGGTACTTTTATCTGTCCC |
| | | CTCCACCCCACAGTGGGGCCACTAGGGACAGGATTGGTGACAGAAAA |
| | | GCCCCATCCTTAGGCCTCCTCCTTCCTAGTCTCCTGATATTGGGTCT |
| | | AACCCCCACCTCCTGTTAGGCAGATTCCTTATCTGGTGACACACCCC |
| | | CATTTCCTGGAGCCATCTCTCTCCTTGCCAGAACCTCTAAGGTTTGC |
| | | TTACGATGGAGCCAGAGAGGATCCTGGGAGGGAGAGCTTGGCAGGGG |
| | | GTGGGAGGGAAGGGGGGATGCGTGACCTGCCCGGTTCTCAGTGGCC |
| | | ACCCTGCGCTACCCTCTCCCAGAACCTGAGCTGCTCTGACGCGGCTG |
| | | TCTGGTGCGTTTCACTGATCCTGGTGCTGCAGCTTCCTTACACTTCC |
| | | CAAGAGGAGAAGCAGTTTGGAAAAACAAAATCAGAATAAGTTGGTCC |
| | | TGAGTTCTAACTTTGGCTCTTCACCTTTCTAGTCCCCAATTTATATT |
| | | GTTCCTCCGTGCGTCAGTTTTACCTGTGAGATAAGGCCAGTAGCCAG |
| | | CCCCGTCCTGGCAGGGCTGTGGTGAGGAGGGGGGTGTCCGTGTGGAA |
| | | AACTCCCTTTGTGAGAATGGTGCGTCCTAGGTGTTCACCAGGTCGTG |
| | | GCCGCCTCTACTCCCTTTCTCTTTCTCCATCCTTCTTTCCTTAAAGA |

TABLE 1-continued

Exemplary DNA sequences useful for incorporation into spacers

| SEQ ID NO. | Description | Sequence |
|---|---|---|
| | | GTCCCCAGTGCTATCTGGGACATATTCCTCCGCCCAGAGCAGGGTCC<br>CGCTTCCCTAAGGCCCTGCTCTGGGCTTCTGGGTTTGAGTCCTTGGC<br>AAGCCCAGGAGAGGCGCTCAGGCTTCCCTGTCCCCCTTCCTCGTCCA<br>CCATCTCATGCCCCTGGCTCTCCTGCCCCTTCCCTACAGGGGTTCCT<br>GGCTCTGCTCTTCAGACTGAGCCCCGTTCCCCTGCATCCCCGTTCCC<br>CTGCATCCCCCTTCCCCTGCATCCCCCAGAGGCCCCAGGCCACCTAC<br>TTGGCCTGGACCCCACGAGAGGCCACCCCAGCCCTGTCTACCAGGCT<br>GCCTTTTGGGTGGATTCTCCTCCAACTGTGGGGTGACTGCTTGGCAA<br>ACTCACTCTTCGGGGTATCCCAGGAGGCCTGGAGCATTGGGGTGGGC<br>TGGGGTTCAGAGAGGAGGGATTCCCTTCTCAGGTTACGTGGCCAAGA<br>AGCAGGGGAGCTGGGTTTGGGTCAGGTCTGGGTGTGGGGTGACCAGC<br>TTATGCTGTTTGCCCAGGACAGCCTAGTTTTAGCGCTGAAACCCTC |

Exemplary combinations of nucleic acid sequences that can be incorporated into spacers are described in Table 2, below.

TABLE 2

Exemplary combinations of polynucleotides useful for incorporation into spacers

| No. | First spacer (SS1) | Second spacer (SS2) |
|---|---|---|
| 1 | Polynucleotide that has at least 85% sequence identity to SEQ ID NO: 1 | Polynucleotide that has at least 85% sequence identity to SEQ ID NO: 1 |
| 2 | Polynucleotide that has at least 85% sequence identity to SEQ ID NO: 1 | Polynucleotide that has at least 85% sequence identity to SEQ ID NO: 2 |
| 3 | Polynucleotide that has at least 85% sequence identity to SEQ ID NO: 1 | Polynucleotide that has at least 85% sequence identity to SEQ ID NO: 3 |
| 4 | Polynucleotide that has at least 85% sequence identity to SEQ ID NO: 1 | Polynucleotide that has at least 85% sequence identity to SEQ ID NO: 4 |
| 5 | Polynucleotide that has at least 85% sequence identity to SEQ ID NO: 1 | Polynucleotide that has at least 85% sequence identity to SEQ ID NO: 5 |
| 6 | Polynucleotide that has at least 85% sequence identity to SEQ ID NO: 1 | Polynucleotide that has at least 85% sequence identity to SEQ ID NO: 6 |
| 7 | Polynucleotide that has at least 85% sequence identity to SEQ ID NO: 1 | Polynucleotide that has at least 85% sequence identity to SEQ ID NO: 7 |
| 8 | Polynucleotide that has at least 85% sequence identity to SEQ ID NO: 1 | Polynucleotide that has at least 85% sequence identity to SEQ ID NO: 8 |
| 9 | Polynucleotide that has at least 85% sequence identity to SEQ ID NO: 1 | Polynucleotide that has at least 85% sequence identity to SEQ ID NO: 9 |
| 10 | Polynucleotide that has at least 85% sequence identity to SEQ ID NO: 1 | Polynucleotide that has at least 85% sequence identity to SEQ ID NO: 10 |
| 11 | Polynucleotide that has at least 85% sequence identity to SEQ ID NO: 1 | Polynucleotide that has at least 85% sequence identity to SEQ ID NO: 11 |
| 12 | Polynucleotide that has at least 85% sequence identity to SEQ ID NO: 1 | Polynucleotide that has at least 85% sequence identity to SEQ ID NO: 12 |
| 13 | Polynucleotide that has at least 85% sequence identity to SEQ ID NO: 2 | Polynucleotide that has at least 85% sequence identity to SEQ ID NO: 1 |
| 14 | Polynucleotide that has at least 85% sequence identity to SEQ ID NO: 2 | Polynucleotide that has at least 85% sequence identity to SEQ ID NO: 2 |
| 15 | Polynucleotide that has at least 85% sequence identity to SEQ ID NO: 2 | Polynucleotide that has at least 85% sequence identity to SEQ ID NO: 3 |
| 16 | Polynucleotide that has at least 85% sequence identity to SEQ ID NO: 2 | Polynucleotide that has at least 85% sequence identity to SEQ ID NO: 4 |
| 17 | Polynucleotide that has at least 85% sequence identity to SEQ ID NO: 2 | Polynucleotide that has at least 85% sequence identity to SEQ ID NO: 5 |
| 18 | Polynucleotide that has at least 85% sequence identity to SEQ ID NO: 2 | Polynucleotide that has at least 85% sequence identity to SEQ ID NO: 6 |
| 19 | Polynucleotide that has at least 85% sequence identity to SEQ ID NO: 2 | Polynucleotide that has at least 85% sequence identity to SEQ ID NO: 7 |
| 20 | Polynucleotide that has at least 85% sequence identity to SEQ ID NO: 2 | Polynucleotide that has at least 85% sequence identity to SEQ ID NO: 8 |
| 21 | Polynucleotide that has at least 85% sequence identity to SEQ ID NO: 2 | Polynucleotide that has at least 85% sequence identity to SEQ ID NO: 9 |
| 22 | Polynucleotide that has at least 85% sequence identity to SEQ ID NO: 2 | Polynucleotide that has at least 85% sequence identity to SEQ ID NO: 10 |
| 23 | Polynucleotide that has at least 85% sequence identity to SEQ ID NO: 2 | Polynucleotide that has at least 85% sequence identity to SEQ ID NO: 11 |
| 24 | Polynucleotide that has at least 85% sequence identity to SEQ ID NO: 2 | Polynucleotide that has at least 85% sequence identity to SEQ ID NO: 12 |
| 25 | Polynucleotide that has at least 85% sequence identity to SEQ ID NO: 3 | Polynucleotide that has at least 85% sequence identity to SEQ ID NO: 1 |

TABLE 2-continued

Exemplary combinations of polynucleotides useful for incorporation into spacers

| No. | First spacer (SS1) | Second spacer (SS2) |
|---|---|---|
| 26 | Polynucleotide that has at least 85% sequence identity to SEQ ID NO: 3 | Polynucleotide that has at least 85% sequence identity to SEQ ID NO: 2 |
| 27 | Polynucleotide that has at least 85% sequence identity to SEQ ID NO: 3 | Polynucleotide that has at least 85% sequence identity to SEQ ID NO: 3 |
| 28 | Polynucleotide that has at least 85% sequence identity to SEQ ID NO: 3 | Polynucleotide that has at least 85% sequence identity to SEQ ID NO: 4 |
| 29 | Polynucleotide that has at least 85% sequence identity to SEQ ID NO: 3 | Polynucleotide that has at least 85% sequence identity to SEQ ID NO: 5 |
| 30 | Polynucleotide that has at least 85% sequence identity to SEQ ID NO: 3 | Polynucleotide that has at least 85% sequence identity to SEQ ID NO: 6 |
| 31 | Polynucleotide that has at least 85% sequence identity to SEQ ID NO: 3 | Polynucleotide that has at least 85% sequence identity to SEQ ID NO: 7 |
| 32 | Polynucleotide that has at least 85% sequence identity to SEQ ID NO: 3 | Polynucleotide that has at least 85% sequence identity to SEQ ID NO: 8 |
| 33 | Polynucleotide that has at least 85% sequence identity to SEQ ID NO: 3 | Polynucleotide that has at least 85% sequence identity to SEQ ID NO: 9 |
| 34 | Polynucleotide that has at least 85% sequence identity to SEQ ID NO: 3 | Polynucleotide that has at least 85% sequence identity to SEQ ID NO: 10 |
| 35 | Polynucleotide that has at least 85% sequence identity to SEQ ID NO: 3 | Polynucleotide that has at least 85% sequence identity to SEQ ID NO: 11 |
| 36 | Polynucleotide that has at least 85% sequence identity to SEQ ID NO: 3 | Polynucleotide that has at least 85% sequence identity to SEQ ID NO: 12 |
| 37 | Polynucleotide that has at least 85% sequence identity to SEQ ID NO: 4 | Polynucleotide that has at least 85% sequence identity to SEQ ID NO: 1 |
| 38 | Polynucleotide that has at least 85% sequence identity to SEQ ID NO: 4 | Polynucleotide that has at least 85% sequence identity to SEQ ID NO: 2 |
| 39 | Polynucleotide that has at least 85% sequence identity to SEQ ID NO: 4 | Polynucleotide that has at least 85% sequence identity to SEQ ID NO: 3 |
| 40 | Polynucleotide that has at least 85% sequence identity to SEQ ID NO: 4 | Polynucleotide that has at least 85% sequence identity to SEQ ID NO: 4 |
| 41 | Polynucleotide that has at least 85% sequence identity to SEQ ID NO: 4 | Polynucleotide that has at least 85% sequence identity to SEQ ID NO: 5 |
| 42 | Polynucleotide that has at least 85% sequence identity to SEQ ID NO: 4 | Polynucleotide that has at least 85% sequence identity to SEQ ID NO: 6 |
| 43 | Polynucleotide that has at least 85% sequence identity to SEQ ID NO: 4 | Polynucleotide that has at least 85% sequence identity to SEQ ID NO: 7 |
| 44 | Polynucleotide that has at least 85% sequence identity to SEQ ID NO: 4 | Polynucleotide that has at least 85% sequence identity to SEQ ID NO: 8 |
| 45 | Polynucleotide that has at least 85% sequence identity to SEQ ID NO: 4 | Polynucleotide that has at least 85% sequence identity to SEQ ID NO: 9 |
| 46 | Polynucleotide that has at least 85% sequence identity to SEQ ID NO: 4 | Polynucleotide that has at least 85% sequence identity to SEQ ID NO: 10 |
| 47 | Polynucleotide that has at least 85% sequence identity to SEQ ID NO: 4 | Polynucleotide that has at least 85% sequence identity to SEQ ID NO: 11 |
| 48 | Polynucleotide that has at least 85% sequence identity to SEQ ID NO: 4 | Polynucleotide that has at least 85% sequence identity to SEQ ID NO: 12 |
| 49 | Polynucleotide that has at least 85% sequence identity to SEQ ID NO: 5 | Polynucleotide that has at least 85% sequence identity to SEQ ID NO: 1 |
| 50 | Polynucleotide that has at least 85% sequence identity to SEQ ID NO: 5 | Polynucleotide that has at least 85% sequence identity to SEQ ID NO: 2 |
| 51 | Polynucleotide that has at least 85% sequence identity to SEQ ID NO: 5 | Polynucleotide that has at least 85% sequence identity to SEQ ID NO: 3 |
| 52 | Polynucleotide that has at least 85% sequence identity to SEQ ID NO: 5 | Polynucleotide that has at least 85% sequence identity to SEQ ID NO: 4 |
| 53 | Polynucleotide that has at least 85% sequence identity to SEQ ID NO: 5 | Polynucleotide that has at least 85% sequence identity to SEQ ID NO: 5 |
| 54 | Polynucleotide that has at least 85% sequence identity to SEQ ID NO: 5 | Polynucleotide that has at least 85% sequence identity to SEQ ID NO: 6 |
| 55 | Polynucleotide that has at least 85% sequence identity to SEQ ID NO: 5 | Polynucleotide that has at least 85% sequence identity to SEQ ID NO: 7 |
| 56 | Polynucleotide that has at least 85% sequence identity to SEQ ID NO: 5 | Polynucleotide that has at least 85% sequence identity to SEQ ID NO: 8 |
| 57 | Polynucleotide that has at least 85% sequence identity to SEQ ID NO: 5 | Polynucleotide that has at least 85% sequence identity to SEQ ID NO: 9 |
| 58 | Polynucleotide that has at least 85% sequence identity to SEQ ID NO: 5 | Polynucleotide that has at least 85% sequence identity to SEQ ID NO: 10 |
| 59 | Polynucleotide that has at least 85% sequence identity to SEQ ID NO: 5 | Polynucleotide that has at least 85% sequence identity to SEQ ID NO: 11 |
| 60 | Polynucleotide that has at least 85% sequence identity to SEQ ID NO: 5 | Polynucleotide that has at least 85% sequence identity to SEQ ID NO: 12 |
| 61 | Polynucleotide that has at least 85% sequence identity to SEQ ID NO: 6 | Polynucleotide that has at least 85% sequence identity to SEQ ID NO: 1 |
| 62 | Polynucleotide that has at least 85% sequence identity to SEQ ID NO: 6 | Polynucleotide that has at least 85% sequence identity to SEQ ID NO: 2 |
| 63 | Polynucleotide that has at least 85% sequence identity to SEQ ID NO: 6 | Polynucleotide that has at least 85% sequence identity to SEQ ID NO: 3 |

TABLE 2-continued

Exemplary combinations of polynucleotides useful for incorporation into spacers

| No. | First spacer (SS1) | Second spacer (SS2) |
|---|---|---|
| 64 | Polynucleotide that has at least 85% sequence identity to SEQ ID NO: 6 | Polynucleotide that has at least 85% sequence identity to SEQ ID NO: 4 |
| 65 | Polynucleotide that has at least 85% sequence identity to SEQ ID NO: 6 | Polynucleotide that has at least 85% sequence identity to SEQ ID NO: 5 |
| 66 | Polynucleotide that has at least 85% sequence identity to SEQ ID NO: 6 | Polynucleotide that has at least 85% sequence identity to SEQ ID NO: 6 |
| 67 | Polynucleotide that has at least 85% sequence identity to SEQ ID NO: 6 | Polynucleotide that has at least 85% sequence identity to SEQ ID NO: 7 |
| 68 | Polynucleotide that has at least 85% sequence identity to SEQ ID NO: 6 | Polynucleotide that has at least 85% sequence identity to SEQ ID NO: 8 |
| 69 | Polynucleotide that has at least 85% sequence identity to SEQ ID NO: 6 | Polynucleotide that has at least 85% sequence identity to SEQ ID NO: 9 |
| 70 | Polynucleotide that has at least 85% sequence identity to SEQ ID NO: 6 | Polynucleotide that has at least 85% sequence identity to SEQ ID NO: 10 |
| 71 | Polynucleotide that has at least 85% sequence identity to SEQ ID NO: 6 | Polynucleotide that has at least 85% sequence identity to SEQ ID NO: 11 |
| 72 | Polynucleotide that has at least 85% sequence identity to SEQ ID NO: 6 | Polynucleotide that has at least 85% sequence identity to SEQ ID NO: 12 |
| 73 | Polynucleotide that has at least 85% sequence identity to SEQ ID NO: 7 | Polynucleotide that has at least 85% sequence identity to SEQ ID NO: 1 |
| 74 | Polynucleotide that has at least 85% sequence identity to SEQ ID NO: 7 | Polynucleotide that has at least 85% sequence identity to SEQ ID NO: 2 |
| 75 | Polynucleotide that has at least 85% sequence identity to SEQ ID NO: 7 | Polynucleotide that has at least 85% sequence identity to SEQ ID NO: 3 |
| 76 | Polynucleotide that has at least 85% sequence identity to SEQ ID NO: 7 | Polynucleotide that has at least 85% sequence identity to SEQ ID NO: 4 |
| 77 | Polynucleotide that has at least 85% sequence identity to SEQ ID NO: 7 | Polynucleotide that has at least 85% sequence identity to SEQ ID NO: 5 |
| 78 | Polynucleotide that has at least 85% sequence identity to SEQ ID NO: 7 | Polynucleotide that has at least 85% sequence identity to SEQ ID NO: 6 |
| 79 | Polynucleotide that has at least 85% sequence identity to SEQ ID NO: 7 | Polynucleotide that has at least 85% sequence identity to SEQ ID NO: 7 |
| 80 | Polynucleotide that has at least 85% sequence identity to SEQ ID NO: 7 | Polynucleotide that has at least 85% sequence identity to SEQ ID NO: 8 |
| 81 | Polynucleotide that has at least 85% sequence identity to SEQ ID NO: 7 | Polynucleotide that has at least 85% sequence identity to SEQ ID NO: 9 |
| 82 | Polynucleotide that has at least 85% sequence identity to SEQ ID NO: 7 | Polynucleotide that has at least 85% sequence identity to SEQ ID NO: 10 |
| 83 | Polynucleotide that has at least 85% sequence identity to SEQ ID NO: 7 | Polynucleotide that has at least 85% sequence identity to SEQ ID NO: 11 |
| 84 | Polynucleotide that has at least 85% sequence identity to SEQ ID NO: 7 | Polynucleotide that has at least 85% sequence identity to SEQ ID NO: 12 |
| 85 | Polynucleotide that has at least 85% sequence identity to SEQ ID NO: 8 | Polynucleotide that has at least 85% sequence identity to SEQ ID NO: 1 |
| 86 | Polynucleotide that has at least 85% sequence identity to SEQ ID NO: 8 | Polynucleotide that has at least 85% sequence identity to SEQ ID NO: 2 |
| 87 | Polynucleotide that has at least 85% sequence identity to SEQ ID NO: 8 | Polynucleotide that has at least 85% sequence identity to SEQ ID NO: 3 |
| 88 | Polynucleotide that has at least 85% sequence identity to SEQ ID NO: 8 | Polynucleotide that has at least 85% sequence identity to SEQ ID NO: 4 |
| 89 | Polynucleotide that has at least 85% sequence identity to SEQ ID NO: 8 | Polynucleotide that has at least 85% sequence identity to SEQ ID NO: 5 |
| 90 | Polynucleotide that has at least 85% sequence identity to SEQ ID NO: 8 | Polynucleotide that has at least 85% sequence identity to SEQ ID NO: 6 |
| 91 | Polynucleotide that has at least 85% sequence identity to SEQ ID NO: 8 | Polynucleotide that has at least 85% sequence identity to SEQ ID NO: 7 |
| 92 | Polynucleotide that has at least 85% sequence identity to SEQ ID NO: 8 | Polynucleotide that has at least 85% sequence identity to SEQ ID NO: 8 |
| 93 | Polynucleotide that has at least 85% sequence identity to SEQ ID NO: 8 | Polynucleotide that has at least 85% sequence identity to SEQ ID NO: 9 |
| 94 | Polynucleotide that has at least 85% sequence identity to SEQ ID NO: 8 | Polynucleotide that has at least 85% sequence identity to SEQ ID NO: 10 |
| 95 | Polynucleotide that has at least 85% sequence identity to SEQ ID NO: 8 | Polynucleotide that has at least 85% sequence identity to SEQ ID NO: 11 |
| 96 | Polynucleotide that has at least 85% sequence identity to SEQ ID NO: 8 | Polynucleotide that has at least 85% sequence identity to SEQ ID NO: 12 |
| 97 | Polynucleotide that has at least 85% sequence identity to SEQ ID NO: 9 | Polynucleotide that has at least 85% sequence identity to SEQ ID NO: 1 |
| 98 | Polynucleotide that has at least 85% sequence identity to SEQ ID NO: 9 | Polynucleotide that has at least 85% sequence identity to SEQ ID NO: 2 |
| 99 | Polynucleotide that has at least 85% sequence identity to SEQ ID NO: 9 | Polynucleotide that has at least 85% sequence identity to SEQ ID NO: 3 |
| 100 | Polynucleotide that has at least 85% sequence identity to SEQ ID NO: 9 | Polynucleotide that has at least 85% sequence identity to SEQ ID NO: 4 |
| 101 | Polynucleotide that has at least 85% sequence identity to SEQ ID NO: 9 | Polynucleotide that has at least 85% sequence identity to SEQ ID NO: 5 |

TABLE 2-continued

Exemplary combinations of polynucleotides useful for incorporation into spacers

| No. | First spacer (SS1) | Second spacer (SS2) |
|---|---|---|
| 102 | Polynucleotide that has at least 85% sequence identity to SEQ ID NO: 9 | Polynucleotide that has at least 85% sequence identity to SEQ ID NO: 6 |
| 103 | Polynucleotide that has at least 85% sequence identity to SEQ ID NO: 9 | Polynucleotide that has at least 85% sequence identity to SEQ ID NO: 7 |
| 104 | Polynucleotide that has at least 85% sequence identity to SEQ ID NO: 9 | Polynucleotide that has at least 85% sequence identity to SEQ ID NO: 8 |
| 105 | Polynucleotide that has at least 85% sequence identity to SEQ ID NO: 9 | Polynucleotide that has at least 85% sequence identity to SEQ ID NO: 9 |
| 106 | Polynucleotide that has at least 85% sequence identity to SEQ ID NO: 9 | Polynucleotide that has at least 85% sequence identity to SEQ ID NO: 10 |
| 107 | Polynucleotide that has at least 85% sequence identity to SEQ ID NO: 9 | Polynucleotide that has at least 85% sequence identity to SEQ ID NO: 11 |
| 108 | Polynucleotide that has at least 85% sequence identity to SEQ ID NO: 9 | Polynucleotide that has at least 85% sequence identity to SEQ ID NO: 12 |
| 109 | Polynucleotide that has at least 85% sequence identity to SEQ ID NO: 10 | Polynucleotide that has at least 85% sequence identity to SEQ ID NO: 1 |
| 110 | Polynucleotide that has at least 85% sequence identity to SEQ ID NO: 10 | Polynucleotide that has at least 85% sequence identity to SEQ ID NO: 2 |
| 111 | Polynucleotide that has at least 85% sequence identity to SEQ ID NO: 10 | Polynucleotide that has at least 85% sequence identity to SEQ ID NO: 3 |
| 112 | Polynucleotide that has at least 85% sequence identity to SEQ ID NO: 10 | Polynucleotide that has at least 85% sequence identity to SEQ ID NO: 4 |
| 113 | Polynucleotide that has at least 85% sequence identity to SEQ ID NO: 10 | Polynucleotide that has at least 85% sequence identity to SEQ ID NO: 5 |
| 114 | Polynucleotide that has at least 85% sequence identity to SEQ ID NO: 10 | Polynucleotide that has at least 85% sequence identity to SEQ ID NO: 6 |
| 115 | Polynucleotide that has at least 85% sequence identity to SEQ ID NO: 10 | Polynucleotide that has at least 85% sequence identity to SEQ ID NO: 7 |
| 116 | Polynucleotide that has at least 85% sequence identity to SEQ ID NO: 10 | Polynucleotide that has at least 85% sequence identity to SEQ ID NO: 8 |
| 117 | Polynucleotide that has at least 85% sequence identity to SEQ ID NO: 10 | Polynucleotide that has at least 85% sequence identity to SEQ ID NO: 9 |
| 118 | Polynucleotide that has at least 85% sequence identity to SEQ ID NO: 10 | Polynucleotide that has at least 85% sequence identity to SEQ ID NO: 10 |
| 119 | Polynucleotide that has at least 85% sequence identity to SEQ ID NO: 10 | Polynucleotide that has at least 85% sequence identity to SEQ ID NO: 11 |
| 120 | Polynucleotide that has at least 85% sequence identity to SEQ ID NO: 10 | Polynucleotide that has at least 85% sequence identity to SEQ ID NO: 12 |
| 121 | Polynucleotide that has at least 85% sequence identity to SEQ ID NO: 11 | Polynucleotide that has at least 85% sequence identity to SEQ ID NO: 1 |
| 122 | Polynucleotide that has at least 85% sequence identity to SEQ ID NO: 11 | Polynucleotide that has at least 85% sequence identity to SEQ ID NO: 2 |
| 123 | Polynucleotide that has at least 85% sequence identity to SEQ ID NO: 11 | Polynucleotide that has at least 85% sequence identity to SEQ ID NO: 3 |
| 124 | Polynucleotide that has at least 85% sequence identity to SEQ ID NO: 11 | Polynucleotide that has at least 85% sequence identity to SEQ ID NO: 4 |
| 125 | Polynucleotide that has at least 85% sequence identity to SEQ ID NO: 11 | Polynucleotide that has at least 85% sequence identity to SEQ ID NO: 5 |
| 126 | Polynucleotide that has at least 85% sequence identity to SEQ ID NO: 11 | Polynucleotide that has at least 85% sequence identity to SEQ ID NO: 6 |
| 127 | Polynucleotide that has at least 85% sequence identity to SEQ ID NO: 11 | Polynucleotide that has at least 85% sequence identity to SEQ ID NO: 7 |
| 128 | Polynucleotide that has at least 85% sequence identity to SEQ ID NO: 11 | Polynucleotide that has at least 85% sequence identity to SEQ ID NO: 8 |
| 129 | Polynucleotide that has at least 85% sequence identity to SEQ ID NO: 11 | Polynucleotide that has at least 85% sequence identity to SEQ ID NO: 9 |
| 130 | Polynucleotide that has at least 85% sequence identity to SEQ ID NO: 11 | Polynucleotide that has at least 85% sequence identity to SEQ ID NO: 10 |
| 131 | Polynucleotide that has at least 85% sequence identity to SEQ ID NO: 11 | Polynucleotide that has at least 85% sequence identity to SEQ ID NO: 11 |
| 132 | Polynucleotide that has at least 85% sequence identity to SEQ ID NO: 11 | Polynucleotide that has at least 85% sequence identity to SEQ ID NO: 12 |
| 133 | Polynucleotide that has at least 85% sequence identity to SEQ ID NO: 12 | Polynucleotide that has at least 85% sequence identity to SEQ ID NO: 1 |
| 134 | Polynucleotide that has at least 85% sequence identity to SEQ ID NO: 12 | Polynucleotide that has at least 85% sequence identity to SEQ ID NO: 2 |
| 135 | Polynucleotide that has at least 85% sequence identity to SEQ ID NO: 12 | Polynucleotide that has at least 85% sequence identity to SEQ ID NO: 3 |
| 136 | Polynucleotide that has at least 85% sequence identity to SEQ ID NO: 12 | Polynucleotide that has at least 85% sequence identity to SEQ ID NO: 4 |
| 137 | Polynucleotide that has at least 85% sequence identity to SEQ ID NO: 12 | Polynucleotide that has at least 85% sequence identity to SEQ ID NO: 5 |
| 138 | Polynucleotide that has at least 85% sequence identity to SEQ ID NO: 12 | Polynucleotide that has at least 85% sequence identity to SEQ ID NO: 6 |
| 139 | Polynucleotide that has at least 85% sequence identity to SEQ ID NO: 12 | Polynucleotide that has at least 85% sequence identity to SEQ ID NO: 7 |

TABLE 2-continued

Exemplary combinations of polynucleotides useful for incorporation into spacers

| No. | First spacer (SS1) | Second spacer (SS2) |
|---|---|---|
| 140 | Polynucleotide that has at least 85% sequence identity to SEQ ID NO: 12 | Polynucleotide that has at least 85% sequence identity to SEQ ID NO: 8 |
| 141 | Polynucleotide that has at least 85% sequence identity to SEQ ID NO: 12 | Polynucleotide that has at least 85% sequence identity to SEQ ID NO: 9 |
| 142 | Polynucleotide that has at least 85% sequence identity to SEQ ID NO: 12 | Polynucleotide that has at least 85% sequence identity to SEQ ID NO: 10 |
| 143 | Polynucleotide that has at least 85% sequence identity to SEQ ID NO: 12 | Polynucleotide that has at least 85% sequence identity to SEQ ID NO: 11 |
| 144 | Polynucleotide that has at least 85% sequence identity to SEQ ID NO: 12 | Polynucleotide that has at least 85% sequence identity to SEQ ID NO: 12 |

It may be desirable to modify a spacer so as to reduce CpG content to below a particular threshold, e.g., below 2% CpG content. For example, a spacer may be a variant of either the human AAVS1 site or a sequence within the AAVS1 locus that exhibits reduced CpG content relative to the corresponding wild type sequence. Manipulation of the CpG content of a spacer can be carried out using established molecular biology techniques known in the art, such as cassette-based and site-directed mutagenesis procedures. In some embodiments, the spacer contains a portion of the human AAVS1 locus, and the CpG content of this spacer is reduced by eliminating cytosine- and guanine-containing nucleotides located in regions of the AAVS1 sequence that are not necessary for Rep-binding or viral genome integration. For instance, a spacer may be an AAVS1 sequence or a portion thereof that has been manipulated so as to retain affinity for an adenoviral Rep protein and to contain less than 2% CpG content (e.g., less than 1%, 0.95%, 0.9%, 0.85%, 0.8%, 0.75%, 0.7%, 0.65%, 0.6%, 0.55%, 0.5%, 0.45%, 0.4%, 0.35%, 0.3%, 0.25%, 0.2%, 0.15%, or 0.1% CpG content). In some embodiments, a spacer contains an AAVS1 sequence or a portion thereof that has been manipulated so as to retain the ability to promote integration of neighboring DNA into a chromosome of a host cell, such as human chromosome 19, and to contain less than 2% CpG content (e.g., less than 1%, 0.95%, 0.9%, 0.85%, 0.8%, 0.75%, 0.7%, 0.65%, 0.6%, 0.55%, 0.5%, 0.45%, 0.4%, 0.35%, 0.3%, 0.25%, 0.2%, 0.15%, or 0.1% CpG content).

Spacers may be of an appropriate length to reduce or prevent packaging of contaminant nucleic acids. For example, the spacer (e.g., SS1 or SS2) may be in the range of about 2.0 Kb to about 5.0 Kb in length; about 2.5 Kb to about 4.5 Kb in length; about 3.0 Kb to about 4.0 Kb in length; or about 3.0 Kb to about 3.5 Kb in length. The length of a first spacer and a second spacer may be equivalent (e.g., SS1 is about 3.0 Kb and SS2 is about 3.0 Kb in length) or different (e.g., SS1 is about 4.0 Kb in length and SS2 is about 5.0 Kb in length). The length of a first spacer and a second spacer may vary according to the vector. The total length of a first spacer and a second spacer together may be in the range of about 4.0 Kb to about 10.0 Kb in length. For example, a first spacer and a second spacer together may be in the range of about 4.0 Kb to about 10.0 Kb in length; about 5.0 Kb to about 9.0 Kb in length; about 6.0 Kb to about 8.0 Kb in length; or about 6.0 Kb to about 7.0 Kb in length.

The length of a spacer may be further selected to accommodate for the size of a desired nucleic acid molecule to be inserted between ITR1 and ITR2. For example, an AAV particle has a packaging capacity for a nucleic acid molecule of about 4.7 Kb. If a desired heterologous polynucleotide of about 3.0 Kb in length is to be inserted into the nucleic acid molecule that will be packaged in an AAV particle, the first spacer and/or the second spacer may be about 2.0 Kb in length. Thus, the heterologous polynucleotide and either the first spacer or second spacer together will have a length of about 5.0 Kb in length. For spacer molecules, a first spacer or a second spacer together with a heterologous polynucleotide may be about 5.0 Kb in length to about 10.0 Kb in length; about 5.5 Kb in length to about 9.5 Kb in length; about 6.0 Kb in length to about 9.0 Kb in length; about 6.5 Kb in length to about 8.5 Kb in length; or about 7.0 Kb in length to about 8.0 Kb in length. The first spacer, second spacer, and the heterologous polynucleotide together may be about 10.0 Kb in length to about 15.0 Kb in length; about 10.5 Kb in length to about 14.5 Kb in length; about 11.0 Kb in length to about 14.0 Kb in length; about 11.5 Kb in length to about 13.5 Kb in length; or about 12.0 Kb in length to about 13.0 Kb in length.

Concatemers

Nucleic acid constructs may contain, in the 5' to 3' direction, a region including a first inverted terminal repeat, a cloning site or a heterologous polynucleotide molecule that is optionally in combination with one or more of a eukaryotic promoter, polyadenylation site(s), and/or homology arm(s) as described herein, and a second inverted terminal repeat, such that this region is flanked on the 5' and 3' ends by sequences that contain a spacer (SS1 or SS2), such as sequences that each contain different halves of a larger spacer sequence, or a 5' sequence that contains one portion of a larger spacer sequence and a 3' portion that contains the remainder of the larger spacer sequence. In some embodiments, the nucleic acid constructs are double stranded nucleic acids, such as double stranded DNA, and the spacers terminate in oligonucleotide overhangs (e.g., 3-nucleotide overhangs that can be formed by hydrolysis of phosphodiester bonds at an asymmetric restriction site). Nucleic acid constructs of this form can be sequentially ligated to one another so as to form concatemers containing repeating units. For instance, in some embodiments, nucleic acid constructs contain the region described above that is flanked on the 5' and 3' ends by spacers that contain asymmetric restriction sites within the spacer sequences such that, upon digestion of the construct with a restriction endonuclease, the oligonucleotide of the spacer that is cleaved from the 5' end of the construct remains covalently bound at the 3' end of the spacer, and likewise, the oligonucleotide of the spacer that is cleaved from the 3' end of the construct remains covalently bound at the 5' end of the spacer. Polynucleotides of this structure can be sequentially ligated to one another to form concatemers that reconstitute a larger spacer at the 5' and 3' ends of each of the individual repeating ITR1-CS- ITR2 or ITR1-HPM-ITR2 units. Concatemers may contain repeating units, in the 5' to 3' direction, of the form (SS1-ITR1-CS-ITR2-SS2)n where n is an integer, e.g., from about 20 to about 40.

In some embodiments, a heterologous polynucleotide molecule is integrated into these constructs at the cloning site to form constructs of the structure ITR1-HMP-ITR2. These constructs can be similarly flanked at the 5' and 3' end by a spacer that consists of a portion of a larger spacer, such that the larger spacer is reconstituted upon concatenation of these constructs. Concatemers may contain repeating units, in the 5' to 3' direction, of the form (SS1-ITR1-HPM-ITR2-SS2)n where n is an integer from about 20 to about 40. Concatemers may also feature additional sequence elements, such as one or more eukaryotic promoters, polyadenylation sites, and/or homology arms in combination with the heterologous polynucleotide molecules as described herein. For instance, exemplary concatemers include those that have any of the following forms:

(SS1-ITR1-$P_{Euk}$-HPM-ITR2-SS2)$_n$ (SS1-ITR1-$P_{Euk}$-HPM-pA-ITR2-SS2)$_n$ (SS1-ITR1-HR1 -H PM-HR2-1TR2-SS2)$_n$ (SS1-ITR1-HR1-$P_{Euk}$-HPM-HR2-ITR2-SS2)$_n$ in the 5' to 3' direction, where n is independently an integer from about 20 to about 40. In embodiments, the sequence elements (e.g., SS1/SS2, ITR1/2, CS, HPM, $P_{Euk}$, pA, HR1/2) described above are operably linked to one another, e.g., such that the structure and/or function of the individual sequence elements are retained when combined with adjacent polynucleotides.

Cloning Site

The cloning site enables ready removal and/or replacement of individual components in the nucleic acid molecule. A cloning site includes a restriction site that is cleaved by an endonuclease that recognizes the restriction site. For example, one or more (e,g., two, three, four, five, six, seven, eight, nine, or tent) cloning sites may flank a first spacer, a second spacer, a first 1TR, a second 1TR, a eukaryotic promoter, a heterologous polynucleotide, and/or a polyadenylation site. Following cleavage of a cloning site by an endonuclease, the cloning site may be lost upon insertion of a desired nucleic acid molecule. Suitable restriction endonucleases for use in constructing a desired nucleic acid molecule may be identified using information readily available to those of skill in the art in the literature and in a variety of on-line databases, e.g., the REBASE™ database. Suitable restriction endonucleases include those available from a variety of commercial sources including, e.g., New England Biolabs, LifeTechnologies, Roche, Clontech, Stratagene, Amersham, Pharmacia, among others.

Heterologous Polynucleotide Molecules

A nucleic add molecule may be cleaved by a restriction endonuclease at a restriction site to subsequently ligate the ends of the nucleic acid molecule to a heterologous polynucleotide molecule (HPM). Accordingly, a nucleic add molecule may include the above components operably linked to each other in a 5'-to-3' direction as SS1 -ITR1 -HPM-ITR2-SS2, Heterologous polynucleotides may include a polynucleotide that encodes a polypeptide, a polynucleotide that is transcribed into an inhibitory polynucleotide, or a polynucleotide that is not transcribed. Heterologous polynucleotide molecules encoding a polypeptide include, but are not limited to: Factor VIII (FVIII); Factor IX (FIX); fukutin-related protein (FKRP); retinoschisin 1 (RS1); cyclic nucleotide-gated channel alpha-3 (CNGA3); cyclic nucleotide-gated channel beta-3 (CNGB3); retinitis pigmentosa GTPase regulator (RPGR); Vascular endothelial growth factor (VEGF); soluble fms-like tyrosine kinase-1 (sFLT1); sarcoplasmic reticulum $Ca^{2+}$ ATPase (SERCA2a); mitochondrially encoded NADH dehydrogenase 4 (MT-ND4); follistatin (FST); nerve growth factor (NGF); retinal pigment epithelium-specific protein 65 kDa (RPE65); choroideremia (CHM); lipoprotein lipase (LPL); porphobilinogen deaminase (PBGD); S100 calcium binding protein A1 (S100A1); ATP-binding cassette, sub-family A member 4 (ABCR); collagen, type XVIII, alpha 1, (COL18A1); myosin VIIA (MYO7A); angiostatin; line derived neurotrophic factor (GDNF); acid α-glucosidase (GAA); myotubularin 1 (MTM1); α1-antitrypsin (A1AT); arylsulfatase A (ARSA); arylsulfatase B (ARSB); UDP glucuronosyltransferase (UGT1A1); protective protein/cathepsin A (PPCA); cardiac myosin-binding protein C (MYBPC3); calsequestrin 2 (CASQ2); gigaxonin (GAN); N-acetylglucosamine-6-sulfatase (GNS); heparan-alpha-glucosaminide N-acetyltransferase (HGSNAT); α-N-acetylglucosaminidase (NAGLU); N-sulfoglucosamine sulfohydrolase (SGSH); α-L-iduronidase (IDUA); N-acetylgalactosamine 6-sulfatase (GALNS); iduronate 2-sulfatase (IDS); late infantile neuronal ceroid lipofuscinosis (CLN2); neuronal ceroid lipofuscinosis-5 (CLN5); glucose-6-phosphatase catalytic-subunit (G6PC); survival of motor neuron-1 (SMN1); methyl CpG binding protein 2 (MECP2); hexosaminidase A (HEXA); aspartoacylase (ASPA); bifunctional UDP-N-acetylglucosamine 2-epimerase/N-acetylmannosamine kinase (GNE); sarcoglycan, alpha (SGCA); protein O-mannosyltransferase-1 (POMT1); protein O-mannosyltransferase-2 (POMT2); like-glycosyltransferase (LARGE); fukutin (FKTN); isoprenoid synthase domain containing (ISPD); protein O-linked mannose N-acetylglucosaminyltransferase 1 (beta 1,2) (POMGnT1); Glycosyltransferase-like domain containing 2 (GTDC2); polypeptide N-acetylgalactosaminyltransferase 2 (B3GALNT2); dystrophin (DMD); glucuronidase-beta (GUSB); X-linked myotubular myopathy (XLMTM); and mini-dystrophin.

The heterologous polynucleotide may also be used for expression of polypeptides and/or RNA molecules for gene editing. For example, the heterologous polynucleotide molecule may encode for one or more zinc finger nucleases, rneganucleases, CRISPR (e.g., Cas9/guide RNA), or fragments thereof. The heterologous polynucleotide molecule may also encode a donor nucleic acid molecule to be used as a repair template for genome editing. A nucleic acid molecule may include first and second homology arms (HR1 and HR2) of about 30-40 nucleotides in length that has nucleic acid sequence homology with a flanking nucleic acid sequence of a locus being targeted for repair. The inclusion of a first homology arm and a second homology arm that flank a heterologous polynucleotide allow for homologous recombination between, for example, a heterologous polynucleotide encoded donor nucleic acid molecule and the locus for repair. Accordingly, a nucleic add molecule may include the above components linked (e.g., operably linked) to each other in a 5-to-3' direction as: SS1-1TR1-HR1-HPM-HR2-ITR2-SS2.

The heterologous polynucleotide may also encode for an inhibitory polynucleotide, e.g., DNA or RNA. Expression of an inhibitory RNA, for example, can diminish expression of a particular target gene and/or polypeptide. An inhibitory RNA molecule may include a small or short hairpin RNA (shRNA), microRNA (miRNA), small or short interfering (si)RNA, trans-splicing RNA, antisense RNA, or ribozyme. For example, the heterologous polynucleotide may encode an miRNA-128 inhibitory RNA. The heterologous polynucleotide may also encode for a polynucleotide that is not transcribed, e.g., a polynucleotide that lacks a promoter.

Any of the above heterologous polynucleotides may also include naturally and non-naturally occurring variants, e.g., gain and loss of function variants. The nucleic acid sequence of a heterologous polynucleotide may encode for a naturally occurring variant, or the nucleic acid sequence may be modified to generate a non-naturally occurring variant that may have substantially the same, greater or less activity or function than a reference nucleic acid sequence, but at least retain partial activity or function of the reference nucleic acid sequence. For example, a heterologous polynucleotide encoding for a variant of human FIX may retain endogenous activity or provide an enhanced therapeutic effect as a result of a variant.

Non-limiting examples of modifications include one or more nucleic acid substitutions (e.g., 1-3, 3-5, 5-10, 10-15, 15-20, 20-25, 25-30, 30-40, 40-50, 50-100, or more nucleic acids), additions (e.g., insertions or 1-3, 3-5, 5-10, 10-15, 15-20, 20-25, 25-30, 30-40, 40-50, 50-100, or more nucleic acids), and deletions (e.g., subsequences or fragments) of a reference nucleic acid sequence. In particular embodiments, a modified or variant heterologous polynucleotide retains at least part of a function or an activity of an unmodified heterologous polynucleotide. A modified heterologous polynucleotide and subsequent variants can have less than, the same, or greater, but at least a part of, a function or activity of a reference heterologous polynucleotide, for example, as described herein.

The nucleic acid sequence of a naturally and non-naturally occurring variant heterologous polynucleotide will have, e.g., at least about 50% sequence identity, about 70% sequence identity, about 80% sequence identity, about 90% sequence identity, or about 95% sequence identity to the reference nucleic acid sequence. Methods for introducing nucleotide changes in a polynucleotide are known in the art (see, e.g., Sambrook et al. Molecular Cloning: A Laboratory Manual (2007)).

An HPM may be further modified to include a Kozak sequence, an intron, and/or an internal ribosomal entry site (IBES).

Eukaryotic Promoters and Polyadenylation Sites

The HPM of the nucleic acid molecule may be operably linked to a eukaryotic promoter ($P_{Euk}$) (e.g., tissue specific promoter or ubiquitously active promoter) to promote the expression of the HPM in a host cell. The $P_{Euk}$ may be inserted separately or in combination with an HPM into a nucleic acid molecule at a CS. Accordingly, a nucleic acid molecule may include the above components linked (e.g., operably linked) to each other in a 5'-to-3' direction as SS1-ITR1-$P_{Euk}$-HPM-ITR2-SS2.

In some instances, the PEA is a tissue specific promoter that is active in specific cell or tissue (e.g., active in a liver, brain, central nervous system, spinal cord, eye, retina, bone, muscle, lung, pancreas, heart, kidney cell, among others). For instance, if expression in skeletal muscle is desired, a $P_{Euk}$ active in muscle may be used. Exemplary skeletal muscle promoters include those from genes encoding desmin, skeletal α-actin, myosin light chain 2A, dystrophin, muscle creatine kinase, as well as synthetic muscle promoters with activities higher than naturally-occurring promoters (e.g., see Li et al. Nat. Biotech. 17:241 (1999)). Examples of $P_{Euk}$ with liver-specific expression include albumin promoter (see, e.g., Miyatake et al. Virol. 71:5124 (1997); hepatitis B virus core promoter (see, e.g., Sandig et al. Gene Ther. 3:1002 (1996)); α-fetoprotein (AFP) promoter (see, e.g., Arbuthnot et al. Hum. Gene. Ther. 7:1503 (1996)); and apolipoprotein E (ApoE) promoter (see, e.g., Okuyama et al, Hum. Gene Ther. 7: 637 (1996)); the disclosures of each of which are incorporated herein by reference. Examples of $P_{Euk}$ with bone-specific expression include osteocalcin promoter (see, e,g., Stein et al. Mol. Biol, Rep. 24:185 (1997); and bone sialoprotein promoter (see, e.g., Chen et al. Bone Miner, Res. 11 :654 (1996)); the disclosures of each of which are incorporated herein by reference. Examples of $P_{Euk}$ with lymphocyte-specific expression include CD2 promoter (see, e,g., Hansa) et al. Immunol. 161:1063 (1998); the disclosure of which is incorporated herein by reference); immunoglobulin heavy chain promoter, and T cell receptor a chain promoter. Non-limiting examples of Pak with neuronal-specific expression are neuron-specific enolase (NSE) promoter (see, e.g., Andersen et al. Cell, Mel. Neurobiol. 13:503 (1993)); neurofilament light-chain promoter (see, e.g., Piccioli et al. Proc. Natl. Acad. Sci, USA 88:5611 (1991)); the neuron-specific vgf promoter (see, e.g., Piccioli et al. Neuron 15:373 (1995)); and synapsin 1 (Syn1) promoter (see, e.g., Kügler et al. Gene Ther. 10:337 (2003)); the disclosures of each of which are incorporated herein by reference.

In some instances, $P_{Euk}$ is a ubiquitously active promoter/enhancer that is capable of driving expression of a polynucleotide in many different cell types. Exemplary ubiquitously active $P_{Euk}$ include, but are not limited to the cytomegalovirus (CMV) Immediate early promoter/enhancer ; the Rous sarcoma virus (RSV) promoter/enhancer; and the other viral promoters/enhancers active In a variety of mammalian cell types, or synthetic elements that are not present In nature (see, e.g., Boshart et al. Cell 41:521 (1985)); the SV40 promoter, the dhydrofolate reductase promoter; the chicken β-actin promoter; and the phosphoglycerol kinase (PGK) promoter. In embodiments where the heterologous polynucleotide encodes an inhibitory RNA molecule, the $P_{Euk}$ may include a Pol III promoter (e.g., a U6 promoter or H1 promoter).

When a $P_{Euk}$ is combined with an HPM encoding for a polypeptide, the nucleic acid molecule may further include a polyadenylation site (pA). Accordingly, a nucleic acid molecule may include the above components linked (e.g., operably linked) to each other in a 5'-to-3' direction as: SS1-ITR1-Peek-HPM-pA-ITR2-SS2. The pA may include the human β-globin polyadenylation site, the SV40 late polyadenylation site, the SV40 early polyadenylation site, or the bovine growth hormone polyadenylation site.

B. Vectors, Host Cells, and Methods of Production

Vectors

The invention features vectors including any of the nucleic acid molecules described above. In addition to the components of the nucleic acid molecules described in detail above, the vectors may include a cloning site, a bacterial or a mammalian origin of replication, a bacterial, or baculoviral promoter element, and/or a nucleic acid which encodes polypeptides useful as a selection marker (e.g., an antibiotic resistance gene). An antibiotic resistance gene may include, but is not limited to, kanamycin, ampicillin, spectinomycin, streptomycin, carbenicillin, bleomycin, erythromycin, polymyxin B, tetracycline, or chloramphenicol. The selectable marker gene may be expressed from a promoter that contains bacterial or baculoviral transcription factor binding sites. The promoter and selectable marker are operably linked in a 5'-to-3' direction and may be positioned 5'-to (upstream of) a first spacer and/or 3'-to (downstream of) a second spacer. The origin of replication may also be positioned 5'-to (upstream of) a first spacer and/or 3'-to (downstream of) a second spacer. The vectors may include viral vectors that include a nucleic acid molecule that can be packaged into a viral particle. The vector may be circular (e.g., a plasmid) or linear.

Viral Particles

Viral particles include any of the above-mentioned nucleic acid molecules encapsidated into an infectious particle. The nucleic acid molecules include a first spacer and a second spacer (SS1 and SS2) that flank the first and second ITRs (ITR1 and ITR2) of the nucleic acid molecule, which may result in packaging of a spacer molecule. For example, in a plurality of viral particles, some viral particles will include a nucleic acid molecule having a first spacer (SS1) and a first ITR (ITR1); some viral particles will include a nucleic acid molecule having a second spacer (SS2) and a second ITR (ITR2); some viral particles will include ITR1, a heterologous polynucleotide, and ITR2; some viral particles will include a first spacer (SS1), ITR1, a heterologous polynucleotide, and ITR2; and some viral particles will include ITR1, a heterologous polynucleotide, ITR2, and a second spacer (SS2). The inclusion of a first spacer and a second spacer in the nucleic acid molecule helps to minimize the inclusion of additional contaminating nucleic acids (e.g., prokaryotic or baculoviral nucleic acids, a selectable marker, or a nucleic acid having a CpG content that is greater than 2%) present in the vector containing the nucleic acid molecule. For example, in a plurality of viral particles comprising a nucleic acid having an ITR1, heterologous polynucleotide, and ITR2, less than 1% (e.g., less than 0.95%, 0.9%, 0.85%, 0.8%, 0.75%, 0.7%, 0.65%, 0.6%, 0.55%, 0.5%, 0.45%, 0.4%, 0.35%, 0.3%, 0.25%, 0.2%, 0.15%, or 0.1%) of the plurality of viral particles will contain contaminating nucleic acids that include a selectable marker (e.g., antibiotic resistance gene), nucleic acids with a CpG content of greater than 2%, and/or prokaryotic or baculoviral nucleic acids (e.g., origin of replication, transcription factor binding sites, and/or an open reading frame).

Methods of Producing Viral Particles

The method of producing a plurality of viral particles may be performed using any of the vectors described herein. Briefly, the vector is transfected into a host cell, where it may exist transiently. Alternatively, a linear vector is stably integrated into the genome of the host cell, either chromosomally or as an episome. Suitable transfection techniques are known in the art and may readily be utilized to deliver the vector to the host cell. The vectors are cultured in the host cells which express the capsid and/or replication proteins. In the host cells, the nucleic acid molecules contained within the vector are rescued and packaged into the capsid protein or envelope protein to form an infectious viral particle.

Viral genomes provide a source of vectors that can be used for the efficient delivery of exogenous nucleic acids into a host cell. Viral genomes are particularly useful vectors for gene delivery because the polynucleotides contained within such genomes are typically incorporated into the nuclear genome of a host cell by generalized or specialized transduction. These processes occur as part of the natural viral replication cycle, and often do not require added proteins or reagents in order to induce gene integration. Examples of viral vectors include a retrovirus, adenovirus (e.g., Ad5, Ad26, Ad34, Ad35, and Ad48), parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g., measles and Sendai), positive strand RNA viruses, such as picornavirus and alphavirus, and double stranded DNA viruses including herpes virus (e.g., Herpes Simplex virus types 1 and 2, Epstein-Barr virus, cytomegalovirus), and poxvirus (e.g., vaccinia, modified vaccinia Ankara (MVA), fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D-type viruses, HTLV-BLV group, lentivirus, spumavirus (Coffin et al. Retroviridae: The viruses and their replication, in Fields et al. Fundamental Virology, $3^{rd}$ ed. Lippincott-Raven Publishers, Philadelphia, 1996, the disclosure of which is incorporated herein by reference). Other examples of viral vectors include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described in, e.g., U.S. Pat. No. 5,801,030, the disclosure of which is incorporated herein by reference.

Other techniques that can be used to introduce a polynucleotide, such as DNA or RNA (e.g., mRNA, tRNA, siRNA, miRNA, shRNA, chemically modified RNA) into a host cell are well known in the art. For instance, electroporation can be used to permeabilize host cells by the application of an electrostatic potential. Host cells, such as mammalian cells, subjected to an external electric field in this manner are subsequently predisposed to the uptake of exogenous nucleic acids. Electroporation of mammalian cells is described in detail, e.g., in Chu et al. Nucleic Acids Res. 15:1311 (1987), the disclosure of which is incorporated herein by reference. A similar technique, Nucleofection™, utilizes an applied electric field in order to stimulate the uptake of exogenous polynucleotides into the nucleus of a eukaryotic cell. Nucleofection™ and protocols useful for performing this technique are described in detail, e.g., in Distler et al. Exp. Dermatol. 14:315 (2005), as well as in US 2010/0317114, the disclosures of each of which are incorporated herein by reference.

Additional techniques useful for the transfection of host cells include the squeeze-poration methodology. This technique induces the rapid mechanical deformation of cells in order to stimulate the uptake of exogenous DNA through membranous pores that form in response to the applied stress. This technology is advantageous in that a vector is not required for delivery of nucleic acids into a cell, such as a host cell. Sqeeeze-poration is described in detail, e.g., in Sharei et al. J. Vis. Exp. 81:e50980 (2013), the disclosure of which is incorporated herein by reference.

Lipofection represents another technique useful for transfection of host cells. This method involves the loading of nucleic acids into a liposome, which often presents cationic functional groups, such as quaternary or protonated amines, towards the liposome exterior. This promotes electrostatic interactions between the liposome and a cell due to the anionic nature of the cell membrane, which ultimately leads to uptake of the exogenous nucleic acids, e.g., by direct fusion of the liposome with the cell membrane or by endocytosis of the complex. Lipofection is described in detail, e.g., in U.S. Pat. No. 7,442,386, the disclosure of which is incorporated herein by reference. Similar techniques that exploit ionic interactions with the cell membrane to provoke the uptake of foreign nucleic acids include contacting a cell with a cationic polymer-nucleic acid complex. Exemplary cationic molecules that associate with polynucleotides so as to impart a positive charge favorable for interaction with the cell membrane include activated dendrimers (described, e.g., in Dennig, Top. Curr. Chem., 228:227-236 (2003), the disclosure of which is incorporated herein by reference) and diethylaminoethyl (DEAE)-dextran, the use of which as a transfection agent is described in detail, e.g., in, Gulick et al. Curr. Prot. Mol. Biol. 40:1:9.2 (1997), the disclosure of which is incorporated herein by reference. Magnetic beads are another tool that can be used to transfect host cells in a mild and efficient manner, as this methodology utilizes an applied magnetic field in order to direct the uptake of nucleic acids. This technology is described in detail, e.g., in US 2010/0227406, the disclosure of which is incorporated herein by reference.

Another useful tool for inducing the uptake of exogenous nucleic acids by host cells is laserfection, a technique that involves exposing a cell to electromagnetic radiation of a particular wavelength in order to gently permeabilize the cells and allow polynucleotides to penetrate the cell membrane. This technique is described in detail, e.g., in Rhodes et al. Methods Cell. Biol. 82:309 (2007), the disclosure of which is incorporated herein by reference.

In addition to viral vectors and the transformation techniques described above, a variety of other tools have been developed that can be used for the incorporation of exogenous genes into host cells. One such method that can be used for incorporating polynucleotides encoding target genes into host cells involves the use of transposons. Transposons are polynucleotides that encode transposase enzymes and contain a polynucleotide sequence or gene of interest flanked by 5' and 3' excision sites. Once a transposon has been delivered into a cell, expression of the transposase gene commences and results in active enzymes that cleave the gene of interest from the transposon. This activity is mediated by the site-specific recognition of transposon excision sites by the transposase. In some embodiments, these excision sites may be terminal repeats or inverted terminal repeats. Once excised from the transposon, the gene of interest can be integrated into the genome of a host cell, such as a mammalian cell, by transposase-catalyzed cleavage of similar excision sites that exist within the nuclear genome of the cell. This allows the gene of interest to be inserted into the cleaved nuclear DNA at the complementary excision sites, and subsequent covalent ligation of the phosphodiester bonds that join the gene of interest to the DNA of the mammalian cell genome completes the incorporation process. In some embodiments, the transposon may be a retrotransposon, such that the gene encoding the target gene is first transcribed to an RNA product and then reverse-transcribed to DNA before incorporation in the mammalian cell genome. Exemplary transposon systems include the piggybac transposon (described in detail in, e.g., WO 2010/085699) and the sleeping beauty transposon (described in detail in, e.g., US2005/0112764), the disclosures of each of which are incorporated herein by reference.

Generally, when delivering a vector to a host cell (e.g., a prokaryotic cell, such as an E. coli cell, or a eukaryotic cell, such as a mammalian cell or an insect cell), the vector is delivered in an amount ranging from about 5 μg to about 100 μg DNA, about 10 μg to about 50 g of DNA to about $1 \times 10^4$ cells to about $1 \times 10^{13}$ cells, or about $1 \times 10^5$ cells. However, the relative amounts of vector to host cells may be adjusted, taking into consideration such factors as the selected vector, the delivery method, and the host cells selected.

The vectors are useful for a variety of purposes, but are particularly well suited for use in production of a recombinant adeno-associated virus (AAV) containing the nucleic acid molecules described herein. To generate a plurality of adeno-associated viral (AAV) particles containing a nucleic acid of the vector requires the AAV helper functions of the Rep and Cap proteins, and the adenoviral helper functions provided by the products of the adenovirus E2A, E4 and VA genes. The vector, AAV helper vector, and the adenoviral helper nucleic acids may be provided to the host cell in trans. In a two-vector system, the vector can be co-transfected into adenovirus-infected human embryonic kidney 293 (HEK293) cells with an additional vector that provides the AAV helper functions. In a three-vector system, HEK293 cells are transfected with the vector containing a nucleic acid molecule, a vector providing the AAV helper function, and a third vector that substitutes for the wild type adenovirus by providing E2A, E4 and VA adenoviral genes to enable viral replication (e.g., see, Shi et al. Virology J. 6:3 (2009)).

Alternatively, any one or more of the required components (e.g., the vector, rep-encoding nucleic acids, cap-encoding nucleic acids, and/or adenoviral helper functions) may be provided by a stable host cell which has been engineered to contain one or more of the required components using methods known to those of skill in the art. These methods include standard transfection and co-transfection techniques, e.g., calcium phosphate precipitation techniques. Other conventional methods include homologous recombination of the vector nucleic acids, plaquing of viruses in agar overlay, methods of measuring signal generation, among others (see, e.g., Fisher et al. J. Virol. 70:520 (1993); and US 5,478,745). Similarly, methods of generating AAV virions are well known in the art and the selection of a suitable method is not a limitation on the present invention.

The AAV and components described herein may be isolated or obtained from academic, commercial, or public sources (e.g., the American Type Culture Collection, Manassas, Va.). Alternatively, the AAV nucleic acid sequences may be obtained through synthetic or other suitable means by reference to published nucleic acid sequences, e.g., nucleic acid sequences available in the literature or in public databases, e.g., GenBank or PubMed, among others.

The host cell contains the nucleic acids which drive expression of capsid proteins and replication proteins that recognize and bind the ITRs found in the nucleic acid molecule of the vector. For example, AAV cap and rep-encoding nucleic acids may be independently obtained from differing AAV sources and may be introduced into the host cell as described above. Further, the Rep78/68-encoding nucleic acids may be from AAV2, whereas the AAV cap-encoding nucleic acid may be from AAV8.

Thus, in one embodiment, the rep and cap-encoding nucleic acids may be transfected into the host cell on a single nucleic acid molecule and exist stably in the cell as an episome. In another embodiment, the rep and cap-encoding nucleic acids are stably integrated into the chromosome of the host cell. Alternatively, the rep and cap-encoding nucleic acids may be transiently expressed in the host cell. Optionally, the rep and/or cap-encoding nucleic acids may be supplied on a vector that contains other nucleic acid molecules, e.g., adenoviral protein-encoding nucleic acids, that are to be introduced into the host cells.

The packaging host cell also requires helper functions in order to package the viral particles described herein. Optionally, these functions may be supplied by a herpes virus. Most desirably, the necessary helper functions are each provided from a human or non- human primate adenovirus source, such as those described above and/or are available from a variety of sources, including the American Type Culture Collection (ATCC), Manassas, Va. (US). For example, the host cell is provided with and/or contains an E1a gene product, an E1b gene product, an E2a gene product, and/or an E4 ORF6 gene product. The host cell may contain additional adenoviral genes such as VAI RNA, but these genes are not required. In another embodiment, no other adenovirus genes or gene functions are present in the host cell. One or more of the adenoviral genes may be stably integrated into the genome of the host cell, stably expressed as episomes, or expressed transiently.

The host cell itself may be selected from any biological organism, including prokaryotic (e.g., bacterial) cells, and eukaryotic cells, including, insect cells (e.g., SF9), yeast cells and mammalian cells. For example, a bacterial E. coli cell may be used as a host cell to replicate a vector described herein. Host cells may be selected from among any mammalian species, including, without limitation, cells such as A549, WEHI, 3T3, 10T1/2, BH , MDC , COS 1, COS 7, BSC 1, BSC 40, BMT 10, VERO, W138, HeLa, HEK293 cells, Saos, C2C12, L cells, HT1080, HepG2, and mammalian primary fibroblast, hepatocyte, and myoblast cells. The selection of the mammalian species providing the cells is not a limitation of this invention; nor is the type of mammalian cell, i.e., fibroblast, hepatocyte, tumor cell, etc.

The resulting recombinant viral particle that expresses the nucleic acid molecule is particularly well suited to gene delivery for therapeutic purposes. Further, the compositions described herein may also be used for production of a desired gene product in vitro. Methods for producing a viral particle comprising culturing a host cell that comprises one or more of the vector(s) above in a culture medium, and optionally recovering the viral particles from the host cell culture medium, are also provided.

Methods for purifying viral particles containing a nucleic acid molecule or concatemer include ion- exchange chromatography. This technique represents a particularly useful strategy for purification of AAV particles due to the generally low isoelectric point (pI) of AAV capsid proteins. Useful resins for ion exchange chromatography of viral particles, such as AAV particles, include carboxymethyl and sulfopropyl resins, e.g., as described in U.S. Pat. No. 7,419,817, the disclosure of which is incorporated herein by reference.

EXAMPLES

The following are examples of the invention. It is understood that various other embodiments may be practiced, given the general description provided above.

Example 1. Generation of AAV Vectors with Spacers

A spacer was designed for inclusion in an AAV vector. The ubiquitin C locus was selected as a candidate genomic nucleic acid sequence to be included in the AAV vector as a space. The genome browser tool provided by UCSC genome browser was utilized in identifying the CpG content, putative transcription factor binding sites, and open reading frames (ORFs) contained within the UbC locus. A window of 3.0 Kb of the UbC nucleic acid sequence was selected due to its low CpG content (2%), limited putative transcription factor binding sites, and small ORF (90 amino acids). PCR primers of 19 nucleotides in length were designed to bind to and amplify the 3.0 Kb region of the UbC nucleic acid sequence from genomic DNA isolated from HEK293 cells by PCR. The resulting amplification product was gel purified and sequenced by methods known in the art. The isolated genomic UbC nucleic acid sequence was further modified by site-directed mutagenesis (Stratagene) to reduce the CpG content, remove transcription factor binding sites, and reduce the ORF to 50 amino acids.

An AAV pCAT circular parental vector, pCAT-AAV-CMV-GFP, was used as the destination vector for the modified UbC spacer. The parental vector contains a nucleic acid molecule having the following components: a first AAV2 ITR1, a CMV promoter, a 3-globin intron, a GFP encoding polynucleotide, a β-globin polyadenylation site (pA), a second AAV2 ITR2, a prokaryotic origin of replication, and a kanamycin antibiotic selection gene (Kan$^R$). The parental vector also contains a cloning site containing a Pmel restriction endonuclease recognition site 5'-to the first AAV2 ITR1; and a cloning site containing SwaI restriction endonuclease recognition site 3'-to the second AAV2 ITR2. The resulting vector included the nucleic acid components operably linked in a 5'-to-3' direction as: CS-AAV2 ITR1-CMV-β-globin intron-GFP-β-globin pA-AAV2 ITR2-CS-oriC-Kan$^R$. The parental vector was digested with Pmel to introduce blunt ends 5' to a first AAV2 ITR1. The UbC PCR product and digested parental vector were ligated by T4 DNA ligase at 16° C. for 1 hour. Resulting parental vector with a first spacer insertion was sequence verified and subsequently digested with SwaI to introduce blunt ends 3'-to the second AAV2 ITR2. The UbC PCR product and parental vector with one spacer were again ligated and sequence verified as previously described. The resulting vector is shown in FIG. 1 as pAAV-CMV-GFP and contains the following nucleic acid components operably linked in a 5'-to-3' direction as: spacer 1-AAV2 ITR1-CMV-β-globin intron-GFP-β-globin pA-AAV2 ITR2-spacer2-oriC-Kan$^R$.

The two spacer vector was transformed into competent E.coli cells, which were then cultured overnight at 37° C. The two spacer vector was purified by Qiagen mini-prep kits and sequence verified.

The purified spacer vector and parental vector used as a control were co-transfected into HEK293 cells with AAV helper vector and adenoviral helper vector by CaPat transfection. The AAV helper vector includes a nucleic acid molecule encoding for AAV2 Rep proteins and AAV8 capsid proteins. Resulting AAV2/8 spacer and non-spacer viral particles were harvested 48 hours after transfection and purified by ultracentrifugation and column filtration.

Human hepatocyte HepG2 cells were transduced with purified AAV2/8 spacer or non-spacer viral particles and subsequently lysed to isolate genomic DNA from transduced cells. The purified DNA was analyzed PCR for contaminating oriC and KanR nucleic acids. Cells transduced with AAV2/8 spacer viral particles contained less than 1% of contaminating oriC or KanR nucleic acids, while cells transduced with AAV2/8 non-spacer viral particles contained 3% contaminating oriC or KanR nucleic acids.

Example 2. Production of Concatemers by Ligation of Restriction Digest Fragments An exemplary procedure useful for the production of concatemers containing a plurality of copies of a nucleic acid molecule involves the ligation of DNA constructs that terminate in non-palindromic oligonucleotide overhangs. For instance, one can produce a concatemer by incubating a restriction endonuclease with a DNA cassette that contains, in the 5'-to-3' direction, a first spacer (SS1), a first inverted terminal repeat (ITR1), a heterologous polynucleotide molecule (HPM), a second inverted terminal repeat (ITR2), and a second spacer (SS2), such that the SS1 and SS2 sequences contain a restriction site at which phosphodiester bonds of the nucleic acid framework are cleaved. In preferred embodiments, the restriction site is an asymmetric restriction site, such as one that is cleaved by such restriction endonucleases as SfiI and Pf/MI. Cleavage at an asymmetric restriction site results in nucleic acid molecules that terminate in non-palindromic overhang sequences, for example, of from 3 to 5 nucleotides in length. Non-palindromic overhangs of this structure can be used to selectively direct the ligation of a first copy of the nucleic acid molecule to a second copy of the nucleic acid molecule in a head-to-tail orientation. Methods for the ligation of multiple copies of nucleic acid molecules that contain complementary overhangs at the 5' and 3' ends of the sequence to another are known in the art. Exemplary reagents that can be used to ligate DNA molecules of this sort to one another include DNA ligase, such as T4 DNA ligase. Commercial kits useful for the ligation of DNA fragments include the Quick Ligation™ Kit (New England Biolabs, Ipswich, Mass., USA).

Example 3. Isolation of Viral Particles Containing Nucleic Acid Molecules

Viral particles containing nucleic acid molecules can be obtained by producing viral particles in a host cell, such as a packaging cell, and subsequently purifying the viral particles from the cell culture medium containing such host cells. For instance, nucleic acid molecules or concatemers can be transfected into a packaging cell, such as a HEK293 cell or a HeLa cell, using established transfection techniques known in the art (e.g., by transformation or transduction techniques described herein).

Following the introduction of these nucleic acid constructs into the host cell of interest, one can culture the host cell using techniques known in the art in order to promote the proliferation of the host cells and the production of viral particles containing a nucleic acid molecule. For example, AAV particles can be produced by transfecting a packaging cell with a nucleic acid molecule or concatemer and subsequently culturing the packaging cell in an appropriate cell culture medium. After culturing for a period of time (e.g., 24 hours, 48 hours, or 72 hours) the viral particles can be isolated from the culture medium using standard molecular biology techniques known in the art.

One common technique useful for the purification of viral particles, such as AAV particles, from cell culture media involves ion-exchange chromatography, in particular cation exchange chromatography. AAV capsid proteins generally exhibit pI values of approximately 6.3, and in the presence of an acidic buffer (pH of from about 3 to about 4) can be readily separated on the basis of their positive charge from other components of the cell culture medium. Exemplary cation exchange resins useful for the purification of AAV particles include carboxymethyl and sulfopropyl resins. Elution of AAV particles from resins that present such functionality can be accomplished using established protocols known in the art, such as by contacting the resin with a solution buffered at a pH nearly equal to the pI of the AAV capsid of interest (e.g., a citrate buffer at a pH of about 6.0). At this pH, capsid proteins are increasingly deprotonated and the ionic association between the capsid proteins and the chromatography resin is attenuated as the pH of the eluant is increased. The recovery of AAV particles from a cell culture medium can be monitored using a variety of standard procedures, for instance, by observing the absorbance of the eluate at 280 nm, a spectroscopic signature that is characteristic of proteins due to the UV absorbance of aromatic amino acids, such as tyrosine and tryptophan.

Other Embodiments

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A nucleic acid molecule comprising:
(i) a first spacer (SS1);
(ii) a first inverted terminal repeat (ITR1);
(iii) a cloning site (CS);
(iv) a second inverted terminal repeat (ITR2); and
(v) a second spacer (SS2);
operably linked to each other in a 5'-to-3' direction as: SS1-ITR1-CS-ITR2-SS2, wherein the SS1 and the SS2 each, independently, comprise a portion having a nucleic acid sequence that is at least 85% identical to any one of the nucleic acid sequences of SEQ ID NOS: 3-5 and 9-11, and wherein neither the SS1 nor the SS2 comprises an open reading frame that encodes more than 100 amino acids.

2. The nucleic acid of claim 1, wherein the SS1 has the nucleic acid sequence of SEQ ID NO: 3.

3. The nucleic acid of claim 2, wherein the SS2 has the nucleic acid sequence of SEQ ID NO: 4.

4. The nucleic acid of claim 1, wherein the SS2 has the nucleic acid sequence of SEQ ID NO: 3.

5. The nucleic acid of claim 1, wherein the SS1 has the nucleic acid sequence of SEQ ID NO: 4.

6. The nucleic acid of claim 5, wherein the SS2 has the nucleic acid sequence of SEQ ID NO: 3.

7. The nucleic acid of claim 1, wherein the SS2 has the nucleic acid sequence of SEQ ID NO: 4.

8. A nucleic acid molecule comprising:
(i) a SS1;
(ii) an ITR1;
(iii) a heterologous polynucleotide molecule (HPM);
(iv) an ITR2; and
(v) a SS2;
operably linked to each other in a 5'-to-3' direction as: SS1-ITR1-HPM-ITR2-SS2, wherein the SS1 and the SS2 each, independently, comprise a portion having a nucleic acid sequence that is at least 85% identical to any one of the nucleic acid sequences of SEQ ID NOS: 3-5 and 9-11, and wherein neither the SS1 nor the SS2 comprises an open reading frame that encodes more than 100 amino acids.

9. The nucleic acid molecule of claim 8, wherein the SS1 and/or the SS2 comprises a portion having a nucleic acid sequence that is at least 85% identical to the nucleic acid sequence of SEQ ID NO: 3.

10. The nucleic acid molecule of claim 8, wherein the SS1 and/or the SS2 has a nucleic acid sequence that is at least 85% identical to the nucleic acid sequence of SEQ ID NO: 1 or a portion thereof, wherein said portion has the nucleic acid sequence of SEQ ID NO: 3.

11. The nucleic acid molecule of claim 8, wherein the SS1 and/or the SS2 comprises a portion having a nucleic acid sequence that is at least 85% identical to the nucleic acid sequence of SEQ ID NO: 4.

12. The nucleic acid molecule of claim 8, wherein the SS1 and/or the SS2 has a nucleic acid sequence that is at least 85% identical to the nucleic acid sequence of SEQ ID NO: 2 or a portion thereof, wherein said portion has the nucleic acid sequence of SEQ ID NO: 4.

13. The nucleic acid molecule of claim 8, wherein the SS1 has a nucleic acid sequence that is at least 85% identical to the nucleic acid sequence of SEQ ID NO: 1, or a portion thereof that has the nucleic acid sequence of SEQ ID NO: 3, and wherein the SS2 has a nucleic acid sequence that is at least 85% identical to the nucleic acid sequence of SEQ ID NO: 2, or a portion thereof that has the nucleic acid sequence of SEQ ID NO: 4.

14. The nucleic acid molecule of claim 8, wherein the SS1 has a nucleic acid sequence that is at least 85% identical to the nucleic acid sequence of SEQ ID NO: 2, or a portion thereof that has the nucleic acid sequence of SEQ ID NO: 4, and wherein the SS2 has a nucleic acid sequence that is at least 85% identical to the nucleic acid sequence of SEQ ID NO: 1, or a portion thereof that has the nucleic acid sequence of SEQ ID NO: 3.

15. The nucleic acid molecule of claim 8, wherein the SS1 and/or the SS2 comprises a portion having a nucleic acid sequence that is at least 85% identical to the nucleic acid sequence of SEQ ID NO: 5.

16. The nucleic acid molecule of claim 8, wherein the SS1 and/or the SS2 has a nucleic acid sequence that is at least 85% identical to the nucleic acid sequence of SEQ ID NO: 6 or a portion thereof, wherein said portion has the nucleic acid sequence of SEQ ID NO: 5.

17. The nucleic acid molecule of claim 8, wherein the SS1 and/or the SS2 comprises a portion having a nucleic acid sequence that is at least 85% identical to the nucleic acid sequence of SEQ ID NO: 9.

18. The nucleic acid molecule of claim 8, wherein the SS1 and/or the SS2 has a nucleic acid sequence that is at least 85% identical to the nucleic acid sequence of SEQ ID NO: 7 or a portion thereof, wherein said portion has the nucleic acid sequence of SEQ ID NO: 9.

19. The nucleic acid molecule of claim 8, wherein the SS1 and/or the SS2 comprises a portion having a nucleic acid sequence that is at least 85% identical to the nucleic acid sequence of SEQ ID NO: 10.

20. The nucleic acid molecule of claim 8, wherein the SS1 and/or the SS2 has a nucleic acid sequence that is at least 85% identical to the nucleic acid sequence of SEQ ID NO: 8 or a portion thereof, wherein said portion has the nucleic acid sequence of SEQ ID NO: 10.

21. The nucleic acid molecule of claim 8, wherein the SS1 has a nucleic acid sequence that is at least 85% identical to the nucleic acid sequence of SEQ ID NO: 7, or a portion thereof that has the nucleic acid sequence of SEQ ID NO: 9, and wherein the SS2 has a nucleic acid sequence that is at least 85% identical to the nucleic acid sequence of SEQ ID NO: 8, or a portion thereof that has the nucleic acid sequence of SEQ ID NO: 10.

22. The nucleic acid molecule of claim 8, wherein the SS1 has a nucleic acid sequence that is at least 85% identical to the nucleic acid sequence of SEQ ID NO: 8, or a portion thereof that has the nucleic acid sequence of SEQ ID NO: 10, and wherein the SS2 has a nucleic acid sequence that is at least 85% identical to the nucleic acid sequence of SEQ ID NO: 7, or a portion thereof that has the nucleic acid sequence of SEQ ID NO: 9.

23. The nucleic acid molecule of claim 8, wherein the SS1 and/or the SS2 comprises a portion having a nucleic acid sequence that is at least 85% identical to the nucleic acid sequence of SEQ ID NO: 11.

24. The nucleic acid molecule of claim 8, wherein the SS1 and/or the SS2 has a nucleic acid sequence that is at least 85% identical to the nucleic acid sequence of SEQ ID NO: 12 or a portion thereof, wherein said portion has the nucleic acid sequence of SEQ ID NO: 11.

25. The nucleic acid molecule of claim 8, wherein neither the SS1 nor the SS2 comprises an open reading frame that encodes more than 50 amino acids.

26. The nucleic acid molecule of claim 8, wherein the SS1 and/or the SS2 does not comprise a prokaryotic or a baculoviral transcription factor binding site.

27. The nucleic acid molecule of claim 8, wherein the SS1 and/or the SS2 comprises a total CpG content that is less than 1% of the total nucleic acid sequence of the SS1 and/or the SS2.

28. The nucleic acid molecule of claim 27, wherein the SS1 and/or the SS2 comprises a total CpG content that is less than 0.5% of the total nucleic acid sequence of the SS1 and/or the SS2.

29. The nucleic acid molecule of claim 8, wherein:
(i) the SS1 is about 2.0 Kb to about 5.0 Kb;
(ii) the SS2 is about 2.0 Kb to about 5.0 Kb;
(iii) the SS1 and the SS2 together are about 4.0 Kb to about 10.0 Kb;
(iv) the HPM and the SS1 or the SS2 together are about 5.0 Kb to about 10.0 Kb; and/or
(v) the HPM, the SS1, and the SS2 together are about 10.0 Kb to about 15.0 Kb.

30. The nucleic acid molecule of claim 8, wherein the ITR1 and/or the ITR2 is a parvoviral ITR.

31. The nucleic acid molecule of claim 30, wherein the parvoviral ITR is an adeno-associated virus (AAV) ITR.

32. The nucleic acid molecule of claim 31, wherein the AAV ITR is an AAV serotype 2 ITR.

33. A vector comprising the nucleic acid molecule of claim 8.

34. A plurality of viral particles comprising the nucleic acid molecule of claim 8.

35. A host cell comprising the vector of claim 8.

36. The nucleic acid of claim 8, wherein the SS1 has the nucleic acid sequence of SEQ ID NO: 3.

37. The nucleic acid of claim 36, wherein the SS2 has the nucleic acid sequence of SEQ ID NO: 4.

38. The nucleic acid of claim 8, wherein the SS2 has the nucleic acid sequence of SEQ ID NO: 3.

39. The nucleic acid of claim 8, wherein the SS1 has the nucleic acid sequence of SEQ ID NO: 4.

40. The nucleic acid of claim 39, wherein the SS2 has the nucleic acid sequence of SEQ ID NO: 3.

41. The nucleic acid of claim 8, wherein the SS2 has the nucleic acid sequence of SEQ ID NO: 4.

42. A method of producing a plurality of viral particles, the method comprising introducing into a host cell in a cell culture medium the nucleic acid molecule of claim 8 and isolating the plurality of viral particles from the cell culture medium.

43. A nucleic acid molecule comprising:
   (i) a SS1;
   (ii) an ITR1;
   (iii) a first homology arm (HR1);
   (iv) a CS;
   (v) a second homology arm (HR2);
   (vi) an ITR2; and
   (vii) a SS2;
   operably linked to each other in a 5'-to-3' direction as: SS1-ITR1-HR1-CS-HR2-ITR2-SS2, wherein the SS1 and the SS2 each, independently, comprise a portion having at least 85% sequence identity to a nucleic acid sequence selected from the group consisting of the nucleic acid sequences of SEQ ID NOS: 3-5 and 9-11, and wherein neither the SS1 nor the SS2 comprises an open reading frame that encodes more than 100 amino acids.

44. A nucleic acid molecule comprising:
   (i) a SS1;
   (ii) an ITR1;
   (iii) a HR1;
   (iv) a HPM;
   (v) a HR2;
   (vi) an ITR2; and
   (vii) a SS2;
   operably linked to each other in a 5'-to-3' direction as: SS1-ITR1-HR1-HPM-HR2-ITR2-SS2, wherein the SS1 and the SS2 each, independently, comprise a portion having at least 85% sequence identity to a nucleic acid sequence selected from the group consisting of the nucleic acid sequences of SEQ ID NOS: 3-5 and 9-11, and wherein neither the SS1 nor the SS2 comprises an open reading frame that encodes more than 100 amino acids.

45. A nucleic acid molecule comprising the formula of (SS1-ITR1-CS-ITR2-SS2)n, wherein
   (i) the SS1 is a first spacer;
   (ii) the ITR1 is a first inverted terminal repeat;
   (iii) the CS is a cloning site;
   (iv) the ITR2 is a second inverted terminal repeat; and
   (v) the SS2 is a second spacer;
   wherein said SS1, said ITR1, said CS, said ITR2, and said SS2 are operably linked to each other in a 5'-to-3' direction, and wherein the n is an integer greater than 1, wherein the SS1 and the SS2 together comprise a portion that has at least 85% sequence identity to a nucleic acid sequence selected from the group consisting of the nucleic acid sequences of SEQ ID NOS: 3-5 and 9-11, and wherein neither the SS1 nor the SS2 comprises an open reading frame that encodes more than 100 amino acids.

46. A nucleic acid molecule comprising the formula of (SS1-ITR1-HPM-ITR2-SS2)n, wherein
   (i) the SS1 is a first spacer;
   (ii) the ITR1 is a first inverted terminal repeat;
   (iii) the HPM is a heterologous polynucleotide molecule;
   (iv) the ITR2 is a second inverted terminal repeat; and
   (v) the SS2 is a second spacer;
   wherein said SS1, said ITR1, said HPM, said ITR2, and said SS2 are operably linked to each other in a 5'-to-3' direction, and wherein the n is an integer greater than 1, wherein the SS1 and the SS2 together comprise a portion that has at least 85% sequence identity to a nucleic acid sequence selected from the group consisting of the nucleic acid sequences of SEQ ID NOS: 3-5 and 9-11, and wherein nether the SS1 nor the SS2 comprises an open reading frame that encodes more than 100 amino acids.

47. The nucleic acid molecule of claim 46, wherein the n is an integer from 20 to 40.

48. The nucleic acid molecule of claim 46, wherein neither the SS1 nor the SS2 comprises an open reading frame that encodes more than 50 amino acids.

49. The nucleic acid molecule of claim 46, wherein the SS1 and the SS2 together do not comprise a prokaryotic or a baculoviral transcription factor binding site.

50. The nucleic acid molecule of claim 46, wherein the SS1 and the SS2 together have a total CpG content that is less than 1% of the combined nucleic acid sequence of the SS1 and the SS2.

51. The nucleic acid molecule of claim 50, wherein the SS1 and the SS2 together have a total CpG content that is less than 0.5% of the combined nucleic acid sequence of the SS1 and the SS2.

52. The nucleic acid molecule of claim 46, wherein:
   (i) the SS1 is about 1.0 Kb to about 2.5 Kb;
   (ii) the SS2 is about 1.0 Kb to about 2.5 Kb;
   (iii) the SS1 and the SS2 together are about 2.0 Kb to about 5.0 Kb;
   (iv) the HPM and the SS1 or the SS2 together are about 4.0 Kb to about 7.5 Kb; and/or
   (v) the HPM, the SS1, and the SS2 together are about 5.0 Kb to about 10.0 Kb.

53. The nucleic acid molecule of claim 46, wherein the ITR1 and/or the ITR2 is a parvoviral ITR.

54. The nucleic acid molecule of claim 53, wherein the parvoviral ITR is an AAV ITR.

55. The nucleic acid molecule of claim 54, wherein the AAV ITR is an AAV serotype 2 ITR.

56. A vector comprising the nucleic acid molecule of claim 46.

* * * * *